(12) United States Patent
Tully et al.

(10) Patent No.: US 12,292,564 B2
(45) Date of Patent: May 6, 2025

(54) SYSTEMS AND METHODS FOR MEDICAL IMAGING

(71) Applicant: Activ Surgical, Inc., Boston, MA (US)

(72) Inventors: Stephen Tully, Milton, MA (US); John Oberlin, Dorchester, MA (US); Emanuel Demaio, Cambridge, MA (US); Liam O'Shea, Westwood, MA (US); Vasiliy E. Buharin, Arlington, MA (US); Thomas Calef, Bridgewater, MA (US)

(73) Assignee: Activ Surgical, Inc., Boston, MA (US)

( * ) Notice: Subject to any disclaimer, the term of this patent is extended or adjusted under 35 U.S.C. 154(b) by 0 days.

(21) Appl. No.: 18/637,306

(22) Filed: Apr. 16, 2024

(65) Prior Publication Data

US 2024/0280800 A1 Aug. 22, 2024

Related U.S. Application Data

(63) Continuation-in-part of application No. 18/630,502, filed on Apr. 9, 2024, and a continuation-in-part of
(Continued)

(51) Int. Cl.
*A61B 1/00* (2006.01)
*A61B 1/04* (2006.01)
(Continued)

(52) U.S. Cl.
CPC ...... *G02B 23/2484* (2013.01); *A61B 1/00009* (2013.01); *A61B 1/000094* (2022.02);
(Continued)

(58) Field of Classification Search
None
See application file for complete search history.

(56) References Cited

U.S. PATENT DOCUMENTS 4,349,014 A 9/1982 Takamatsu
4,576,456 A * 3/1986 Okino ............... G03B 9/16
352/216

(Continued)

FOREIGN PATENT DOCUMENTS

CN 102770071 A 11/2012
CN 103169446 A 6/2013
(Continued)

OTHER PUBLICATIONS

Boas, et al. Laser speckle contrast imaging in biomedical optics. J Biomed Opt. Jan.-Feb. 2010;15(1):011109. doi: 10.1117/1.3285504. 12 pages.
(Continued)

*Primary Examiner* — John P Leubecker
*Assistant Examiner* — Jae Woo
(74) *Attorney, Agent, or Firm* — Wilson Sonsini Goodrich & Rosati

(57) ABSTRACT

The present disclosure provides systems and methods for medical imaging. The system may comprise an optical adapter. The optical adapter may comprise a housing that comprises (1) a first end configured to releasably couple to a scope and (2) a second end configured to releasably couple to a camera. The optical adapter may comprise an image sensor coupled to the housing. The optical adapter may comprise an optics assembly disposed in the housing. The optics assembly may be configured to (1) receive light signals that are reflected from a target site within a subject's body and transmitted through the scope, and (2) reflect a first portion of the light signals onto the image sensor while permitting a second portion of the light signals to pass through to the camera.

20 Claims, 40 Drawing Sheets

Related U.S. Application Data application No. 18/604,327, filed on Mar. 13, 2024, now abandoned, which is a continuation of application No. 18/365,839, filed on Aug. 4, 2023, now abandoned, which is a continuation of application No. 17/838,469, filed on Jun. 13, 2022, now Pat. No. 11,754,828, said application No. 18/630,502 is a continuation of application No. 17/752,617, filed on May 24, 2022, now abandoned, said application No. 17/838,469 is a continuation of application No. 17/150,708, filed on Jan. 15, 2021, now Pat. No. 11,389,051, said application No. 17/752,617 is a continuation of application No. PCT/US2020/062086, filed on Nov. 24, 2020, said application No. 17/150,708 is a continuation of application No. 16/882,297, filed on May 22, 2020, now Pat. No. 10,925,465, which is a continuation of application No. PCT/US2020/026920, filed on Apr. 6, 2020.

(60) Provisional application No. 62/952,892, filed on Dec. 23, 2019, provisional application No. 62/939,969, filed on Nov. 25, 2019, provisional application No. 62/830,934, filed on Apr. 8, 2019.

(51) Int. Cl.
 *A61B 1/06* (2006.01)
 *G02B 23/24* (2006.01)
 *H04N 23/51* (2023.01)
 *H04N 23/55* (2023.01)
 *H04N 23/56* (2023.01)
 *H04N 23/50* (2023.01)

(52) U.S. Cl.
 CPC .... *A61B 1/000096* (2022.02); *A61B 1/00105* (2013.01); *A61B 1/00126* (2013.01); *A61B 1/042* (2013.01); *A61B 1/046* (2022.02); *A61B 1/063* (2013.01); *A61B 1/0669* (2013.01); *H04N 23/51* (2023.01); *H04N 23/55* (2023.01); *H04N 23/56* (2023.01); *H04N 23/555* (2023.01)

(56) References Cited

U.S. PATENT DOCUMENTS

| | | | |
|---|---|---|---|
| 4,592,632 A * | 6/1986 | Renold | G03B 9/16 352/216 |
| 4,844,071 A | 7/1989 | Chen et al. | |
| 4,974,076 A * | 11/1990 | Nakamura | A61B 1/0638 358/509 |
| 5,748,930 A | 5/1998 | Prakash | |
| 5,749,830 A * | 5/1998 | Kaneko | A61B 1/0638 348/E5.038 |
| 5,980,450 A | 11/1999 | Thompson | |
| 6,069,698 A | 5/2000 | Ozawa et al. | |
| 6,088,105 A | 7/2000 | Link | |
| 6,373,963 B1 | 4/2002 | Demers et al. | |
| 6,438,302 B1 * | 8/2002 | Utsui | A61B 1/043 385/116 |
| 6,491,702 B2 | 12/2002 | Heilbrun et al. | |
| 6,503,195 B1 | 1/2003 | Keller et al. | |
| 6,537,211 B1 * | 3/2003 | Wang | A61B 1/0005 600/178 |
| 6,542,249 B1 | 4/2003 | Kofman et al. | |
| 6,549,288 B1 | 4/2003 | Migdal et al. | |
| 6,563,105 B2 | 5/2003 | Seibel et al. | |
| 6,564,086 B2 | 5/2003 | Marchitto et al. | |
| 6,613,041 B1 | 9/2003 | Schrunder | |
| 6,635,011 B1 * | 10/2003 | Ozawa | A61B 1/00096 348/E5.029 |
| 6,697,164 B1 | 2/2004 | Babayoff et al. | |
| 6,800,057 B2 | 10/2004 | Tsujita et al. | |
| 6,850,872 B1 | 2/2005 | Marschner et al. | |
| 6,873,867 B2 | 3/2005 | Vilsmeier | |
| 6,885,464 B1 | 4/2005 | Pfeiffer et al. | |
| RE38,800 E | 9/2005 | Barbour | |
| 6,965,690 B2 | 11/2005 | Matsumoto | |
| 6,977,732 B2 | 12/2005 | Chen et al. | |
| 6,987,531 B2 | 1/2006 | Kamon | |
| 7,006,236 B2 | 2/2006 | Tomasi et al. | |
| 7,068,825 B2 | 6/2006 | Rubbert et al. | |
| 7,092,107 B2 | 8/2006 | Babayoff et al. | |
| 7,099,732 B2 | 8/2006 | Geng | |
| 7,124,066 B2 | 10/2006 | Marschner et al. | |
| 7,152,024 B2 | 12/2006 | Marschner et al. | |
| 7,184,150 B2 | 2/2007 | Quadling et al. | |
| 7,200,262 B2 | 4/2007 | Sawada | |
| 7,224,384 B1 | 5/2007 | Iddan et al. | |
| 7,230,725 B2 | 6/2007 | Babayoff et al. | |
| 7,242,997 B2 | 7/2007 | Geng | |
| 7,305,110 B2 | 12/2007 | Rubbert et al. | |
| 7,313,264 B2 | 12/2007 | Crampton | |
| 7,319,529 B2 | 1/2008 | Babayoff | |
| 7,363,201 B2 | 4/2008 | Marschner et al. | |
| 7,385,708 B2 | 6/2008 | Ackerman et al. | |
| 7,433,807 B2 | 10/2008 | Marschner et al. | |
| 7,435,217 B2 | 10/2008 | Wiklof | |
| 7,450,783 B2 | 11/2008 | Talapov et al. | |
| 7,477,402 B2 | 1/2009 | Babayoff et al. | |
| 7,489,408 B2 | 2/2009 | Harding et al. | |
| 7,491,956 B2 | 2/2009 | Knoche et al. | |
| 7,492,927 B2 | 2/2009 | Marschner et al. | |
| 7,511,829 B2 | 3/2009 | Babayoff | |
| 7,522,764 B2 | 4/2009 | Schwotzer | |
| 7,577,299 B2 | 8/2009 | Kawamata et al. | |
| 7,620,209 B2 | 11/2009 | Stevick et al. | |
| 7,630,089 B2 | 12/2009 | Babayoff et al. | |
| 7,704,206 B2 | 4/2010 | Suzuki et al. | |
| 7,724,378 B2 | 5/2010 | Babayoff | |
| 7,724,932 B2 | 5/2010 | Ernst et al. | |
| 7,751,871 B2 | 7/2010 | Rubbert | |
| 7,763,841 B1 | 7/2010 | McEldowney | |
| 7,794,388 B2 | 9/2010 | Draxinger et al. | |
| 7,821,649 B2 | 10/2010 | Bendall et al. | |
| 7,854,700 B2 | 12/2010 | Orihara | |
| 7,898,651 B2 | 3/2011 | Hu et al. | |
| 7,944,569 B2 | 5/2011 | Babayoff et al. | |
| 7,951,073 B2 | 5/2011 | Freed | |
| 7,961,912 B2 | 6/2011 | Stevick et al. | |
| 7,967,743 B2 | 6/2011 | Ishihara | |
| 7,990,548 B2 | 8/2011 | Babayoff et al. | |
| 7,995,798 B2 | 8/2011 | Krupnik et al. | |
| 8,027,710 B1 | 9/2011 | Dannan | |
| 8,038,609 B2 | 10/2011 | Kohno et al. | |
| 8,084,753 B2 | 12/2011 | Joshi et al. | |
| 8,194,122 B2 | 6/2012 | Amling et al. | |
| 8,264,536 B2 | 9/2012 | McEldowney | |
| 8,279,418 B2 | 10/2012 | Yee et al. | |
| 8,280,152 B2 | 10/2012 | Thiel et al. | |
| 8,310,683 B2 | 11/2012 | Babayoff et al. | |
| 8,320,621 B2 | 11/2012 | McEldowney | |
| 8,326,020 B2 | 12/2012 | Lee et al. | |
| 8,330,804 B2 | 12/2012 | Lutian et al. | |
| 8,400,494 B2 | 3/2013 | Zalevsky et al. | |
| 8,406,859 B2 | 3/2013 | Zuzak et al. | |
| 8,471,897 B2 | 6/2013 | Rodriguez Ramos et al. | |
| 8,517,928 B2 | 8/2013 | Orihara | |
| 8,553,939 B2 | 10/2013 | Craig et al. | |
| 8,558,873 B2 | 10/2013 | McEldowney | |
| 8,593,507 B2 | 11/2013 | Yahav | |
| 8,610,665 B2 | 12/2013 | Craig et al. | |
| 8,649,024 B2 | 2/2014 | Colonna De Lega | |
| 8,659,765 B2 | 2/2014 | Ando | |
| 8,723,118 B2 | 5/2014 | McEldowney et al. | |
| 8,723,923 B2 | 5/2014 | Bloom et al. | |
| 8,755,053 B2 | 6/2014 | Fright et al. | |
| 8,792,098 B2 | 7/2014 | Dewald et al. | |
| 8,803,952 B2 | 8/2014 | Katz et al. | |
| 8,823,790 B2 | 9/2014 | Dunn et al. | |
| 8,891,087 B2 | 11/2014 | Zuzak et al. | |

(56) References Cited

U.S. PATENT DOCUMENTS

| | | |
|---|---|---|
| 8,896,594 B2 | 11/2014 | Xiong et al. |
| 8,974,378 B2 | 3/2015 | Imaizumi et al. |
| 9,001,190 B2 | 4/2015 | Olivier, III et al. |
| 9,057,784 B2 | 6/2015 | Hudman |
| 9,068,824 B2 | 6/2015 | Findeisen et al. |
| 9,070,194 B2 | 6/2015 | Lee et al. |
| 9,072,445 B2 | 7/2015 | Berguer et al. |
| 9,074,868 B2 | 7/2015 | Bendall et al. |
| 9,089,277 B2 | 7/2015 | Babayoff et al. |
| 9,119,552 B2 | 9/2015 | Baumann et al. |
| 9,135,502 B2 | 9/2015 | Haker et al. |
| 9,142,025 B2 | 9/2015 | Park et al. |
| 9,147,253 B2 | 9/2015 | Yee et al. |
| 9,149,348 B2 | 10/2015 | Wu et al. |
| 9,155,480 B2 | 10/2015 | Thakor et al. |
| 9,157,728 B2 | 10/2015 | Ogawa |
| 9,157,733 B2 | 10/2015 | Dillon et al. |
| 9,198,578 B2 | 12/2015 | Zuzak et al. |
| 9,204,952 B2 | 12/2015 | Lampalzer |
| 9,220,570 B2 | 12/2015 | Kim et al. |
| 9,226,645 B2 | 1/2016 | Ntziachristos |
| 9,226,673 B2 | 1/2016 | Ferguson, Jr. et al. |
| 9,247,865 B2 | 2/2016 | Igarashi et al. |
| 9,254,076 B2 | 2/2016 | McDowall |
| 9,254,078 B2 | 2/2016 | McDowall |
| 9,254,103 B2 | 2/2016 | Krishnaswamy et al. |
| 9,261,356 B2 | 2/2016 | Lampert et al. |
| 9,261,358 B2 | 2/2016 | Atiya et al. |
| 9,271,633 B2 | 3/2016 | Scott et al. |
| 9,271,658 B2 | 3/2016 | Ferguson, Jr. et al. |
| 9,274,047 B2 | 3/2016 | Velten et al. |
| 9,282,926 B2 | 3/2016 | Schwotzer et al. |
| 9,294,758 B2 | 3/2016 | Xiong et al. |
| 9,297,889 B2 | 3/2016 | Hudman et al. |
| 9,304,603 B2 | 4/2016 | Miller |
| 9,330,464 B1 | 5/2016 | Ackerman et al. |
| 9,345,389 B2 | 5/2016 | Nie et al. |
| 9,345,392 B2 | 5/2016 | Saito |
| 9,345,397 B2 | 5/2016 | Taylor et al. |
| 9,351,643 B2 | 5/2016 | Sharonov |
| 9,364,300 B2 | 6/2016 | Tchouprakov et al. |
| 9,375,844 B2 | 6/2016 | Itkowitz et al. |
| 9,377,295 B2 | 6/2016 | Fright et al. |
| 9,380,224 B2 | 6/2016 | Keskin et al. |
| 9,389,068 B2 | 7/2016 | Ri |
| 9,404,741 B2 | 8/2016 | Schick |
| 9,432,593 B2 | 8/2016 | Yang et al. |
| 9,439,568 B2 | 9/2016 | Atiya et al. |
| 9,443,310 B2 | 9/2016 | Hudman et al. |
| 9,444,981 B2 | 9/2016 | Bellis et al. |
| 9,451,872 B2 | 9/2016 | Yokota |
| 9,462,253 B2 | 10/2016 | Hudman et al. |
| 9,471,864 B2 | 10/2016 | Zatloukal et al. |
| 9,491,441 B2 | 11/2016 | Sarmast et al. |
| 9,494,418 B2 | 11/2016 | Schmidt |
| 9,506,749 B2 | 11/2016 | Bellis et al. |
| 9,513,113 B2 | 12/2016 | Yang et al. |
| 9,513,768 B2 | 12/2016 | Zhao et al. |
| 9,545,220 B2 | 1/2017 | Sidlesky |
| 9,554,692 B2 | 1/2017 | Levy |
| 9,557,574 B2 | 1/2017 | McEldowney |
| 9,581,802 B2 | 2/2017 | Yokota |
| 9,615,901 B2 | 4/2017 | Babayoff et al. |
| 9,622,644 B2 | 4/2017 | Yokota |
| 9,622,662 B2 | 4/2017 | Zuzak et al. |
| 9,638,801 B2 | 5/2017 | Boufounos et al. |
| 9,674,436 B2 | 6/2017 | Crane et al. |
| 9,675,429 B2 | 6/2017 | Lampert et al. |
| 9,690,984 B2 | 6/2017 | Butler et al. |
| 9,696,427 B2 | 7/2017 | Wilson et al. |
| 9,720,506 B2 | 8/2017 | Kim et al. |
| 9,729,860 B2 | 8/2017 | Cohen et al. |
| 9,737,239 B2 | 8/2017 | Kimmel |
| 9,739,594 B2 | 8/2017 | Koerner et al. |
| 9,746,318 B2 | 8/2017 | Sugano |
| 9,752,867 B2 | 9/2017 | Atiya et al. |
| 9,782,056 B2 | 10/2017 | McDowall |
| 9,788,903 B2 | 10/2017 | Kim et al. |
| 9,799,117 B2 | 10/2017 | Chen et al. |
| 9,817,159 B2 | 11/2017 | Hudman |
| 9,833,145 B2 | 12/2017 | Jeong et al. |
| 9,841,496 B2 | 12/2017 | Hudman |
| 9,844,427 B2 | 12/2017 | Atiya et al. |
| 9,901,409 B2 | 2/2018 | Yang et al. |
| 9,918,640 B2 | 3/2018 | Ntziachristos et al. |
| 9,922,249 B2 | 3/2018 | Kang et al. |
| 9,939,258 B2 | 4/2018 | Lampert et al. |
| 9,943,271 B2 | 4/2018 | Dirauf et al. |
| 9,947,099 B2 | 4/2018 | Bleyer et al. |
| 9,953,428 B2 | 4/2018 | Gren et al. |
| 9,955,140 B2 | 4/2018 | Rhemann et al. |
| 9,955,861 B2 | 5/2018 | Gao et al. |
| 9,958,585 B2 | 5/2018 | Powell et al. |
| 9,958,758 B2 | 5/2018 | Hudman |
| 9,962,244 B2 | 5/2018 | Esbech et al. |
| 9,970,753 B2 | 5/2018 | Han et al. |
| 10,011,014 B2 | 7/2018 | Divoky et al. |
| 10,018,464 B2 | 7/2018 | Boles et al. |
| 10,024,968 B2 | 7/2018 | Hudman et al. |
| 10,039,439 B2 | 8/2018 | Aoyama |
| 10,045,882 B2 | 8/2018 | Balicki et al. |
| 10,055,856 B2 | 8/2018 | Sabater et al. |
| 10,058,256 B2 | 8/2018 | Chen et al. |
| 10,066,997 B2 | 9/2018 | Korner et al. |
| 10,089,737 B2 | 10/2018 | Krieger et al. |
| 10,169,862 B2 | 1/2019 | Andre et al. |
| 10,244,991 B2 | 4/2019 | Shademan et al. |
| 10,390,718 B2 | 8/2019 | Chen et al. |
| 10,398,519 B2 | 9/2019 | Kim et al. |
| 10,575,737 B2 | 3/2020 | Andre et al. |
| 10,675,040 B2 | 6/2020 | Kim et al. |
| 10,681,259 B2 | 6/2020 | Ichiki et al. |
| 10,694,117 B2 | 6/2020 | Frangioni |
| 10,722,173 B2 | 7/2020 | Chen et al. |
| 10,792,492 B2 | 10/2020 | Chen et al. |
| 10,925,465 B2 | 2/2021 | Tully et al. |
| 10,948,350 B2 | 3/2021 | Ferguson, Jr. et al. |
| 10,966,597 B2 | 4/2021 | Yamazoe et al. |
| 11,135,028 B2 | 10/2021 | Kim et al. |
| 11,278,220 B2 | 3/2022 | Tucker et al. |
| 11,389,051 B2 | 7/2022 | Tully et al. |
| 11,754,828 B2 | 9/2023 | Tully et al. |
| 11,977,218 B2 | 5/2024 | Dehghani et al. |
| 2001/0030983 A1 | 10/2001 | Yuri et al. |
| 2002/0021355 A1* | 2/2002 | Utsui ............... H04N 23/56 348/E5.029 |
| 2002/0022768 A1* | 2/2002 | Utsui ............... A61B 1/0669 600/178 |
| 2003/0050532 A1* | 3/2003 | Doguchi ........... A61B 5/0071 348/E5.029 |
| 2003/0176768 A1* | 9/2003 | Gono ............... A61B 1/0655 600/109 |
| 2003/0195623 A1 | 10/2003 | Marchitto et al. |
| 2004/0257438 A1* | 12/2004 | Doguchi ........... A61B 1/0646 348/E5.035 |
| 2005/0010084 A1 | 1/2005 | Tsai |
| 2005/0096515 A1 | 5/2005 | Geng |
| 2005/0220447 A1* | 10/2005 | Ito .................. A61B 1/07 396/17 |
| 2005/0267329 A1 | 12/2005 | Konstorum et al. |
| 2006/0173240 A1 | 8/2006 | Fukuyama et al. |
| 2007/0055103 A1 | 3/2007 | Hoefig et al. |
| 2007/0115484 A1 | 5/2007 | Huang et al. |
| 2007/0146719 A1 | 6/2007 | Wedel |
| 2007/0165243 A1 | 7/2007 | Kang et al. |
| 2007/0276185 A1* | 11/2007 | Gono ............... A61B 5/0261 600/156 |
| 2007/0280423 A1 | 12/2007 | Schmidt |
| 2008/0107305 A1 | 5/2008 | Vanderkooy et al. |
| 2008/0218826 A1 | 9/2008 | Desaulniers |
| 2008/0266391 A1 | 10/2008 | Lee et al. |
| 2009/0216085 A1 | 8/2009 | Yamazaki |
| 2009/0221874 A1 | 9/2009 | Vinther et al. |
| 2009/0244260 A1 | 10/2009 | Takahashi et al. |

(56) References Cited

U.S. PATENT DOCUMENTS

| | | |
|---|---|---|
| 2009/0289200 A1 | 11/2009 | Ishii |
| 2010/0097454 A1 | 4/2010 | Kubo et al. |
| 2010/0113921 A1 | 5/2010 | Fear et al. |
| 2010/0210904 A1 | 8/2010 | Cline et al. |
| 2011/0015518 A1 | 1/2011 | Schmidt et al. |
| 2011/0043609 A1 | 2/2011 | Choi et al. |
| 2011/0057930 A1 | 3/2011 | Keller et al. |
| 2011/0069162 A1 | 3/2011 | Ozawa et al. |
| 2011/0071352 A1 | 3/2011 | Ozawa et al. |
| 2011/0080471 A1 | 4/2011 | Song et al. |
| 2011/0115882 A1* | 5/2011 | Shahinian .......... A61B 1/00193 348/E13.001 |
| 2011/0123098 A1 | 5/2011 | Ernst et al. |
| 2011/0245844 A1 | 10/2011 | Jinno |
| 2012/0075432 A1 | 3/2012 | Bilbrey et al. |
| 2012/0095354 A1 | 4/2012 | Dunn et al. |
| 2012/0101348 A1 | 4/2012 | Yamaguchi et al. |
| 2012/0165681 A1 | 6/2012 | Keller |
| 2012/0206587 A1 | 8/2012 | Oz et al. |
| 2012/0307512 A1 | 12/2012 | Cogger et al. |
| 2012/0310098 A1 | 12/2012 | Popovic |
| 2013/0023732 A1 | 1/2013 | Kim et al. |
| 2013/0041267 A1 | 2/2013 | Ntziachristos et al. |
| 2013/0253313 A1 | 9/2013 | Kang et al. |
| 2013/0274596 A1 | 10/2013 | Azizian et al. |
| 2013/0296712 A1 | 11/2013 | Durvasula |
| 2014/0031665 A1 | 1/2014 | Pinto et al. |
| 2014/0051923 A1 | 2/2014 | Mirza et al. |
| 2014/0052005 A1 | 2/2014 | Yokota |
| 2014/0071257 A1 | 3/2014 | Yokota |
| 2014/0092281 A1 | 4/2014 | Nisenzon et al. |
| 2014/0194747 A1 | 7/2014 | Kruglick et al. |
| 2014/0221749 A1 | 8/2014 | Grant et al. |
| 2014/0309495 A1 | 10/2014 | Kirma et al. |
| 2014/0378845 A1 | 12/2014 | Nadkarni |
| 2015/0099925 A1 | 4/2015 | Davidson et al. |
| 2015/0164329 A1 | 6/2015 | Schmidt et al. |
| 2015/0238276 A1 | 8/2015 | Atarot et al. |
| 2015/0377613 A1 | 12/2015 | Small et al. |
| 2015/0381909 A1 | 12/2015 | Butte et al. |
| 2016/0100908 A1 | 4/2016 | Tesar |
| 2016/0128553 A1 | 5/2016 | Geng |
| 2016/0139039 A1 | 5/2016 | Ikehara et al. |
| 2016/0239978 A1 | 8/2016 | Cole et al. |
| 2016/0260206 A1 | 9/2016 | Jung et al. |
| 2016/0262615 A1 | 9/2016 | Jung et al. |
| 2016/0278678 A1 | 9/2016 | Valdes et al. |
| 2016/0300348 A1 | 10/2016 | Nadeau et al. |
| 2016/0302880 A1 | 10/2016 | Uhlemann et al. |
| 2016/0307325 A1 | 10/2016 | Wang et al. |
| 2016/0307326 A1 | 10/2016 | Wang |
| 2016/0309068 A1 | 10/2016 | Nadeau et al. |
| 2016/0335472 A1 | 11/2016 | Lee et al. |
| 2017/0014030 A1 | 1/2017 | Rentschler et al. |
| 2017/0020393 A1 | 1/2017 | Rentschler et al. |
| 2017/0026633 A1 | 1/2017 | Riza |
| 2017/0030710 A1 | 2/2017 | Rentschler et al. |
| 2017/0032531 A1 | 2/2017 | Nagata et al. |
| 2017/0059305 A1 | 3/2017 | Nonn et al. |
| 2017/0059849 A1 | 3/2017 | Daidoji et al. |
| 2017/0079724 A1 | 3/2017 | Yang et al. |
| 2017/0095299 A1 | 4/2017 | Hendrick et al. |
| 2017/0100024 A1 | 4/2017 | Shahmoon et al. |
| 2017/0143237 A1 | 5/2017 | Yokota |
| 2017/0155818 A1 | 6/2017 | Bonnet |
| 2017/0164836 A1 | 6/2017 | Krishnaswamy et al. |
| 2017/0172382 A1 | 6/2017 | Nir et al. |
| 2017/0172384 A1 | 6/2017 | Yokota |
| 2017/0172394 A1 | 6/2017 | Scott et al. |
| 2017/0209031 A1 | 7/2017 | Nakamura et al. |
| 2017/0224274 A1 | 8/2017 | Chen et al. |
| 2017/0227942 A1 | 8/2017 | Thomson et al. |
| 2017/0228879 A1 | 8/2017 | Sato |
| 2017/0251900 A1 | 9/2017 | Hansen et al. |
| 2017/0280970 A1 | 10/2017 | Sartor et al. |
| 2017/0311778 A1 | 11/2017 | Hasser et al. |
| 2017/0328704 A1 | 11/2017 | Atiya et al. |
| 2017/0347043 A1 | 11/2017 | Rephaeli et al. |
| 2017/0351103 A1 | 12/2017 | Duckett et al. |
| 2017/0366773 A1 | 12/2017 | Kiraly et al. |
| 2018/0003943 A1 | 1/2018 | Chan |
| 2018/0008371 A1 | 1/2018 | Manus |
| 2018/0042466 A1 | 2/2018 | Kang et al. |
| 2018/0047165 A1 | 2/2018 | Sato |
| 2018/0104009 A1 | 4/2018 | Abhari et al. |
| 2018/0125586 A1 | 5/2018 | Sela et al. |
| 2018/0165823 A1 | 6/2018 | Ludwig |
| 2018/0174318 A1 | 6/2018 | Wang et al. |
| 2018/0235715 A1 | 8/2018 | Amiot et al. |
| 2018/0243043 A1 | 8/2018 | Michihata et al. |
| 2018/0279954 A1 | 10/2018 | Hayam et al. |
| 2019/0000308 A1 | 1/2019 | Duckett, III et al. |
| 2019/0239730 A1 | 8/2019 | Myung et al. |
| 2019/0246873 A1 | 8/2019 | Lu et al. |
| 2019/0265490 A1 | 8/2019 | Duckett, III |
| 2020/0107710 A1 | 4/2020 | Duckett, III et al. |
| 2020/0143545 A1 | 5/2020 | Weng et al. |
| 2020/0305721 A1 | 10/2020 | Chen et al. |
| 2020/0315432 A1 | 10/2020 | Tully et al. |
| 2021/0030277 A1 | 2/2021 | Ferguson, Jr. et al. |
| 2021/0282630 A1 | 9/2021 | Kikuchi et al. |
| 2021/0282654 A1 | 9/2021 | Cha et al. |
| 2021/0338060 A1 | 11/2021 | Tully et al. |
| 2022/0287553 A1 | 9/2022 | Tully et al. |
| 2022/0377217 A1 | 11/2022 | Dehghani et al. |
| 2022/0378280 A1 | 12/2022 | Tully et al. |
| 2023/0105882 A1* | 4/2023 | Abe ................ C04B 35/597 600/178 |
| 2024/0353669 A1 | 10/2024 | Dehghani et al. |

FOREIGN PATENT DOCUMENTS

| | | |
|---|---|---|
| CN | 107124547 A | 9/2017 |
| CN | 107510430 A | 12/2017 |
| EP | 2625998 A1 | 8/2013 |
| EP | 2604177 B1 | 4/2016 |
| JP | H10290780 A | 11/1998 |
| JP | 2006187427 A | 7/2006 |
| JP | 2007037783 A | 2/2007 |
| JP | 2007229135 A | 9/2007 |
| JP | 2009022652 A | 2/2009 |
| JP | 2009095554 A | 5/2009 |
| JP | 2010017377 A | 1/2010 |
| JP | 2015231498 A | 12/2015 |
| JP | 2018042676 A | 3/2018 |
| KR | 20170051264 A | 5/2017 |
| KR | 20180066645 A | 6/2018 |
| WO | WO-2010096447 A2 | 8/2010 |
| WO | WO-2010096453 A1 | 8/2010 |
| WO | WO-2012096878 A2 | 7/2012 |
| WO | WO-2014152753 A1 | 9/2014 |
| WO | WO-2016061052 A1 | 4/2016 |
| WO | WO-2016153741 A1 | 9/2016 |
| WO | WO-2017075602 A1 | 5/2017 |
| WO | WO-2018021035 A1 | 2/2018 |
| WO | WO-2019045971 A1 | 3/2019 |
| WO | WO-2020006454 A1 | 1/2020 |
| WO | WO-2020210168 A1 | 10/2020 |
| WO | WO-2021035094 A1 | 2/2021 |
| WO | WO-2021108450 A1 | 6/2021 |
| WO | WO-2022029308 A1 | 2/2022 |
| WO | WO-2022058499 A1 | 3/2022 |
| WO | WO-2023091515 A1 | 5/2023 |
| WO | WO-2023205456 A1 | 10/2023 |

OTHER PUBLICATIONS

Bray et al. Endoscopic laser speckle imaging of tissue blood flow: applications in the human knee. Journal of Orthopaedic Research, pp. 1650-1659 (2006).

Cha et al. Dual-display laparoscopic laser speckle contrast imaging for real-time surgical assistance. Biomedical Optics Express, 9(12)

(56) References Cited

OTHER PUBLICATIONS pp. 1-20 (2018). Available at https://hsrc.himmelfarb.gwu.edu/cgi/viewcontent.cgi?article=3662&context=smhs_peds_facpubs.
Co-pending U.S. Appl. No. 18/604,327, inventors Tully; Stephen et al., filed Mar. 13, 2024.
Co-pending U.S. Appl. No. 18/614,393, inventors Dehghani; Hossein et al., filed Mar. 22, 2024.
Co-pending U.S. Appl. No. 18/630,502, inventors Tully; Stephen et al., filed Apr. 9, 2024.
EP20788162.4 European Search Report and Opinion dated Mar. 7, 2023.
EP20855369.3 Extended European Search Report dated Nov. 14, 2023.
EP20855369.3 Supplementary European Search Report dated Aug. 10, 2023.
EP20892307.8 Extended European Search Report dated Nov. 6, 2023.
Holstein-Rathlou, et al. Nephron blood flow dynamics measured by laser speckle contrast imaging. Am J Physiol Renal Physiol. Feb. 2011;300(2):F319-29. doi: 10.1152/ajprenal.00417.2010. Epub Nov. 3, 2010.
Kadambi et al. Rethinking machine vision time of flight with GHz heterodying. IEEE Access. vol. 5, 1-13, Nov. 2017.
Li et al. SH-ToF: Micro Resolution Time-of-Flight Imaging with Superheterodyne Interferometry, IEEE ICCP, 2018: 1-10.
PCT/US2020/026920 International Preliminary Report on Patentability dated Sep. 28, 2021.
PCT/US2020/026920 International search report with written opinion dated Jun. 26, 2020.
PCT/US2020/047275 International Search Report & Written Opinion dated Feb. 1, 2021.
PCT/US2020/062086 International Search Report and Written Opinion dated Feb. 10, 2021.
PCT/US2022/050147 International Search Report and Written Opinion dated Apr. 6, 2023.
PCT/US2023/019457 International Search Report and Written Opinion dated Aug. 21, 2023.
Richards, et al. Intraoperative laser speckle contrast imaging with retrospective motion correction for quantitative assessment of cerebral blood flow. Neurophotonics. Jul. 2014;1(1):015006. doi: 10.1117/1.NPh.1.1.015006. Epub Aug. 18, 2014. 12 pages.
Richards et al. Low-cost laser speckle contrast imaging of blood flow using a webcam. Biomed Opt Express. Sep. 26, 2013;4(10):2269-83. doi: 10.1364/BOE.4.002269. eCollection 2013.
U.S. Appl. No. 17/150,708 Notice of Allowance dated Apr. 12, 2022.
U.S. Appl. No. 16/882,297 Notice of Allowance dated Nov. 6, 2020.
U.S. Appl. No. 16/882,297 Office Action dated Aug. 7, 2020.
U.S. Appl. No. 17/150,708 Office Action dated Oct. 26, 2021.
U.S. Appl. No. 17/673,324 Notice of Allowance dated Dec. 26, 2023.
U.S. Appl. No. 17/673,324 Office Action dated Sep. 8, 2023.
U.S. Appl. No. 17/752,617 Office Action dated Jul. 13, 2023.
U.S. Appl. No. 17/752,617 Office Action dated Mar. 6, 2023.
U.S. Appl. No. 17/752,617 Office Action dated Oct. 12, 2023.
U.S. Appl. No. 17/838,469 Notice of Allowance dated Jul. 20, 2023.
U.S. Appl. No. 17/838,469 Office Action dated Jun. 9, 2023.
Co-pending U.S. Appl. No. 18/710,574, inventors Mach; Anderson et al., filed May 15, 2024.
Co-pending U.S. Appl. No. 18/927,245, inventors Tully; Stephen et al., filed Oct. 25, 2024.
U.S. Appl. No. 18/614,393 Office Action dated Jan. 3, 2025.

* cited by examiner

SYSTEMS AND METHODS FOR MEDICAL IMAGING

CROSS-REFERENCE

This application is a continuation in part of U.S. patent application Ser. No. 18/604,327 filed on Mar. 13, 2024, which is a continuation of U.S. patent application Ser. No. 18/365,839 filed on Aug. 4, 2023, now abandoned, which is a continuation of U.S. patent application Ser. No. 17/838,469 filed on Jun. 13, 2022, now U.S. Pat. No. 11,754,828, issued Sep. 12, 2023, which is a continuation of U.S. patent application Ser. No. 17/150,708 filed on Jan. 15, 2021, now U.S. Pat. No. 11,389,051, issued Jul. 19, 2022, which is a continuation of U.S. patent application Ser. No. 16/882,297 filed on May 22, 2020, now U.S. Pat. No. 10,925,465, issued Feb. 23, 2021, which is a continuation application of International Application No. PCT/US2020/026920 filed on Apr. 6, 2020, which claims priority to U.S. Provisional Patent Application No. 62/830,934 filed on Apr. 8, 2019, and U.S. Provisional Patent Application No. 62/952,892 filed on Dec. 23, 2019; and this application is also a continuation in part of U.S. patent application Ser. No. 18/630,502 filed on Apr. 9, 2024, which is a continuation application of U.S. patent application Ser. No. 17/752,617 filed on May 24, 2022, now abandoned, which is a continuation application of International Application No. PCT/US2020/062086 filed on Nov. 24, 2020, which claims priority to U.S. Provisional Patent Application No. 62/939,969 filed on Nov. 25, 2019, which applications are incorporated herein by reference in their entirety for all purposes.

BACKGROUND

Medical imaging technology (e.g., a scope assembly, such as an endoscope) may be used to capture images or video data of internal anatomical or physiological features of a subject or patient during medical or surgical procedures. The images or video data captured may be processed and manipulated to provide medical practitioners (e.g., surgeons, medical operators, technicians, etc.) with a visualization of internal structures or processes within a patient or subject. Conventional medical imaging systems available today may use one or more dyes to help visualize internal processes such as blood flow. Such systems may limit the time frame during which an operator may visualize changes in blood flow.

Images or video data of internal anatomical or physiological features by an endoscope may be limited and often fail to provide complex anatomy or critical structures beneath the tissue surface. The images or video data may not show invisible features of the target site in real-time, e.g., blood perfusion, cardiac output, hepatic function, etc. As a result, incomplete or incorrect analysis of the target site may be dangerous and lead to unintended tissue damage during surgical procedures. In some cases, at least 2% of hysterectomies may result in surgical complications and unintended injuries, which may result in healthcare costs of at least $1 billion annually in the U.S.

Additional diagnostic tools such as fluorescent dye-based angiography (e.g., indocyanine green (ICG) angiography) may be used in conjunction to provide visualization of some complex anatomy or critical structures. However, ICG angiography may be costly in resources and time (e.g., may require several minutes to 24 hours for the ICG dye to reach a target site), limited in accuracy (e.g., dyes may dissipate to off-target sites during surgical procedures), elicit allergic reactions in some patients, and/or lack real-time visualization capability. In addition, use of separate imaging tools for endoscopy and angiography may lead to further surgical complications, such as prolonged surgical time or chances of contamination.

SUMMARY

The present disclosure addresses at least the abovementioned shortcomings of conventional medical imaging systems. In one aspect, the present disclosure provides an optical adapter that is compatible with one or more medical imaging technologies (e.g., a scope assembly). In some cases, the optical adapter may allow visualization of additional or multiple feature(s) of the target site without need for the use of the dye(s).

One aspect of the present disclosure provides an optical adapter comprising: a housing comprising (1) a first end configured to releasably couple to a scope and (2) a second end configured to releasably couple to a camera; an image sensor in the housing; and an optics assembly disposed in the housing, wherein the optics assembly is configured to (i) receive light signals that are reflected from a target site within a subject's body and transmitted through the scope, and (ii) reflect a first portion of the light signals onto one of the image sensor or the camera, while permitting a second portion of the light signals to pass through to the other of the image sensor or the camera.

In some embodiments, the image sensor is releasably coupled to the housing.

In some embodiments, the image sensor is configured to generate a first set of imaging data from the first portion of the light signals, and the camera is configured to generate a second set of imaging data from the second portion of the light signals. In some embodiments, the first set of imaging data comprises laser speckle patterns, and the second set of imaging data comprises photographic or video images.

In some embodiments, the image sensor is used for laser speckle imaging.

In some embodiments, the optics assembly comprises a beam splitter. In some embodiments, the beam splitter comprises a dichroic mirror.

In some embodiments, the optics assembly is configured to reflect the first portion of the light signals onto the image sensor, while permitting the second portion of the light signals to pass through to the camera. In some embodiments, the optics assembly comprises a shortpass dichroic mirror.

In some embodiments, the optics assembly is configured to reflect the first portion of the light signals onto the camera, while permitting the second portion of the light signals to pass through to the image sensor. In some embodiments, the optics assembly comprises a longpass dichroic mirror.

In some embodiments, the first portion of the light signals comprises backscattered light that is generated when the target site is illuminated with coherent laser light transmitted via the scope. In some embodiments, the coherent laser light is provided from a single laser source having substantially a single wavelength. In some embodiments, the coherent laser light is provided from a plurality of laser sources having a plurality of different wavelengths.

In some embodiments, the second portion of the light signals comprises reflected light that is generated when the target site is illuminated with white light transmitted via the scope. In some embodiments, the single wavelength lies in an invisible spectrum. In some embodiments, the plurality of different wavelengths lies in an invisible spectrum. In some embodiments, the reflected light is in a visible spectrum.

In some embodiments, the first end of the housing is configured to releasably couple to the scope using a quick release mechanism. In some embodiments, the quick release mechanism is configured to releasably couple the optical adapter to various types of scopes having different sizes. In some embodiments, the quick release mechanism is configured to permit a user to releasably couple the first end of the housing to the scope without use of tools. In some embodiments, the quick release mechanism is configured to permit a user to releasably couple the first end of the housing to the scope in less than 30 seconds.

In some embodiments, the second end of the housing is configured to releasably couple to the camera using a quick release mechanism. In some embodiments, the quick release mechanism is configured to releasably couple the optical adapter to various types of cameras having different sizes. In some embodiments, the quick release mechanism is configured to permit a user to releasably couple the second end of the housing to the camera without use of tools. In some embodiments, the quick release mechanism is configured to permit a user to releasably couple the second end of the housing to the camera in less than 30 seconds.

In some embodiments, the optics assembly further comprises a focusing device for the image sensor.

In some embodiments, the optics assembly further comprises (i) a first focusing device for the image sensor and (ii) a second focusing device for the camera. In some embodiments, the first focusing device and the second focusing device are operably coupled to each other, such that focusing for the image sensor and for the camera can be performed concurrently. In some embodiments, the first focusing device and the second focusing device are operably coupled to each other via a gearing mechanism. In some embodiments, the first focusing device and the second focusing device are provided separately and configured to be used independently of each other.

In some embodiments, the scope is configured to (1) receive a combined light beam from an illumination source and (2) direct the combined light beam onto the target site within the subject's body.

In some embodiments, the first end and the second end share a common longitudinal axis. In some embodiments, the first end and the second end are provided on opposite sides of the housing.

In some embodiments, the first end and the second end do not share a common longitudinal axis. In some embodiments, the first end and the second end are provided on substantially orthogonal sides of the housing.

In some embodiments, the image sensor and the camera have different optical axes.

In some embodiments, an optical axis of the image sensor is orthogonal to an optical axis of the camera.

In some embodiments, the image sensor is configured to releasably couple to a surface of the housing, and wherein the surface is substantially orthogonal to the first end or the second end of the housing. In some embodiments, the image sensor comprises a casing that is configured to releasably couple to the surface of the housing.

In some embodiments, the image sensor is disposable and configured for single use in a medical imaging procedure.

In some embodiments, the image sensor is configured to be reusable for a plurality of medical imaging procedures.

Another aspect of the present disclosure provides an imaging kit comprising: any one of the subject optical adapters disclosed herein; and an illumination source configured to transmit a combined light beam to the scope for directing the combined light beam onto the target site within the subject's body.

Another aspect of the present disclosure provides a method comprising: (a) combining white light with coherent laser light to generate a combined light beam; (b) providing the combined light beam to a scope; (c) using the scope to direct the combined light beam onto a target site within a subject's body; (d) receiving, via the scope, light signals that are reflected from the target site; and (e) reflecting a first portion of the light signals onto one of (i) an image sensor in an optical adapter or (ii) a camera, while permitting a second portion of the light signals to pass through to the other of (i) the image sensor or (ii) the camera, wherein the optical adapter is configured to releasably couple to both the scope and the camera.

In some embodiments, the first portion of the light signals is reflected onto the image sensor, while the second portion of the light signals is permitted to pass through to the camera.

In some embodiments, the first portion of the light signals is reflected onto the camera, while the second portion of the light signals is permitted to pass through to the image sensor.

In some embodiments, the optical adapter is disposed between the scope and the camera when releasably coupled thereto.

In some embodiments, the scope and the camera are releasably coupled to orthogonal sides of the optical adapter.

Another aspect of the present disclosure provides a method comprising: (a) providing an optical adapter comprising a housing, wherein an image sensor is in the housing; (b) releasably coupling a first end of the housing to a scope; (c) releasably coupling a second end of the housing to a camera; (d) providing a combined light beam to the scope, wherein the combined light beam comprises white light combined with coherent laser light; (e) using the scope to direct the combined light beam onto a target site within a subject's body; (f) receiving, via the scope, light signals that are reflected from the target site; (g) reflecting a first portion of the light signals onto one of the image sensor or the camera, while permitting a second portion of the light signals to pass through to the other of the image sensor or the camera; and (h) using the image sensor to generate a first set of imaging data from the first portion of the light signals, and using the camera to generate a second set of imaging data from the second portion of the light signals.

In some embodiments, the first portion of the light signals is reflected onto the image sensor, while the second portion of the light signals is permitted to pass through to the camera.

In some embodiments, the first portion of the light signals is reflected onto the camera, while the second portion of the light signals is permitted to pass through to the image sensor.

In some embodiments, the first set of imaging data comprises laser speckle patterns.

In some embodiments, the second set of imaging data comprises photographic or video images.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Recognized herein are various limitations with medical imaging systems currently available. The present disclosure provides systems and methods to address existing shortcoming or deficiencies of conventional medical imaging systems. The systems and methods disclosed herein may be used to enhance medical imaging by selectively controlling the exposure of multiple illumination sources through one or more cut-outs of a movable plate and combining pulses of light from different multi-spectral illumination sources. As such, the system and methods disclosed herein may be implemented to visualize and digitally map anatomical structures within a patient in three-dimensional (3D) perspective, in real-time and without the use of dyes, thereby providing medical operators with additional visual information (e.g., a real-time visual depiction of a patient's blood perfusion) that can inform or guide them during a surgical procedure.

In an aspect, the present disclosure provides a system for illuminating a target region in a subject's body. The system may comprise: a plurality of illumination sources comprising at least two of (i) a white light source configured to generate a white light beam and (ii) one or more light emitting diodes (LEDs) or laser light sources configured to generate one or more laser light beams; and a movable plate comprising one or more cut-outs, wherein the movable plate is (i) optically aligned with one or more of the plurality of illumination sources and (ii) configured to move so as to (a) control an exposure of the one or more illumination sources through the one or more cut-outs, relative to a pre-determined frame capture rate, and (b) generate one or more light pulses based on the controlled exposure of the one or more illumination sources.

In some embodiments, the movable plate may be configured to rotate relative to the one or more illumination sources along an optical axis. In some embodiments, the movable plate may comprise a low transmittance material that is configured to prevent transmission of light through one or more solid portions of the movable plate.

In some embodiments, the one or more cut-outs may comprise a notch on the movable plate. In some embodiments, the one or more cut-outs may comprise a plurality of notches arranged on different portions of the movable plate. In some embodiments, the one or more cut-outs may comprise one or more annular-shaped openings on the movable plate.

In some embodiments, the one or more laser light sources may comprise two or more laser light sources that are configured to generate two or more laser light beams having different wavelengths. In some embodiments, the two or more laser light sources may comprise a gas laser, a chemical laser, a liquid laser, a dye laser, a metal-vapor laser, a solid-state laser, or a semiconductor laser. In some embodiments, the two or more laser light sources may comprise an infrared laser, a near-infrared laser, a short-wavelength infrared laser, a mid-wavelength infrared laser, a long-wavelength infrared laser, or a far-infrared laser. In some embodiments, the two or more laser light sources may be configured to generate two or more laser light beams with a wavelength between about 700 nanometers (nm) and about 1 millimeter (mm).

In some embodiments, the movable plate may be optically aligned with the one or more laser light sources. In some embodiments, the movable plate and the white light source may not share a common optical axis. In some embodiments, the white light source may be disposed relative to the movable plate such that the white light beam does not pass through the movable plate. In some embodiments, the white light beam from the white light source may be transmitted continuously without being affected or separated into pulses by the movable plate. In some embodiments, the one or more light pulses may be obtained from the one or more laser light beams.

In some embodiments, the system may further comprise a light aggregation module configured to (i) combine (a) the one or more light pulses obtained from the one or more laser light beams with (b) the white light beam to generate (c) a combined light beam, and (ii) provide the combined light beam to a scope. The scope may be insertable into the subject's body and configured to direct the combined light beam onto the target region.

In some embodiments, the movable plate may be optically aligned with (i) the white light source and (ii) the one or more laser light sources. In some embodiments, the one or more light pulses may be obtained from (i) the white light beam and (ii) the one or more laser light beams.

In some embodiments, the system may further comprise a light aggregation module configured to (i) combine (a) the one or more light pulses obtained from the white light beam with (b) the one or more light pulses obtained from the one or more laser light beams, to generate (c) a combined light beam, and (ii) provide the combined light beam to a scope. The scope may be insertable into the subject's body and configured to direct the combined light beam onto the target region.

In some embodiments, the plurality of illumination sources may further comprise (iii) an indocyanine green (ICG) excitation light source configured to generate an ICG excitation light beam. In some embodiments, the ICG excitation light source may be disposed relative to the movable plate such that the ICG excitation beam does not pass through the movable plate. In some embodiments, the movable plate may be optically aligned with (i) the one or more laser light sources. In some embodiments, the movable plate and the white light source may not share a common optical axis. In some embodiments, the white light beam from the white light source may be transmitted continuously without being affected or separated into pulses by the movable plate. In some embodiments, the movable plate and the ICG excitation light source may not share a common optical axis. In some embodiments, the ICG excitation light beam from the ICG excitation light source may be transmitted continuously without being affected or separated into pulses by the movable plate. In some embodiments, the one or more light pulses may be obtained from (i) the one or more laser light beams.

In some embodiments, the system may further comprise a light aggregation module configured to (i) combine (a) the one or more light pulses obtained from the one or more laser light beams with (b) at least one of the white light beam or the ICG excitation light beam to generate (c) a combined light beam, and (ii) provide the combined light beam to a scope. The scope may be insertable into the subject's body and configured to direct the combined light beam onto the target region.

In some embodiments, the movable plate may be optically aligned with (i) the one or more laser light sources and (ii) the ICG excitation light source. In some embodiments, the movable plate and the white light source may not share a common optical axis. In some embodiments, the white light beam from the white light source may be transmitted continuously without being affected or separated into pulses by the movable plate. In some embodiments, the one or more light pulses may be obtained from (i) the one or more laser light beams and (ii) the ICG excitation light beam.

In some embodiments, the system may further comprise a light aggregation module configured to (i) combine (a) the one or more light pulses obtained from the one or more laser light beams and the ICG excitation light beam with (b) the white light beam to generate (c) a combined light beam, and (ii) provide the combined light beam to a scope. The scope may be insertable into the subject's body and configured to direct the combined light beam onto the target region.

In some embodiments, the movable plate may be optically aligned with (i) the one or more laser light sources and (ii) the white light source. In some embodiments, the movable plate and the ICG excitation light source may not share a common optical axis. In some embodiments, the ICG excitation light beam from the ICG excitation light source may be transmitted continuously without being affected or separated into pulses by the movable plate. In some embodiments, the one or more light pulses may be obtained from (i) the one or more laser light beams and (ii) the white light beam.

In some embodiments, the system may further comprise a light aggregation module configured to (i) combine (a) the one or more light pulses obtained from the one or more laser light beams and the white light beam with (b) the ICG excitation light beam to generate (c) a combined light beam, and (ii) provide the combined light beam to a scope. The scope may be insertable into the subject's body and configured to direct the combined light beam onto the target region.

In some embodiments, the movable plate may be optically aligned with (i) the one or more laser light sources, (ii) the white light source, and (iii) the ICG excitation light source. In some embodiments, the one or more light pulses may be obtained from (i) the one or more laser light beams, (ii) the white light beam, and (iii) the ICG excitation light beam.

In some embodiments, the system may further comprise a light aggregation module configured to (i) combine (a) the one or more light pulses obtained from the one or more laser light beams with (b) the one or more light pulses obtained from the white light beam and the ICG excitation light beam to generate (c) a combined light beam, and (ii) provide the combined light beam to a scope. The scope may be insertable into the subject's body and configured to direct the combined light beam onto the target region.

In some embodiments, the one or more cut-outs may correspond to one or more open regions disposed on the movable plate. In some embodiments, the one or more open regions may be configured to allow a transmission of light through the movable plate when the one or more cut-outs are aligned with at least one of said plurality of illumination sources.

In some embodiments, the movable plate may be configured to control the exposure of the one or more illumination sources by selectively allowing one or more light beams generated by the one or more illumination sources to pass through the one or more cut-outs of the moveable plate during one or more pre-determined time intervals.

In some embodiments, the one or more light beams may comprise the one or more laser light beams, the white light beam, or the ICG excitation light beam.

In some embodiments, the one or more pre-determined time intervals may be determined based on (i) a rotation speed of the movable plate and (ii) a cut-out geometry associated with the one or more cut-outs.

In some embodiments, at least one of the plurality of illumination sources may be aligned with at least one of the one or more cut-outs during the pre-determined time intervals.

In some embodiments, the one or more open regions may comprise one or more distinct open regions configured to provide one or more distinct exposure times for at least one of the plurality of illumination sources while the movable plate rotates relative to the plurality of illumination sources.

In some embodiments, the one or more open regions may comprise one or more annular-shaped openings disposed at one or more radial distances from a center of the movable plate. In some embodiments, each of the one or more radial distances may correspond respectively to at least one of the plurality of illumination sources.

In some embodiments, the one or more annular-shaped openings may be disposed at one or more distinct angular positions relative to each other. In some embodiments, a first annular-shaped opening of the one or more annular-shaped openings may have a first circumferential length that is different than a second circumferential length of a second annular-shaped opening of the one or more annular-shaped openings.

In some embodiments, the one or more open regions may comprise one or more wedge-shaped opening with a circumferential width that is configured to provide a pre-determined exposure time for each of said plurality of illumination sources. In some embodiments, the one or more wedge-shaped openings may be disposed at one or more distinct angular positions relative to each other. In some embodiments, a first wedge-shaped opening of the one or more wedge-shaped openings may have a first circumferential width that is different than a second circumferential width of a second wedge-shaped opening of the one or more wedge-shaped openings. In some embodiments, the one or more distinct open regions may comprise (i) a first open region configured to expose at least one of the plurality of illumination sources for a first pre-determined time interval, and (ii) a second open region configured to expose at least one of the plurality of illumination sources for a second pre-determined time interval. In some embodiments, the first open region may have a different geometry than the second open region.

In some embodiments, the movable plate may be configured to rotate at a pre-determined rate of rotation such that at least a subset of the plurality of illumination sources is exposed for one or more time intervals corresponding to an imaging period during which an imaging device with the pre-determined frame capture rate is configured to acquire one or more image frames.

In some embodiments, the imaging device may comprise an image sensor or a camera.

In some embodiments, the system may further comprise an additional movable plate configured to rotate relative to the plurality of illumination sources and the movable plate. In some embodiments, the additional movable plate may be configured to rotate at a second rate that is different than a first rate at which the movable plate is configured to rotate. In some embodiments, the additional movable plate may be configured to rotate in a second direction that is different than a first direction in which the movable plate is configured to rotate. In some embodiments, the movable plate may comprise a first set of cut-outs with a different geometry or arrangement than a second set of cut-outs on the additional movable plate.

In some embodiments, the scope may comprise a laparoscope, an endoscope, a borescope, a videoscope, or a fiberscope.

In some embodiments, the one or more light pulses may be provided to the light aggregation module via one or more optical fiber bundles.

In some embodiments, the white light source may be provided in a separate illumination module that is located remote from one or more illumination sources of the plurality of illumination sources.

In some embodiments, the synchronization of the exposure of the one or more illumination sources through the one or more cut-outs relative to the pre-determined frame capture rate may be performed using a timing signal generated using one or more photointerrupters. In some embodiments, the synchronization of the exposure of the one or more illumination sources through the one or more cut-outs relative to the pre-determined frame capture rate may be performed using a timing signal generated by an imaging device.

In another aspect, the present disclosure provides a method for illuminating a target region of a subject. The method may comprise: providing a plurality of illumination sources comprising (i) a white light source configured to generate a white light beam and (ii) one or more laser light sources configured to generate one or more laser light beams; directing one or more light beams generated by the plurality of illumination sources towards a movable plate comprising one or more cut-outs, wherein the movable plate is (i) optically aligned with one or more of the plurality of illumination sources, and (ii) configured to move so as to (a) control an exposure of the one or more illumination sources through the one or more cut-outs, relative to a pre-determined frame capture rate, and (b) generate one or more light pulses based on the controlled exposure of the one or more illumination sources; and providing the one or more light pulses to a light aggregation module, wherein the light aggregation module is configured to (i) combine the one or more light pulses obtained from each of the one or more light beams generated by the plurality of illumination sources to generate a combined light beam, and (ii) provide the combined light beam to a scope, wherein the scope is insertable into the subject's body and configured to direct the combined light beam onto the target region.

In some embodiments, the plurality of illumination sources may further comprise an indocyanine green (ICG) excitation light source configured to generate an ICG excitation light beam.

In another different aspect, the present disclosure provides a system for illuminating a target region of a subject's body. The system may comprise: a plurality of illumination sources comprising at least two of (i) a white light source configured to generate a white light beam and (ii) one or more light emitting diodes (LEDs) or laser light sources configured to generate one or more laser light beams; and a movable plate comprising one or more cut-outs, wherein the movable plate is optically aligned with one or more of the plurality of illumination sources and configured to (i) move relative to the one or more illumination sources and (ii) control a pulsing of the one or more illumination sources in synchronization with a pre-determined frame capture rate.

In some embodiments, the movable plate may be configured to control the pulsing of the one or more illumination sources by adjusting one or more time intervals during which each of the plurality of illumination sources is optically aligned with the one or more cut-outs of the movable plate.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1A:
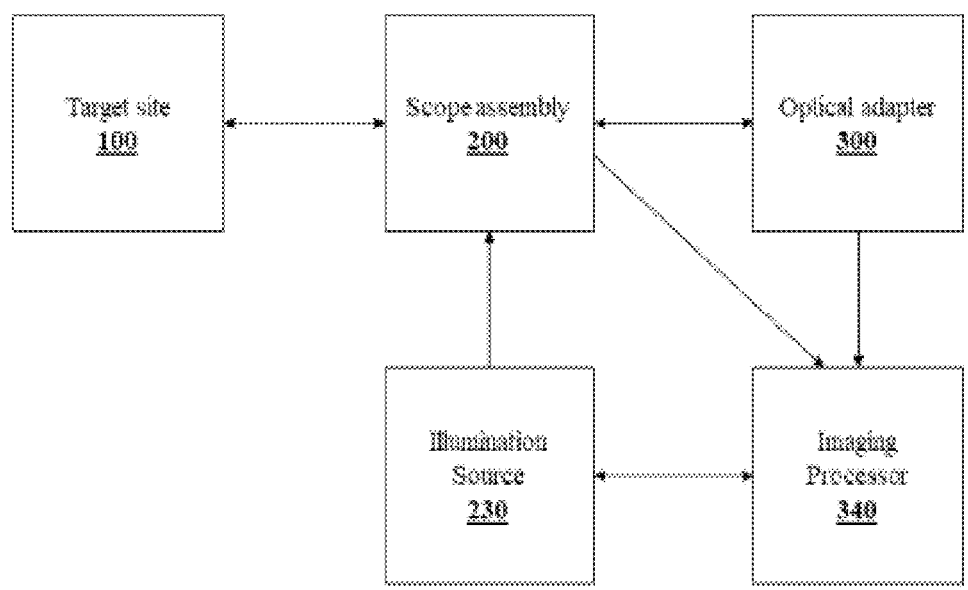
FIG. 1A schematically illustrates a system for medical imaging, in accordance with some embodiments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than" or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "perfusion," as used herein, generally refers to passage of fluid through the circulatory system or lymphatic system to an organ or a tissue. In an example, perfusion may refer to the delivery of blood at the level of the arteries or capillaries, in which exchange of oxygen and/or nutrients between blood and tissue takes place. In some cases, perfusion may comprise flow rate of the fluid, volume of the fluid that is present or traversing across a target tissue site, a pattern of flow channels of the fluid at the target tissue site, or a combination thereof. In some cases, perfusion of the liquid of interest may be increasing, decreasing, or remaining substantially the same during one or more imaging processes. In some cases, any change in flow rate or volume of the perfusing fluid may be indicative of (i) one or more biological events or (ii) one or more surgical events occurring upstream of, downstream of, or substantially at the target tissue site. When quantified, perfusion may be measured as the rate at which blood is delivered to tissue, or volume of blood per unit time (blood flow) per unit tissue mass, in units of cubic meter per second per kilogram ($m^3$/s/kg) or milliliters per minute per grams (mL/min/g). Degree of perfusion may be indicative of one or more health conditions, e.g., cardiovascular disease such as coronary artery disease, cerebrovascular disease, peripheral artery disease, etc.

The term "real time" or "real-time," as used interchangeably herein, generally refers to an event (e.g., an operation, a process, a method, a technique, a computation, a calculation, an analysis, a visualization, an optimization, etc.) that is performed using recently obtained (e.g., collected or received) data. In some cases, a real time event may be performed almost immediately or within a short enough time span, such as within at least 0.0001 millisecond (ms), 0.0005 ms, 0.001 ms, 0.005 ms, 0.01 ms, 0.05 ms, 0.1 ms, 0.5 ms, 1 ms, 5 ms, 0.01 seconds, 0.05 seconds, 0.1 seconds, 0.5 seconds, 1 second, or more. In some cases, a real time event may be performed almost immediately or within a short enough time span, such as within at most 1 second, 0.5 seconds, 0.1 seconds, 0.05 seconds, 0.01 seconds, 5 ms, 1 ms, 0.5 ms, 0.1 ms, 0.05 ms, 0.01 ms, 0.005 ms, 0.001 ms, 0.0005 ms, 0.0001 ms, or less.

Recognized herein are various limitations with medical imaging systems currently available. Conventional medical imaging systems (e.g., a scope such as an endoscope) may use a single light signal (e.g., a white light) to visualize a target site (e.g., an internal portion) within a subject. Such visualization may be limited to two-dimensional representation of the surface of a target site (e.g., a tissue of interest). In some cases, conventional medical procedures may utilize an additional imaging technique or setup to visualize an additional feature of the target site, e.g., internal processes such as perfusion (e.g., blood flow). In an example, one or more dyes (e.g., ICG dyes) may be used in conjunction with endoscopy to visualize blood flow. In another example, a separate laser speckle imaging setup may be used to visualize additional features of the target site, such as the blood flow. However, the additional imaging technique or setup may (i) limit the time frame during which an operator may visualize changes in the additional feature and/or (ii) require additional personnel (e.g., technicians or medical practitioners) on site to manage the components and processes.

The optical adapter of the present disclosure may allow visualization of structures or features (e.g., blood flow) that are in a target site, near a target site, and/or beneath the surface of a target site, which structures or features would ordinarily be invisible to the human eye or other scope assemblies. The optical adapter of the present disclosure may allow visualization of one or more anatomical structures and/or physiological features or functions. The optical adapter of the present disclosure may be used for physiologic, pathologic, morphologic, and/or anatomic visualizations of various structures, features, and/or functions within a subject's body. The optical adapter of the present disclosure may make the invisible, visible. The optical adapter of the present disclosure may help visualize the invisible. The optical adapter, as a single setup with an existing scope assembly (e.g., an endoscope with an off-the-shelf camera), may enable a plurality of different imaging modalities. For example, the optical adapter may provide speckle imaging capabilities as well as photographic images and/or video in a single setup. In such case, the optical adapter may allow users to switch between different visualization modes, e.g., (i) white-light based video only, (ii) laser speckle imaging only, and (iii) both white-light based video and laser speckle imaging.

The optical adapter of the present disclosure may allow visualization of perfusion (e.g., blood perfusion) at a tissue site of interest substantially in real-time, as compared to delayed visualization of perfusion data from dye-based angiography. In an example, a real-time event may comprise visualization of blood perfusion at a tissue site, in which a data set (e.g., one or more light signals) indicative of the blood perfusion is captured by a tool (e.g., an image sensor), and the data is transmitted to a display for visualization to a user. In another example, a real-time event may comprise combining two different data sets that are indicative of different features of the tissue site for a simultaneous visualization at the display.

By enhancing the flexibility and use of existing medical imaging equipment, the optical adapter of the present disclosure may not require or incur expensive capital equipment upgrades in healthcare environments. By replacing existing dye-based imaging systems, the optical adapter of the present disclosure may reduce operating room footprint.

The optical adapter of the present disclosure may be usable for a number of medical applications, e.g., general surgery, neurosurgical procedures, orthopedic procedures, and spinal procedures. The optical adapter of the present disclosure may be applicable to a wide variety of endoscopy-based procedures, including, but are not limited to, cholecystectomy (e.g., 1,200,000 procedures per year), hysterectomy (e.g., 575,000 procedures per year), thyroidectomy (e.g., 150,500 procedures per year), and gastrectomy (e.g., 225,000 procedures per year).

In an aspect, the present disclosure provides an optical adapter for medical imaging. The optical adapter may be configured to be operatively coupled to a scope assembly for medical imaging. The optical adapter may enhance one or more functions (e.g., imaging functions) of the scope assembly. The optical adapter may introduce one or more additional functions (e.g., imaging functions) to the scope assembly. The optical adapter may allow a user (e.g., a medical practitioner such as a physician, nurse practitioner, nurse, imaging specialist, etc.) to visualize and/or analyze a target site of a subject, such as internal tissue of a patient, in one or more ways that any traditional scope assembly alone cannot.

The optical adapter (or at least a portion of the optical adapter) may be reused, and may be interchangeable with different scope assemblies. In some cases, the optical adapter may allow a scope from a first scope assembly to be operatively coupled to a camera of a different scope assembly, to thereby further diversifying imaging modalities of existing scope assemblies.

The scope assembly may be configured to visualize external and/or inner surface of a tissue (e.g., skin or internal organ) of a subject. The scope assembly may be used to (i) examine (e.g., visually examine) the tissue of the subject and (ii) diagnose and/or assist in a medical intervention (e.g., treatments, such as a surgery). In some cases, the scope assembly may be an endoscope. Examples of the endoscope may include, but are not limited to, a cystoscope (bladder), nephroscope (kidney), bronchoscope (bronchus), arthroscope (joints) and colonoscope (colon), and laparoscope (abdomen or pelvis).

The optical adapter may be configured to be operatively coupled to at least 1, 2, 3, 4, 5, or more scope assemblies. The optical adapter may be configured to be operatively coupled to at most 5, 4, 3, 2, or 1 scope assembly. The optical adapter may be disposable and configured for single use in a medical imaging procedure. Alternatively, the optical adapter may be configured to be reusable for a plurality of medical imaging procedures. The plurality of medical imaging procedures may be for the same subject (e.g., the same patient) or for a plurality of different subjects. The optical adapter may be reusable for at least 2, 3, 4, 5, 6, 7, 8, 9, 10, 20, 30, 40, 50, 60, 70, 80, 90, 100, 200, 300, 400, 500, 1,000, or more medical imaging procedures. The optical adapter may be reusable for at most 1,000, 500, 400, 300, 200, 100, 90, 80, 70, 60, 50, 40, 30, 20, 10, 9, 8, 7, 6, 5, 4, 3, or 2 medical imaging procedures. In some cases, the optical adapter may be autoclavable for a sterile subsequent use.

The optical adapter may be configured to receive one or more light signals from the target site of the subject. The optical adapter may be configured to receive at least 1, 2, 3, 4, 5, 6, 7, 8, 9, 10, or more light signals from the target site. The optical adapter may be configured to receive at most 10, 9, 8, 7, 6, 5, 4, 3, 2, or 1 light signal from the target site. The one or more light signals may be reflected or emitted from the target site upon exposure or illumination of the target site to an optical beam. In some examples, a natural tissue of the target site or one or more dyes introduced to the target site may be responsible for reflecting or emitting the one or more light signals. Alternatively or in addition to, the one or more light signals may be emitted by the target site in absence of any exposure to an optical beam. In an example, the target site may emit at least a portion of the electromagnetic spectrum, such as infrared radiation.

Infrared radiation emission by the target site may range from the red edge of the visible spectrum at a wavelength of about 700 nanometers (nm) to about 1 millimeters (mm), which is approximately equivalent to a frequency of about 430 terahertz (THz) to about 300 gigahertz (GHz). Regions within the infrared spectrum may include, for example, near-infrared (NIR), short-wavelength infrared (SWIR), mid-wavelength infrared (MWIR), intermediate infrared (IIR), long-wavelength infrared (LWIR), and far-infrared (FIR). Near-infrared signal may range from about 0.7 micrometer (μm) to about 1.4 μm, which is approximately equivalent to a frequency of about 214 THz to about 400 THz. Long-wavelength infrared may range from about 8 μm to about 15 μm, which is approximately equivalent to a frequency of about 20 THz to about 37 THz.

The optical beam may comprise a single light beam from a single light source. Alternatively, the optical beam may be a combined light beam comprising a plurality of light beams. In some cases, the plurality of light beams may be directed to the target site from the same direction. Alternatively, the plurality of light beams may be directed to the target site from different directions. In some cases, the plurality of light beams may comprise (i) a white light and (ii) one or more laser beams. The plurality of light beams may be directed from a single optical source or a plurality of optical sources. The one or more laser beams may include at least 1, 2, 3, 4, 5, 6, 7, 8, 9, 10, or more laser beams. The one or more laser beams may include at most 10, 9, 8, 7, 6, 5, 4, 3, 2, or 1 laser beam.

Laser beams of varying wavelengths may be selected based on a desired penetration depth of the tissue site. Alternatively or in addition to, laser beams of varying wavelengths may be selected based on a composition of interest (e.g., one or more molecules, compounds, or chemicals) present or expected to be present at the tissue site. In an example, a first laser beam having a first wavelength may be selected for detecting oxygenated blood, whereas a second laser beam having a second wavelength may be selected for detecting de-oxygenated blood. A user of the subject systems and methods provided herein may be able to select one or more laser wavelengths of interest depending on such parameters of the tissue site.

The scope assembly may comprise a scope and a camera. The scope and the camera may be operatively coupled to each other, e.g., electronically or mechanically. The scope and the camera may be releasably coupled to each other. The scope may be configured to (1) receive a light beam from an illumination source and (2) direct the light beam onto the target site of the subject's body. In some cases, the scope may be configured to (1) receive a combined light beam from the illumination source and (2) direct the combined light beam onto the target site within the subject's body.

The optical adapter may comprise a housing that comprises a first end and a second end. The first end may be configured to couple to a scope of the scope assembly. The second end may be configured to couple to the camera of the scope assembly. Any one of the subject couplings of the present disclosure may utilize one or more coupling mechanisms, such as, for example, magnets (e.g., electromagnet or permanent magnet), mechanical tethers (e.g., string or thread tethers), adhesives (e.g., solids, semi-solids, gels, viscous liquids, etc.), male-to-female fasteners (e.g., mating or interlocking fasteners, hooks and holes, hooks and loops such as Velcro™, a female nut threaded onto a male bolt, a male protrusion inserted into a female indentation in LEGO blocks, a male threaded pipe fitted into a female threaded elbow in plumbing, a male universal serial bus (USB) plug inserted into a female USB socket, etc.), screw-on coupling (e.g., with or without a coaxial connector), elastic coupling, gear coupling, hydrodynamic coupling, and other gasping mechanisms such as robotic arms that hold two or more components operatively relative to each other. In some cases, the coupling (i) between the first end of the housing and the scope and/or (ii) between the second end of the housing and the camera may be reversible or irreversible. In some examples, the coupling may be a releasable coupling.

In some cases, the first end of the housing may be configured to releasably couple to the scope using a quick release mechanism (e.g., snap-fit, latches, etc.). The quick release mechanism may be configured to releasably couple the optical adapter to various types of scopes having different sizes. In an example, the first end may comprise different sections with varied dimensions (e.g., different radial dimensions) configured to releasably coupled to different scopes having different sizes. In another example, the first end may comprise an adjustable aperture mechanism with adjustable aperture diameter to accommodate different scopes having different sizes. The quick release mechanism may be configured to quickly move between a lock position (i.e., a coupled position) and a release position (i.e., a non-coupled position) in response to one or more movements of the quick release mechanism, such as a single, non-repetitious movement (e.g., lateral or rotational) of the quick release mechanism. The quick release mechanism may be configured to quickly move between a lock and a release position in response to a user instruction via a switch, e.g., a mechanical switch disposed on the optical adapter or the scope.

The quick release mechanism may be configured to permit the user to releasably couple the first end of the housing to the scope without use of tools. Alternatively, the quick release mechanism may be configured to permit the user to releasably couple the first end of the housing to the scope with one or more tools, e.g., one or more keys to operatively coupled to the quick release mechanism to activate release of the quick release mechanism. The quick release mechanism may be configured to permit the user to releasably couple the first end of the housing to the scope in less than 60 seconds. The quick release mechanism may be configured to permit the user to releasably couple the first end of the housing to the scope in less than 60 seconds, 55 seconds, 50 seconds, 45 seconds, 40 seconds, 35 seconds, 30 seconds, 25 seconds, 20 seconds, 15 seconds, 10 seconds, 5 seconds, or less.

In some cases, the coupling between the first end of the housing and the scope may not utilize a quick release mechanism. In some cases, the scope may be screwed on to the first end of the housing, thereby preventing a quick release of the scope from the first end of the housing. In an example, a coupling surface of the first end of the housing may substantially mimic the structure of a coupling surface of the camera, wherein the coupling surface of the camera is originally configured to couple to the scope.

In some cases, the second end of the housing may be configured to releasably couple to the camera of the scope assembly using a quick release mechanism (e.g., snap-fit, latches, etc.). The quick release mechanism may be configured to releasably couple the optical adapter to various types of cameras having different sizes. In an example, the second end may comprise different sections with varied dimensions (e.g., different radial dimensions) configured to releasably coupled to different cameras having different sizes. In another example, the second end may comprise an adjustable aperture mechanism with adjustable aperture diameter to accommodate different cameras having different sizes. The quick release mechanism may be configured to quickly move between a lock position (i.e., a coupled position) and a release position (i.e., a non-coupled position) in response to one or more movements of the quick release mechanism, such as a single, non-repetitious movement (e.g., lateral or rotational) of the quick release mechanism. The quick release mechanism may be configured to quickly move between a lock and a release position in response to a user instruction via a switch, e.g., a mechanical switch disposed on the optical adapter or the camera.

The quick release mechanism may allow for precise coupling of two members, such as (i) the first end of the housing and the scope or (ii) the second end of the housing and the camera. The precise coupling may provide an optimal optical path between the two members. The precise coupling may be achieved within an accuracy of less than about 20 μm. In some cases, the precise coupling may be achieved within an accuracy of at most about 100 μm, 90 μm, 80 μm, 70 μm, 60 μm, 50 μm, 40 μm, 30 μm, 20 μm, 10 μm, 9 μm, 8 μm, 7 μm, 6 μm, 5 μm, μm, 3 μm, 2 μm, 1 μm, 900 nm, 800 nm, 700 nm, 600 nm, 500 nm, 400 nm, 300 nm, 200 nm, 100 nm, 50 nm, or less.

The quick release mechanism may be configured to permit the user to releasably couple the second end of the housing to the camera without use of tools. Alternatively, the quick release mechanism may be configured to permit the user to releasably couple the second end of the housing to the camera with one or more tools, e.g., one or more keys to operatively coupled to the quick release mechanism to activate release of the quick release mechanism. The quick release mechanism may be configured to permit the user to releasably couple the second end of the housing to the camera in less than 60 seconds. The quick release mechanism may be configured to permit the user to releasably couple the second end of the housing to the camera in less than 60 seconds, 55 seconds, 50 seconds, 45 seconds, 40 seconds, 35 seconds, 30 seconds, 25 seconds, 20 seconds, 15 seconds, 10 seconds, 5 seconds, or less.

In some cases, the coupling between the second end of the housing and the camera may not utilize a quick release mechanism. In some cases, the camera may be screwed on to the second end of the housing, thereby preventing a quick release of the camera from the second end of the housing. In an example, a coupling surface of the second end of the housing may substantially mimic the structure of a coupling surface of the scope, wherein the coupling surface of the scope is originally configured to couple to the camera.

The housing may include one or more biologically acceptable and/or compatible materials suitable for medical applications, depending on the particular application and/or preference of a medical practitioner. For example, components of the housing may include or be fabricated from materials such as polyvinyl chloride, polyvinylidene chloride, low density polyethylene, linear low density polyethylene, polyisobutene, poly(ethylene-vinylacetate) copolymer, lightweight aluminum foil and combinations thereof, stainless steel alloys, commercially pure titanium, titanium alloys, silver alloys, copper alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, glass, and combinations thereof.

At least a portion of the housing may be opaque, semi-transparent, or transparent. In some cases, the housing may be opaque and configured to block any external light from (i) entering through the housing into one or more components within the housing and (ii) interfering with the one or more light signals from the target site of the subject that is received by the optical adapter.

Pressure inside the housing of the optical adapter may be approximately the same as ambient pressure (e.g., atmospheric pressure). Alternatively, the pressure inside the housing may be controlled (or regulated, e.g., manually or automatically) such that the inner pressure of the housing is lower or higher than the ambient pressure. Temperature inside the housing of the optical adapter may be approximately the same as ambient temperature (e.g., room temperature). Alternatively, the temperature inside the housing may be controlled (or regulated, e.g., manually or automatically) such that the inner temperature of the housing is lower or higher than the ambient temperature. Humidity inside the housing of the optical adapter may be approximately the same as ambient humidity. Alternatively, the humidity inside the housing may be controlled (or regulated, e.g., manually or automatically) such that the inner humidity of the housing is lower or higher than the ambient humidity. In some examples, the pressure, temperature, and/or humidity of the optical adapter may be regulated for optimal function of the optical adapter.

The first end of the housing and the scope may be coupled directly to each other. Alternatively, the first end of the housing and the scope may be operatively coupled to each other via one or more couplers. The second end of the housing and the camera may be coupled directly to each other. Alternatively, the second end of the housing and the camera may be operatively coupled to each other via one or more couplers (e.g., a coupling ring). In some cases, a first end of a coupler may be configured to couple (e.g., releasably couple) to the scope, and a second end of the coupler may be configured to couple (e.g., releasably couple) to the first end of the housing. In some cases, a first end of a coupler may be configured to couple (e.g., releasably couple) to the camera, and a second end of the coupler may be configured to couple (e.g., releasably couple) to the second end of the housing.

The first end and the second end of the housing may share a common longitudinal axis. In some cases, the first end and the second end may be provided on opposite sides of the housing. In such cases, once the optical adapter is operatively coupled to the scope assembly, the scope and the camera of the scope assembly may be disposed on opposite sides of the housing of the optical adapter. Alternatively, the first end and the second end of the housing may not share a common longitudinal axis. In such case, the first end and the second end may be provided on orthogonal sides of the housing.

The optical adapter may comprise one or more sensors. The optical adapter may comprise at least 1, 2, 3, 4, 5, or more sensors. The optical sensor may comprise at most 5, 4, 3, 2, or 1 sensor. Examples of the one or more sensors may include, but are not limited to, pressure sensor, temperature sensor, optical sensor (e.g., image sensor), gas composition sensor, membrane or diaphragm sensor, thin film sensor, resistive or capacitive sensor, or other type of sensing device. The one or more sensors may be permanently coupled to the optical adapter or, alternatively, removable from the optical adapter.

In some cases, the optical adapter may comprise an image sensor. The image sensor may be a part of the optical adapter. The image sensor may be permanently coupled to the optical adapter or, alternatively, removable from the optical adapter. In an example, the image sensor may be configured to releasably couple to the housing of the optical adapter. The image sensor may be configured to releasably couple to a surface of the housing, and the surface may be substantially orthogonal to the first end and/or the second end of the housing. In such a case, the image sensor may comprise a casing that is configured to releasably couple to the surface of the housing. Alternatively, the surface may not be substantially orthogonal to the first end and/or the second end of the housing. The image sensor may be coupled (e.g., releasably coupled) to the housing using one or more of the abovementioned coupling mechanisms.

The image sensor may be disposable and configured for single use in a medical imaging procedure. Alternatively, the image sensor may be configured to be reusable for a plurality of medical imaging procedures. The plurality of medical imaging procedures may be for the same subject (e.g., the same patient) or for a plurality of different subjects. The image sensor may be reusable for at least 2, 3, 4, 5, 6, 7, 8, 9, 10, 20, 30, 40, 50, 60, 70, 80, 90, 100, 200, 300, 400, 500, 1,000, or more medical imaging procedures. The image sensor may be reusable for at most 1,000, 500, 400, 300, 200, 100, 90, 80, 70, 60, 50, 40, 30, 20, 10, 9, 8, 7, 6, 5, 4, 3, or 2 medical imaging procedures. In some cases, the image sensor may be autoclavable for a sterile subsequent use.

The image sensor may be configured to receive a light signal from the target site of the subject for analysis and/or visualization of the target site of the subject. Such light signal may be reflected or emitted from the target site. The image sensor may be configured to detect the light signal from the target site and transform the detected light signal to generate an image indicative of the target tissue. The generated image may be one-dimensional or multi-dimensional (e.g., two-dimensional, three-dimensional, etc.). Alternatively, the image sensor may be operatively coupled to a processor. In such case, the image sensor may be configured to detect the light signal from the target site and convert the detected light signal into a digital signal. The image sensor may further be configured to transmit the digital signal to the processor that is capable of generating an image indicative of the target tissue.

Examples of the image sensor may include, but are not limited to, a charge coupled device (CCD), metal oxide semiconductor (MOS) (e.g., complementary MOS, i.e., CMOS), modifications thereof, functional variants thereof, and modifications thereof. The optical adapter may comprise at least 1, 2, 3, 4, 5, or more image sensors. The optical adapter may comprise at most 5, 4, 3, 2, or 1 image sensor.

The casing of the image sensor may include one or more biologically acceptable and/or compatible materials suitable for medical applications, depending on the particular application and/or preference of a medical practitioner. For example, components of the casing may include or be fabricated from materials such as polyvinyl chloride, polyvinylidene chloride, low density polyethylene, linear low density polyethylene, polyisobutene, poly(ethylene-vinylacetate) copolymer, lightweight aluminum foil and combinations thereof, stainless steel alloys, commercially pure titanium, titanium alloys, silver alloys, copper alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, glass, and combinations thereof. The housing of the optical adapter and the casing of the image sensor may be comprised of the same or different materials.

At least a portion of the casing may be opaque, semitransparent, or transparent. In some cases, the casing may be opaque and configured to block any external light from (i) entering through the casing into one or more components within the casing (e.g., an imaging sensing mechanism of the image sensor such as CCD or CMOS) and (ii) interfering with the one or more light signals directed from the target site of the subject and toward the image sensor.

The image sensor and the camera may have different optical axes. An optical axis of the image sensor and an optical axis of the camera may intersect at an angle of at least 1 degree, 2 degrees, 3 degrees, 4 degrees, 5 degrees, 6 degrees, 7 degrees, 8 degrees, 9 degrees, 10 degrees, 20 degrees, 30 degrees, 40 degrees, 50 degrees, 60 degrees, 70 degrees, 80 degrees, 90 degrees, or more. The optical axis of the image sensor and the optical axis of the camera may intersect at an angle of at most 90 degrees, 80 degrees, 70 degrees, 60 degrees, 50 degrees, 40 degrees, 30 degrees, 20 degrees, 10 degrees, 9 degrees, 8 degrees, 7 degrees, 6 degrees, 5 degrees, 4 degrees, 3 degrees, 2 degrees, 1 degree, or less. In an example, the optical axis of the image sensor may be orthogonal to the optical axis of the camera. Alternatively, the image sensor and the camera may have parallel but different longitudinal optical axes.

The optical adapter may comprise an optics assembly disposed in the housing. The optics assembly may be configured to receive light signals from the target site and transmitted through the scope. In an example, the light signals may be reflected from the target site within the subject's body. The optics assembly may further be configured to reflect a first portion of the light signals onto one of the image sensor and the camera, while permitting a second portion of the light signals to pass through to the other of the image sensor and the camera. In an example, the optics assembly (e.g., comprising a shortpass dichroic mirror) may be configured to reflect a first portion of the light signals onto the image sensor, while permitting a second portion of the light signals to pass through to the camera. In another example, the optics assembly (e.g., comprising a longpass dichroic mirror) may be configured to reflect a first portion of the light signals onto the camera, while permitting a second portion of the light signals to pass through to the image sensor.

The first portion of the light signals may comprise deflected light (e.g., backscattered light) that is generated when the target site is illuminated with laser light (e.g., coherent laser light). In some cases, the coherent laser light may be transmitted toward the target site via the scope of the scope assembly. The coherent laser light may be provided from a single laser source configured to emit a coherent laser light having a single wavelength. Non-limiting examples of the single laser source may include a single mode laser, a laser diode with a volume-holographic grating (VHG), or a laser with a laser clean-up filter (e.g., for narrow bandpass). The coherent laser light may be provided from a plurality of laser sources having a plurality of different wavelengths. The plurality of different wavelengths may lie in an invisible spectrum. The invisible spectrum may comprise wavelengths (i) greater than about 700 nm and/or (ii) less than about 400 nm. In some cases, the invisible spectrum may comprise wavelengths (i) greater than about 770 nm and/or (ii) less than about 390 nm. The second portion of the light signals may comprise reflected light that is generated when the target site is illuminated with a different light (e.g., white light). In some cases, the different light may be a white light comprising a plurality of wavelengths in the visible spectrum, comprising wavelengths between about 400 nm to about 700 nm. In some cases, the white light may be transmitted toward the target site via the scope. In some examples, the scope may comprise a plurality of optical paths to direct the coherent laser light and the white light separately from each other. In some examples, the scope may comprise a single optical path to direct a combined light that comprises both the coherent laser light and the white light.

In some cases, the optics assembly may comprise a beam splitter. The beam splitter may be configured to receive light signals from the target site and (i) reflect the first portion of the light signals that is in a first electromagnetic spectral range toward the image sensor, and (ii) permit the second portion of the light signals in a second electromagnetic spectral range to pass through toward the camera of the scope assembly. Alternatively, the beam splitter may be configured to receive light signals from the target site and (i) reflect the second portion of the light signals that is in the second electromagnetic spectral range toward the camera of the scope assembly, and (ii) permit the first portion of the light signals in the first electromagnetic spectral range to pass through toward the image sensor. Examples of the beam splitter may include, but are not limited to, a half mirror, a dichroic beam splitter (e.g., a shortpass or longpass dichroic mirror), or a multi-band beam splitter. In an example, the beam splitter may be a cube comprising two prisms (e.g., two triangular glass prisms) disposed adjacent to each other.

The first and second electromagnetic spectral ranges may be different. In some cases, the first portion of the light signals may comprise one or more wavelengths from an invisible electromagnetic spectrum. The invisible electromagnetic spectrum may comprise one or more wavelengths from about 700 nm (or 0.7 μm) to about 1 mm (or 1000 μm). Alternatively or in addition to, the invisible electromagnetic spectrum may comprise one or more wavelengths lower than 400 nm. In some cases, the second portion of the light signals may comprise one or more wavelengths from a visible electromagnetic spectrum, ranging from about 400 nm (or 0.4 μm) to about 700 nm (or 0.7 μm).

The first portion of the light signals may comprise one or more wavelengths from about 0.7 μm to about 1,000 μm. The first portion of the light signals may comprise one or more wavelengths from at least about 0.7 μm. The first portion of the light signals may comprise one or more wavelengths from at most about 1,000 μm. The first portion of the light signals may comprise one or more wavelengths from about 0.7 μm to about 1 μm, about 0.7 μm to about 5 μm, about 0.7 μm to about 10 μm, about 0.7 μm to about 50 μm, about 0.7 μm to about 100 μm, about 0.7 μm to about 500 μm, about 0.7 μm to about 1,000 μm, about 1 μm to about 5 μm, about 1 μm to about 10 μm, about 1 μm to about 50 μm, about 1 μm to about 100 μm, about 1 μm to about 500 μm, about 1 μm to about 1,000 μm, about 5 μm to about 10 μm, about 5 μm to about 50 μm, about 5 μm to about 100 μm, about 5 μm to about 500 μm, about 5 μm to about 1,000 μm, about 10 μm to about 50 μm, about 10 μm to about 100 μm, about 10 μm to about 500 μm, about 10 μm to about 1,000 μm, about 50 μm to about 100 μm, about 50 μm to about 500 μm, about 50 μm to about 1,000 μm, about 100 μm to about 500 μm, about 100 μm to about 1,000 μm, or about 500 μm to about 1,000 μm. The first portion of the light signals may comprise one or more wavelengths from about 0.7 μm, about 1 μm, about 5 μm, about 10 μm, about 50 μm, about 100 μm, about 500 μm, or about 1,000 μm.

The second portion of the light signals may comprise one or more wavelengths from about 400 nm to about 700 nm. The second portion of the light signals may comprise one or more wavelengths from at least about 400 nm. The second portion of the light signals may comprise one or more wavelengths from at most about 700 nm. The second portion of the light signals may comprise one or more wavelengths from about 400 nm to about 450 nm, about 400 nm to about 500 nm, about 400 nm to about 550 nm, about 400 nm to about 600 nm, about 400 nm to about 650 nm, about 400 nm to about 700 nm, about 450 nm to about 500 nm, about 450 nm to about 550 nm, about 450 nm to about 600 nm, about 450 nm to about 650 nm, about 450 nm to about 700 nm, about 500 nm to about 550 nm, about 500 nm to about 600 nm, about 500 nm to about 650 nm, about 500 nm to about 700 nm, about 550 nm to about 600 nm, about 550 nm to about 650 nm, about 550 nm to about 700 nm, about 600 nm to about 650 nm, about 600 nm to about 700 nm, or about 650 nm to about 700 nm. The second portion of the light signals may comprise one or more wavelengths from about 400 nm, about 450 nm, about 500 nm, about 550 nm, about 600 nm, about 650 nm, or about 700 nm.

In some cases, the beam splitter may be a polarizing beam splitter, e.g., a Wollaston prism. The polarizing beam splitter may be configured to receive light signals from the target site and (i) reflect the first portion of the light signals that is in first polarization toward the image sensor, and (ii) permit the second portion of the light signals in second polarization to pass through toward the camera of the scope assembly.

The optics assembly may not comprise any focusing device (e.g., an optical aperture, such as an objective lens) ahead of the beam splitter (e.g., before the light signals reach the beam splitter). Alternatively, the optics assembly may comprise one or more focusing devices ahead of the beam splitter. The optics assembly may comprise at least 1, 2, 3, 4, 5, or more focusing devices disposed ahead of the beam splitter. The optics assembly may comprise at most 5, 4, 3, 2, or 1 focusing device disposed ahead of the beam splitter.

In some cases, the image sensor may be configured to generate a first set of imaging data from the first portion of the light signals, and the camera may be configured to generate a second set of imaging data from the second portion of the light signals. The first set of imaging data and the second set of imaging data may be the same. In an example, the first and second set of imaging data may be the same in order to confirm validity of the collected data. Alternatively, the first and second set of imaging data may be different, e.g., may represent different features of the target site. The first set of imaging data may complement the second set of imaging data. In an example, the image sensor of the optical adapter may be used for laser speckle imaging. In such a case, the first set of imaging data may comprise one or more laser speckle patterns, and the second set of imaging data may comprise one or more photographic and/or video images. The first set of imaging data may comprise at least 1, 2, 3, 4, 5, 6, 7, 8, 9, 10, or more laser speckle patterns. The first set of imaging data may comprise at most 10, 9, 8, 7, 6, 5, 4, 3, 2, orl laser speckle pattern.

Examples of features of the target site that may be detected by the image sensor and recorded in the first set of imaging data may include, but are not limited to, temperature, surface depth (i.e., tomography), blood flow rate, oxygen concentration (e.g., in the blood), calcium potential, electrical potential, magnetic field, presence of one or more markers of interest (e.g., immunological staining), etc.

A focusing device, as used herein in the present disclosure, may comprise any lens (e.g., fish-eye, elliptical, conical, etc.), reflector, optic, concentrator, or other device that is capable of reflecting or focusing light. In an example, the focusing device may be a relay lens. The optics assembly may comprise at least one focusing device (e.g., at least 1, 2, 3, 4, 5, or more focusing devices) for the image sensor. The at least one focusing device may be disposed between the beam splitter and the image sensor. The optics assembly may comprise at least one focusing device (e.g., at least 1, 2, 3, 4, 5, or more focusing devices) for the camera. The at least one focusing device may be disposed between the beam splitter and the camera. In some cases, the optics assembly may comprise at least one focusing device (e.g., at least 1, 2, 3, 4, 5, or more focusing devices) disposed in the optical path between the scope and the beam splitter.

In some cases, the optics assembly may comprise (i) a first focusing device for the image sensor and (ii) a second focusing device for the camera. The first focusing device may be operatively coupled to a first focusing knob to adjust degree of focusing of the first focusing device. The first focusing knob may be operatively coupled (e.g., electronically or mechanically coupled) to the first focusing device. In an example, the first focusing knob may be mechanically coupled to the first focusing device via a first gearing mechanism comprising one or more gears. The first focusing knob may be operable by the user to adjust focusing of the first focusing device. The second focusing device may be operatively coupled to a second focusing knob to adjust degree of focusing of the second focusing device. The second focusing knob may be operatively coupled (e.g., electronically or mechanically coupled) to the second focusing device. In an example, the second focusing knob may be mechanically coupled to the second focusing device via a second gearing mechanism comprising one or more gears. The second focusing knob may be operable by the user to adjust focusing of the second focusing device.

In some cases, the first focusing device and the second focusing device may be operably coupled to each other (e.g., electronically or mechanically), such that focusing for the image sensor and for the camera can be performed concurrently. In an example, first and second focusing devices may be coupled to each other via a gearing mechanism comprising one or more gears. The first and second focusing devices may be coupled to a common focusing knob that is operable by the user. Alternatively, the first focusing device may be operatively coupled to a first focusing knob, the second focusing device may be operatively coupled to a second focusing knob, and the first and second focusing knobs may be operatively coupled to each other. In such case, (i) operating the first focusing knob may adjust degree of focusing of both the first and second focusing devices, and (ii) operating the second focusing knob may adjust degree of focusing of both the first and second focusing devices.

In some cases, the first focusing device and the second focusing device may not be operably coupled to each other. The first focusing device and the second focusing device may be provided separately and configured to be used independently of each other.

The at least one focusing device may be manually adjusted for focusing. In some cases, one or both of the first focusing device and the second focusing device may be manually adjusted for focusing. Alternatively, the at least one focusing device may be automatically adjusted for focusing. In some cases, the optics assembly may be capable of autofocusing the at least one focusing device. In some cases, one or both of the first focusing device and the second focusing device may be automatically adjusted for focusing. In an example, focusing the first focusing device (e.g., manually or automatically) may consequently autofocus the second focusing device, or vice versa. In another example, the first and second focusing devices may be autofocused simultaneously.

In some cases, the optics assembly of the housing may comprise at least one focusing device for the image sensor and no focusing device for the camera. In such case, the camera may have its own focusing device. The at least one focusing device of the optics assembly and the focusing device of the camera may or may not be operatively coupled to each other.

In some cases, a processor (or a computer) may be operatively linked to the image sensor and the camera. The processor may be configured to direct the image sensor to capture a first set of imaging data and direct the camera to capture a second set of imaging data. The processor may be configured to compare the first set and second set of imaging data. Based at least in part on the comparison, the processor may be configured to direct one or more focusing devices that are operatively coupled to the image sensor and/or the camera to adjust alignment of the image sensor with respect to the camera. Such calibration of the image sensor and/or the camera may improve alignment between an image of the first set of imaging data to another image of the second set of the imaging data. The calibration may be performed by the processor (e.g., upon user instruction or automatically) (i) prior to use of the optical adapter for imaging the target site and/or (ii) in real time during the imaging of the target site.

In some cases, a perspective (i.e., field of view) of the image sensor and a perspective (i.e., field of view) of the camera may be aligned with respect to each other. The processor may be configured to direct the image sensor to capture a first set of imaging data (e.g., based on reflected infrared light or laser light from a target site) and direct the camera to capture a second set of imaging data (e.g., based on reflected white light from the target site). The processor may be further configured to spatially (and/or temporally) align the first set and the second set of imaging data. In an example, the processor may perform digital image processing on one or both of the first set and the second set of imaging data (e.g., affine transformation of one or more pixels of the first set and the second set of imaging data), such that the perspectives of the image sensor and the camera are aligned (or lined up) and spatially correspond to each other. Such alignment of the two imaging units may be useful when creating an overlay of the first set and the second set of imaging data, e.g., when generating an overlay of blood flow and perfusion (e.g., from the image sensor) on top of the standard white light surgical view (e.g., from the camera). In other examples, the processor may be configured to perform image registration. The processor may be configured to find one or more matching features in the first set and the second set of imaging data, then calculate a transformation of one or both of the first set and the second set of imaging data for their alignment. Non-limiting examples of such features include corners, lines, speeded up robust features (SURF), and scale-invariant feature transformation (SIFT) features.

FIG. 1A schematically illustrates an example ecosystem for medical imaging. The ecosystem may comprise a target site 100 of a subject (e.g., a tissue site of interest of a patient). The ecosystem may comprise a scope assembly 200. The ecosystem may comprise an illumination source 230 in optical communication with the scope assembly 200. The illumination source 230 may be configured to provide one or more light beams (e.g., a combined light beam) via the scope assembly 200 and toward the target site 100. The target site 100 may be in optical communication with the scope assembly 200, such that (i) the target site 100 may be illuminated by the one or more light beams from the scope assembly 200 and (ii) the scope assembly 200 may detect one or more light signals reflected or emitted by the target site 100 upon such illumination. The scope assembly 200 may be configured to capture at least one image or video of the target site based on at least a portion of the one or more light signals from the target site 100. The ecosystem may comprise an optical adapter 300 that is operatively coupled to one or more components of the scope assembly 200. The optical adapter 300 may be in optical communication with the scope assembly 200, such that (i) the optical adapter 300 may receive one or more light signals from the scope assembly 200 and (ii) the scope assembly 200 may receive one or more light signals from the optical adapter 300. The optical adapter 300 may be configured to generate data (e.g., images, videos, lase speckle imaging, etc.) based on at least an additional portion of the one or more light signals from the target site 100. The generated data may encode different features of the target site than that of the at least one image or video captured by the scope assembly 200. The scope assembly 200 and the optical adapter 300 may be operatively coupled to an imaging processor 340. The imaging processor 340 may be configured to analyze or combine data, image(s), or video(s) generated by the scope assembly 200 and the optical adapter 300.

Figure 1B:
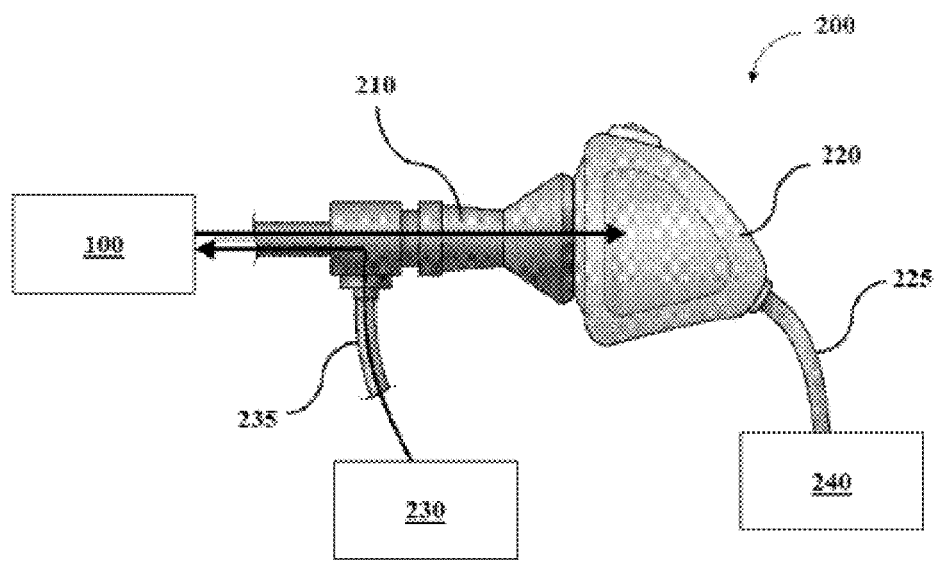
FIG. 1B schematically illustrates a scope assembly, in accordance with some embodiments.

FIG. 1B schematically illustrates an example ecosystem of the scope assembly 200 in absence of the optical adapter 300. The scope assembly 200 comprises a scope 210 and a camera 220 that are operatively coupled to each other. The scope 210 and the camera 220 may me mechanically and optically in communication with each other. The scope 210 may be in optical communication with the illumination source 230 via an optical signal path 235 (e.g., an optical fiber). The illumination source 230 may direct one or more light beams via the optical signal path 235 and to the scope 210, and the scope 210 may direct the one or more light beams toward the target site 100. The scope 210 may also serve as an optical signal path for any light signals reflected or emitted by the target site 100 toward the camera 220. The camera 220 may be operatively coupled to the imaging processor 340 via a signal line 225 (e.g., electrical wire such as copper wire, optical fiber, etc.). In some cases, a focusing coupler may be disposed between the scope 210 and the camera 220. The focusing coupler may be permanently attached to the camera 220. The focusing coupler may comprise a focusing knob.

Figure 2A:
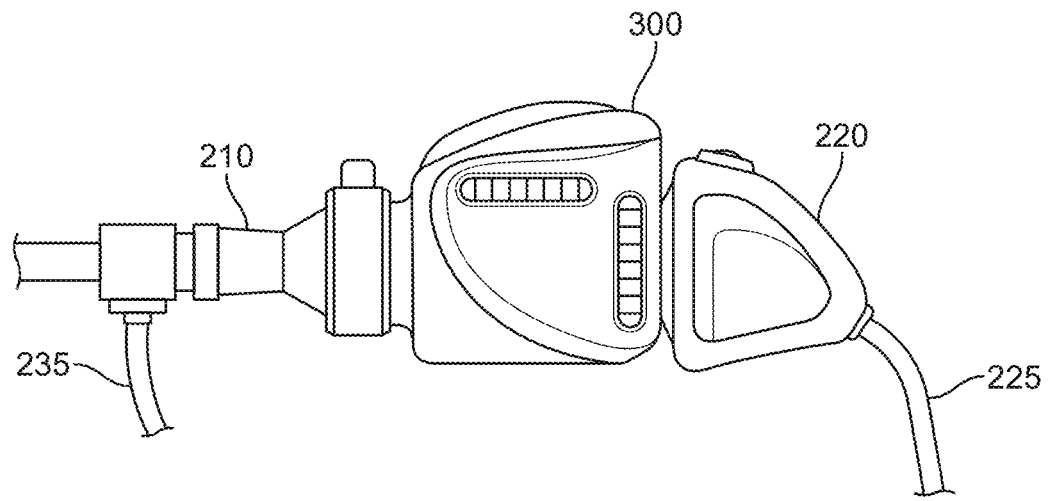
FIGS. 2A, 2B, 2C, and 2D schematically illustrate examples of an optical adapter operatively coupled to a scope assembly, in accordance with some embodiments.
Figure 2B:
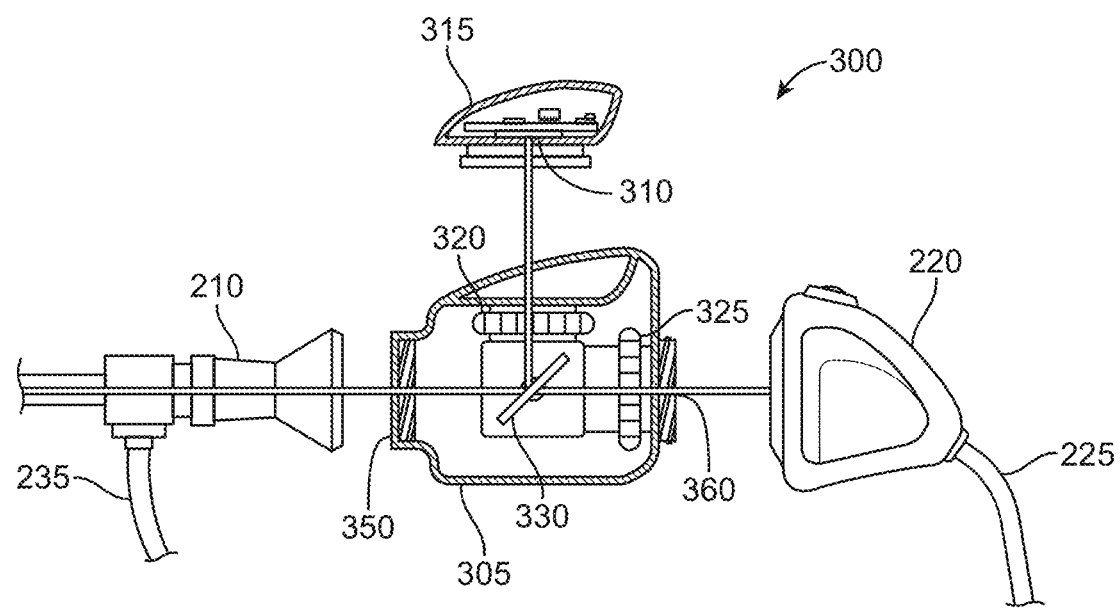

FIGS. 2A and 2B schematically illustrates an embodiment of the ecosystem shown in FIG. 1A, wherein the optical adapter 300 that is operatively coupled to the scope assembly 200. FIG. 2A schematically illustrates a side view of the optical adapter 300, while FIG. 2B schematically illustrates a cross-sectional view of the optical adapter 300. The optical adapter 300 may comprise a housing 305. The housing 305 may comprise a first end 350 configured to releasably couple to the scope 210. The housing 305 may comprise a second end 360 configured to releasably couple to the camera 220. The housing 305 may comprise an image sensor 310 within a casing 315. The image sensor 310 (e.g., the casing 315 comprising the image sensor 310) may be configured to releasably couple to the housing 305.

Referring to FIG. 2B, the housing 305 may comprise an optics assembly 330 disposed in the housing 305. The optics assembly 330 may be configured to (1) receive light signals that are reflected from a target site 100 within a subject's body and transmitted through the scope 210, and (2) reflect a first portion of the light signals onto the image sensor 310 while permitting a second portion of the light signals to pass through and toward to the camera 220. The optics assembly 330 may comprise a beam splitter, such as, for example, a dichroic mirror. The housing 305 may comprise a first focusing device (e.g., lens) disposed between the optics assembly 330 and the image sensor 310, which first focusing device being configured to focus the first portion of the light signals traveling from the optics assembly 330 and toward the image sensor 310. The housing 305 may further comprise a first focusing knob 320 configured to adjust degree of focusing of the first focusing device. The housing 305 may comprise a second focusing device (e.g., lens) disposed between the optics assembly 330 and the camera 220, which second focusing device being configured to focus the second portion of the light signals traveling from the optics assembly 330 and toward the camera 220. The housing 305 may further comprise a second focusing knob 325 configured to adjust degree of focusing of the second focusing device. The first focusing knob 320 and the second focusing knob 325 may be operatively coupled to each other, thus operate in conjunction with each other. In an example, operating the first focusing knob 320 to focus the first focusing device may automatically direct the second focusing knob 325 to focus the second focusing device. In another example, operating the first focusing knob 320 to defocus the first focusing device may automatically direct the second focusing knob 325 to defocus the second focusing device. Alternatively, operating the first focusing knob 320 to focus the first focusing device may automatically direct the second focusing knob 325 to defocus the second focusing device, or vice versa. In some cases, the first focusing knob 320 and the second focusing knob 325 may operate independently from each other.

Figure 2C:
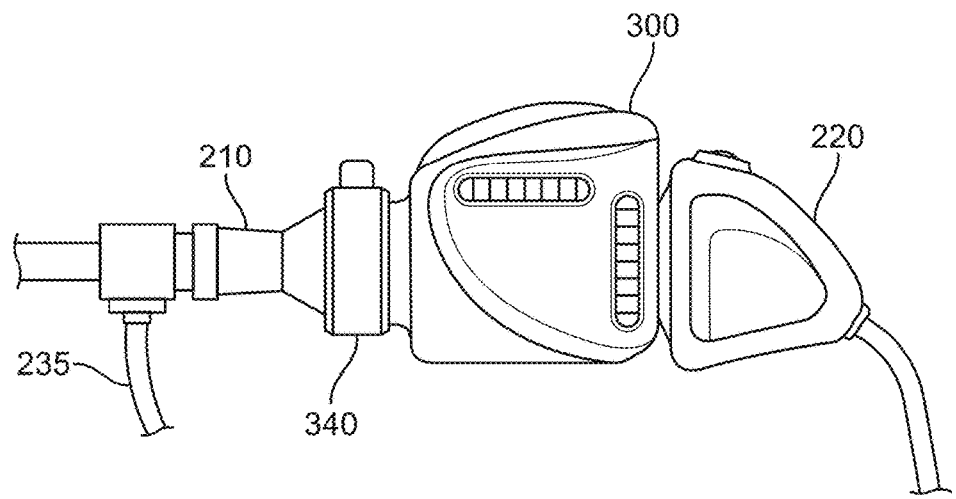
Figure 2D:
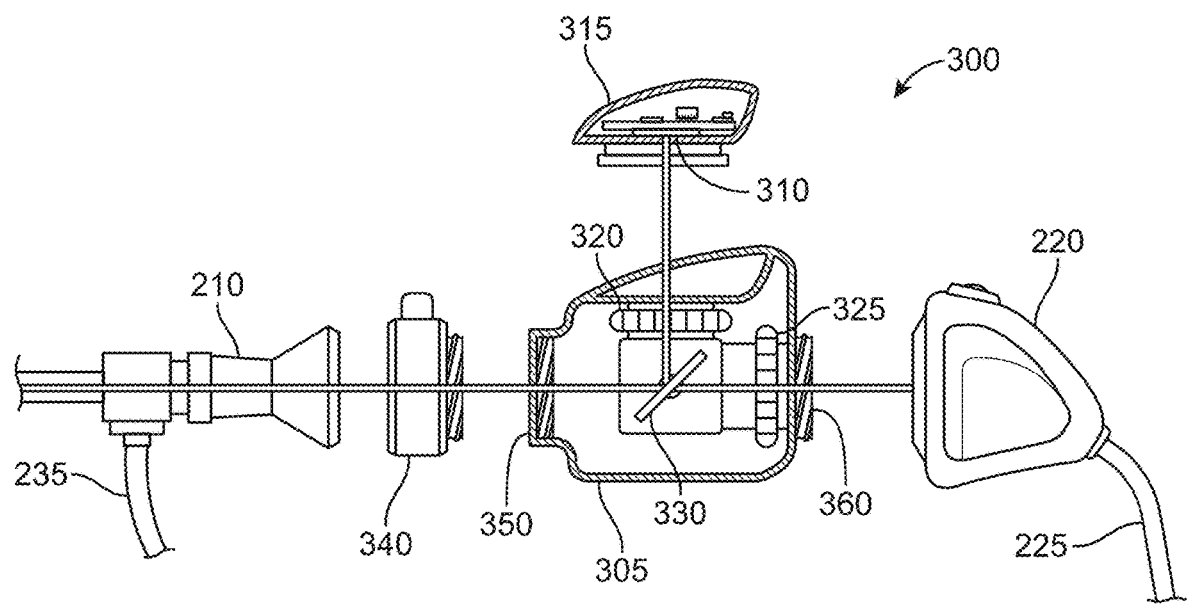

FIGS. 2C and 2D schematically illustrates an example of the ecosystem shown in FIGS. 2A and 2B. The first end 350 of the housing 305 and the scope 210 may be operatively coupled to each other via a coupler 340. The coupler 340 may be configured to releasably couple to the scope 210 and the first end 350 of the housing 305. The coupler 340 may be in optical communication with the scope 210 and the first end 350 of the housing 305.

Figure 3A:
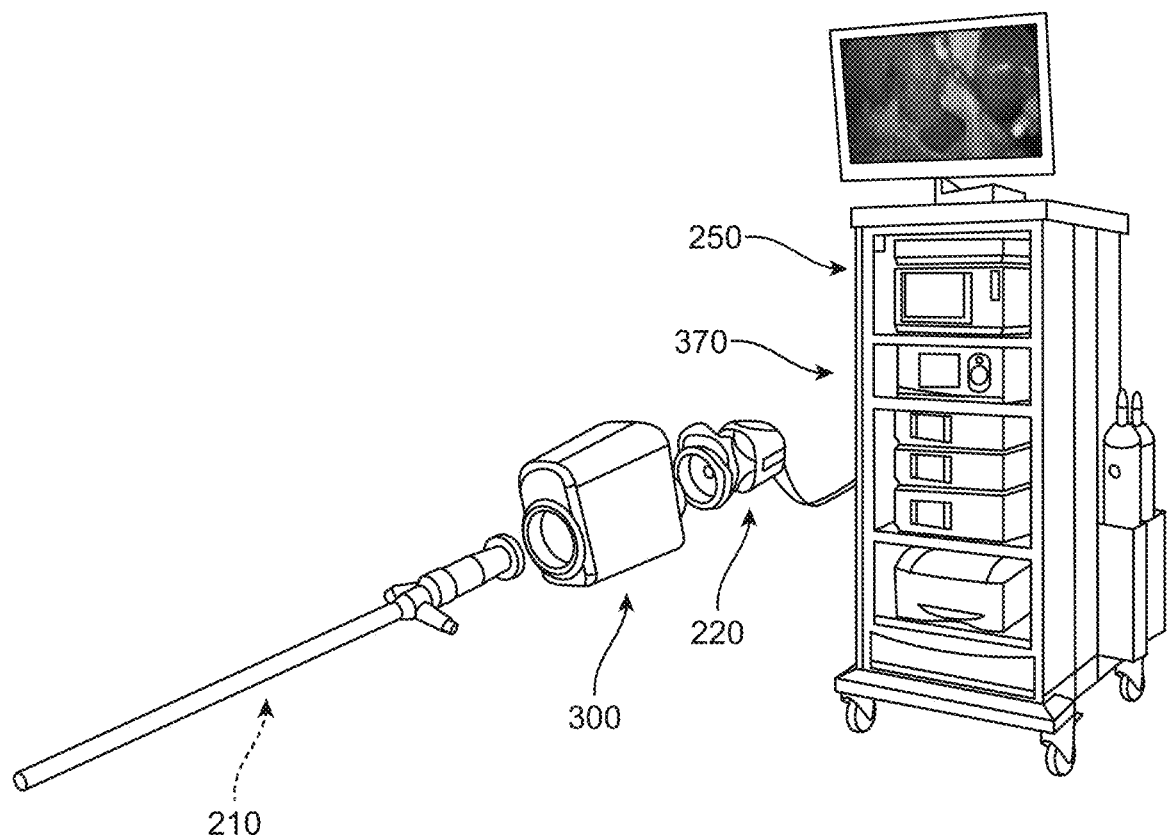
FIGS. 3A, 3B, and 3C schematically illustrate an example ecosystem of a subject optical adapter and a scope apparatus.
Figure 3B:
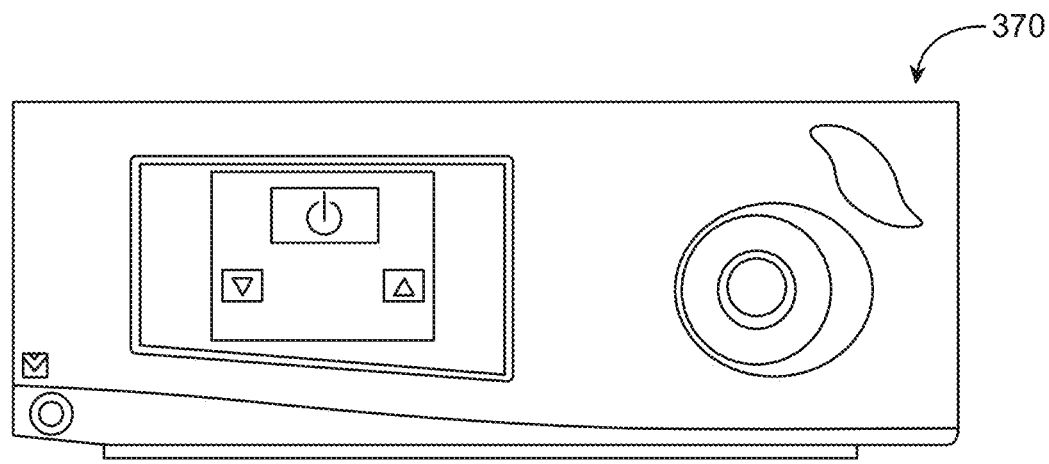

FIGS. 3A-3B schematically illustrate an embodiment of the ecosystem for medical imaging. The ecosystem may comprise a scope assembly 200 comprising a scope 210 and a camera 220. The ecosystem further comprises a subject optical adapter 300 of the present disclosure. For example, the optical adapter 300 may be releasably coupled to the scope assembly 200 and comprise an image sensor and an optics assembly. The optics assembly may be configured to (1) receive light signals that are reflected from a tissue site within a subject's body and transmitted through the scope 210, and (2) reflect a first portion of the light signals onto the image sensor while permitting a second portion of the light signals to pass through to the camera 220.

Referring to FIG. 3A, the scope assembly 200 may be operatively coupled to a base module 250. The base module 250 may comprise a processor configured to analyze data obtained by the camera 220, a light source to provide light to the scope assembly 200, a display (e.g., a liquid crystal display (LCD) or light emitting diode (LED) screen) to visualize the data obtained by the camera. In some cases, the optical adapter 300 may also be operatively coupled to the base module 250. The base module 250 may be configured to provide a combined light (e.g., a white light and one or more laser beams) through the scope 210 and to the tissue site. The processor of the base module 250 may be configured to analyze and visualize a first data set from the image sensor and a second data set from the camera 220. Alternatively, the optical adapter 300 may be operatively coupled to an additional imaging module 370 comprising a light source configured to provide the combined light through the scope 210 and towards the tissue site. Such light source may be optically coupled to the light source (e.g., for white light) of the base module 250, as well as one or more additional light sources that are configured to provide the one or more laser beams. A processor of the additional imaging module 370 may be configured to analyze and visualize the first data set from the image sensor. In addition, the processor of the additional imaging module 370 may be operatively coupled to the processor of the base module 250 to generate a combined analysis and visualization of the first data and the second data set from the camera 220.

As shown in FIG. 3B, the additional imaging module 370 may comprise one or more of the following features: (i) one or more processors for imaging and/or video processing, (ii) database for local image/video storage, (iii) connections (e.g., wired or wireless) to healthcare database network, (iv) connections (e.g., wired or wireless) to the base module 250 of the scope 210, and (v) one or more light sources (e.g., high speed laser light source, hyperspectral light source, etc.).

Figure 3C:
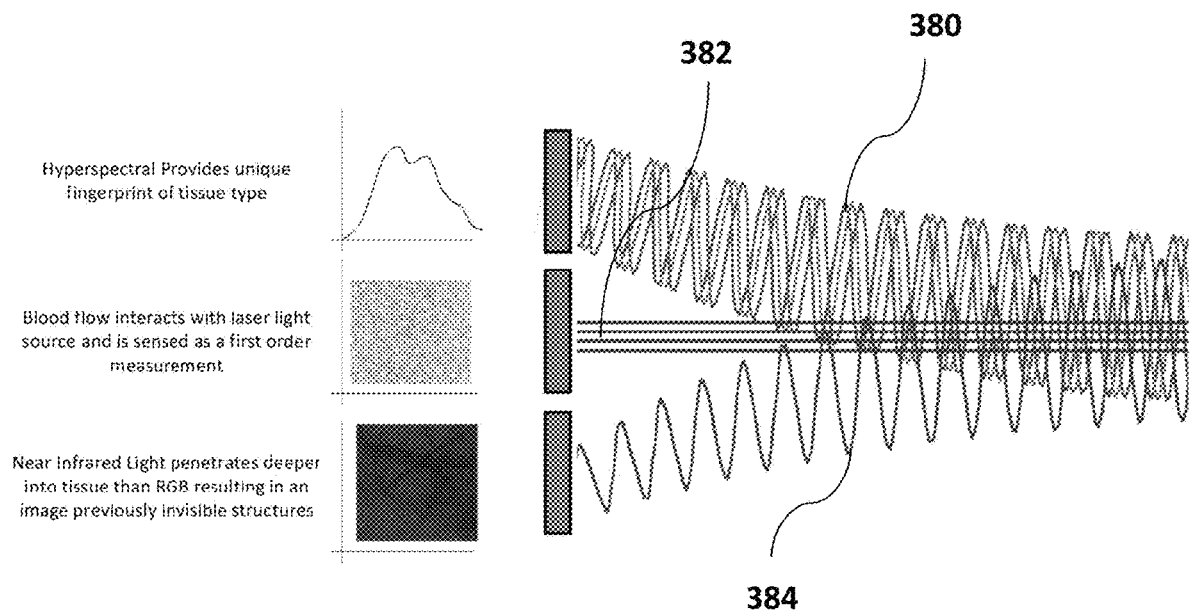

FIG. 3C schematically illustrates multiple imaging modalities achieved by the subject optical adapter of the present disclosure. The base module 250 and/or the additional imaging module 370 may provide a combined light (e.g., a combination of white light and a plurality of laser beams) through the scope 210 and to the tissue site. Upon exposure to the combined light, the tissue site may reflect or emit light signals towards the optical adapter 300. Subsequently, an optics assembly of the optical adapter 300 may be configured to receive the light signals that are transmitted through the scope and reflect at least a portion of the light signals onto an image sensor of the optical adapter. Examples of the at least the portion of the light signals that may be detected and recorded by the image sensor may include, but are not limited to, (i) hyperspectral data 380 as unique fingerprint of the tissue site for identification of the tissue type, (ii) a first order measurement of reflections of laser light beams 382 for perfusion (e.g., blood flow) underneath the tissue site, and (iii) reflection of NIR light 384 that may be indicative of structures of the tissue site that would otherwise be invisible to white light-based imaging. In some cases, the NIR light that is originally directed to the tissue site may be capable of penetrating the tissue site deeper than a white light, and thus reflection of such NIR light may reveal previously invisible structures of the tissue site.

Any subject optical adapter of the present disclosure can be incorporated as part of an imaging kit. In an aspect, the present disclosure provides an imaging kit comprising any of the subject optical adapter of the present disclosure and one or more illumination sources. The one or more illumination sources may be configured to transmit one or more light beams to the scope of the scope assembly for directing the one or more light beams via the scope and onto the target site of the subject's body. The kit may comprise at least 1, 2, 3, 4, 5, 6, 7, 8, 9, 10, or more illumination sources. The kit may comprise at most 10, 9, 8, 7, 6, 5, 4, 3, 2, or 1 illumination source. In some cases, a single illumination source may be configured to transmit at least 1, 2, 3, 4, 5, 6, 7, 8, 9, 10, or more light beams to the scope. The single illumination source may be configured to transmit at most 10, 9, 8, 7, 6, 5, 4, 3, 2, or 1 light beam to the scope. In some cases, a plurality of illumination sources may be configured to transmit at least 2, 3, 4, 5, 6, 7, 8, 9, 10, or more light beams to the scope. The plurality of illumination sources may be configured to transmit at most 10, 9, 8, 7, 6, 5, 4, 3, or 2 light beams to the scope. In an example, the illumination source may be configured to transmit a combined light beam to the scope for directing the combined light beam onto the target site within the subject's body.

Figure 4:
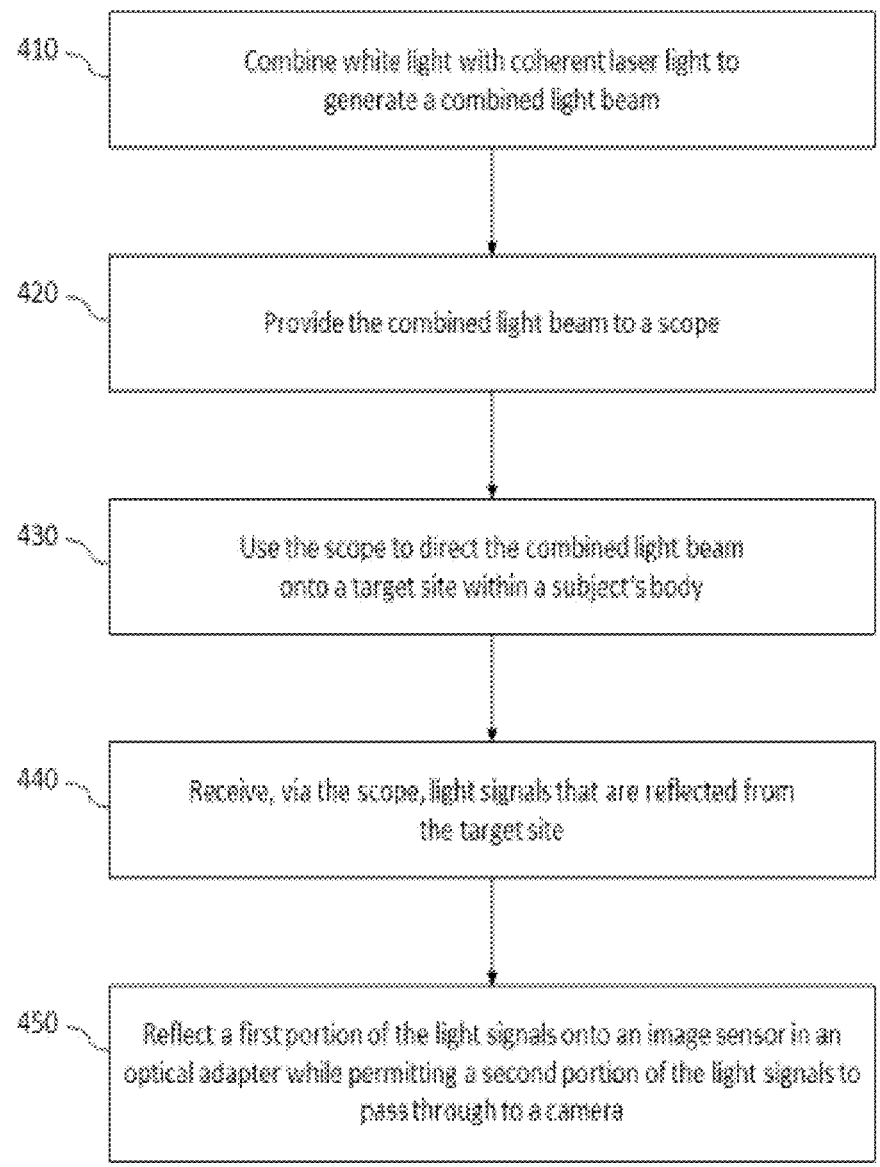
FIG. 4 schematically illustrates an example flowchart of a method for medical imaging, in accordance with some embodiments.

Any subject optical adapter of the present disclosure can be used for medical imaging of a target site of a subject. In an aspect, the present disclosure provides a method of using an optical adapter for medical imaging. FIG. 4 shows an example flow chart of the method of using the optical adapter for medical imaging. The method may comprise providing (i) an optical adapter and (ii) a scope assembly comprising a scope and a camera. The method may comprise combining a first light with a second light to generate a combined light beam. In some cases, the method may comprise combining white light with coherent laser light to generate a combined light beam (process 410). The method may further comprise providing the combined light beam to the scope (process 420). The method may further comprise using the scope to direct the combined light beam onto a target site within the subject's body (process 430). The method may further comprise receiving, via the scope, light signals that are reflected or emitted from the target site (process 440). Alternatively, the method may comprise receiving, via an additional optical path, the light signals that are reflected or emitted from the target site. The method may further comprise reflecting a first portion of the light signals onto an image sensor in the optical adapter while permitting a second portion of the light signals to pass through to the camera, the optical adapter being configured to operatively couple (e.g., releasably couple) to both the scope and the camera (process 450). In some cases, the optical adapter may be disposed between the scope and the camera when releasably coupled thereto. The scope, the optical adapter, and the camera may share a common longitudinal axis.

Figure 5:
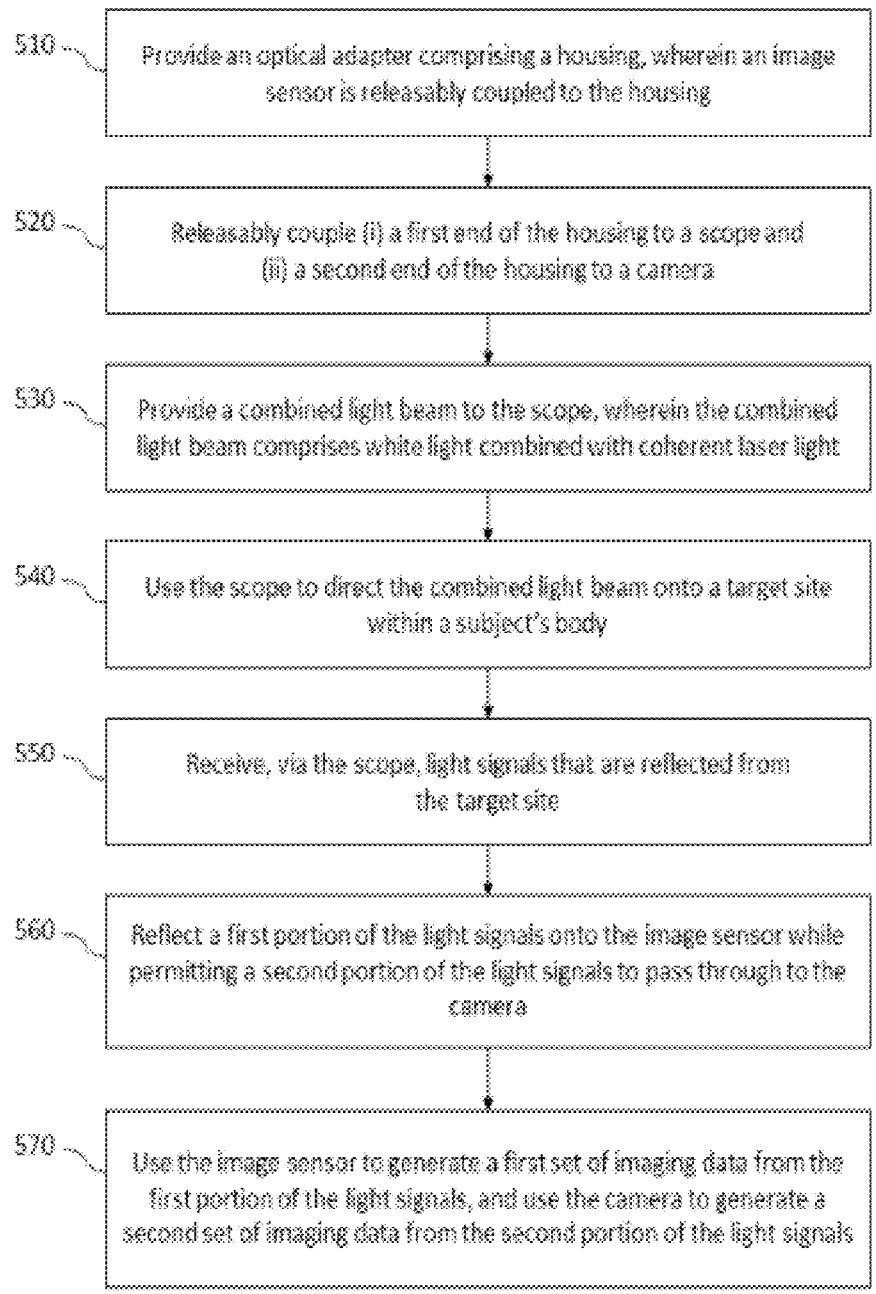
FIG. 5 schematically illustrates a different example flowchart of a method for medical imaging, in accordance with some embodiments.

FIG. 5 shows an additional example flow chart of the method of using the optical adapter for medical imaging.

Figure 6:
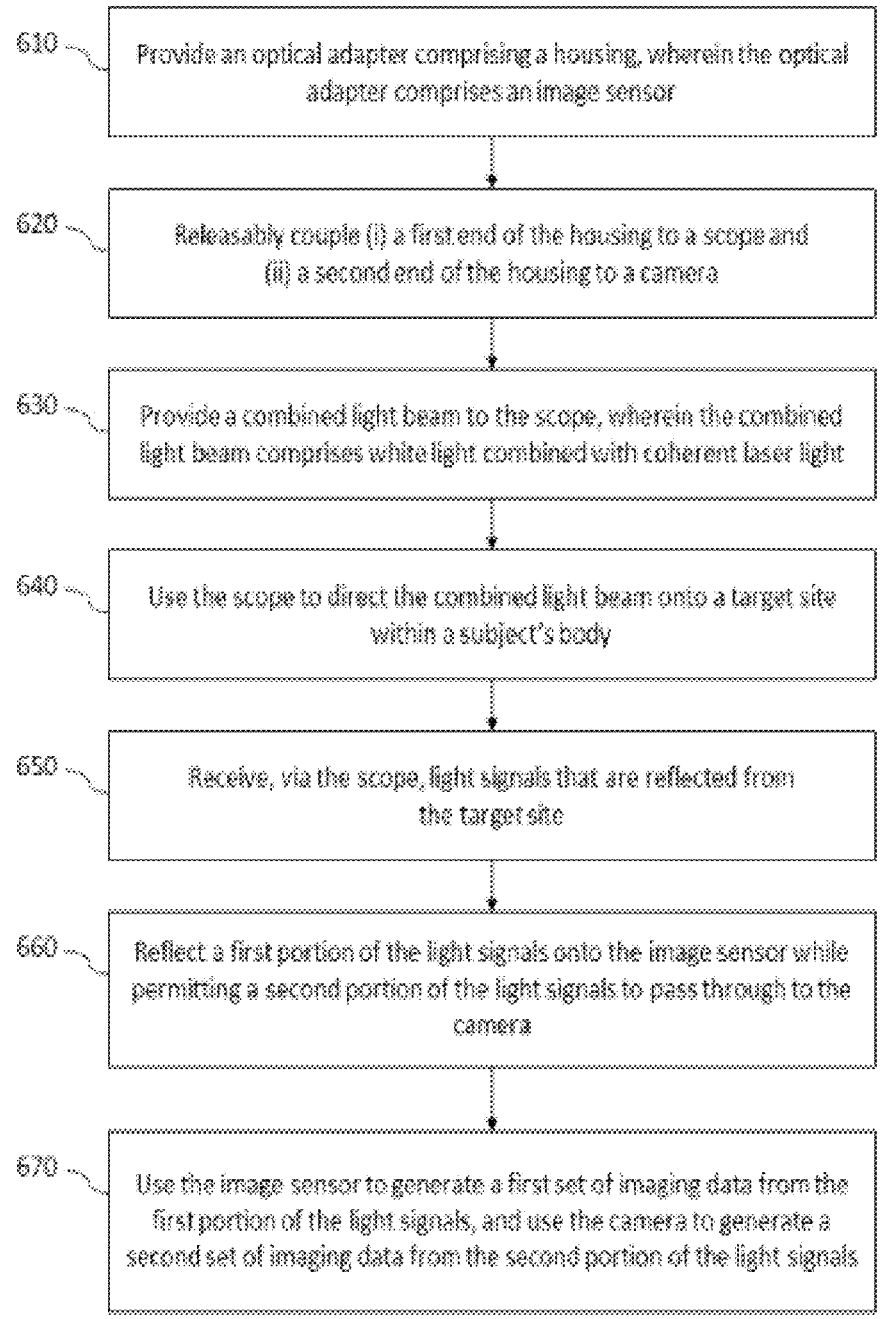
FIG. 6 schematically illustrates another different example flowchart of a method for medical imaging, in accordance with some embodiments.

The method may comprise providing an optical adapter that comprises a housing, wherein an image sensor of the optical adapter may be operatively coupled to the housing (process 510). The image sensor may be permanently or releasably coupled to the housing. The method may further comprise providing a scope assembly comprising a scope and a camera. The method may further comprise operatively coupling (e.g., releasably coupling) a first end of the housing to the scope (process 520). The method may further comprise operatively coupling (e.g., releasably coupling) a second end of the housing to the camera (process 520). The method may further comprise providing a combined light beam to the scope, the combined light beam comprising a first light and a second light. In some cases, the method may comprise providing the combined light beam to the scope, the combined light beam comprising white light combined with coherent laser light (process 530). The method may further comprise using the scope to direct the combined light beam onto a target site within a subject's body (process 540). The method may further comprise receiving, via the scope, light signals that are reflected or emitted from the target site (process 550). Alternatively, the method may further comprise receiving, via an additional optical path, the light signals that are reflected or emitted from the target site. The method may further comprise reflecting a first portion of the light signals onto the image sensor while permitting a second portion of the light signals to pass through to the camera (process 560). The method may further comprise using the image sensor to generate a first set of imaging data from the first portion of the light signals, and using the camera to generate a second set of imaging data from the second portion of the light signals (process 570). In some cases, the first set of imaging data comprises laser speckle patterns. In some cases, the second set of imaging data comprises photographic or video images. Alternatively, the image sensor may not and need not be releasably coupled to the optical adapter, as described in FIG. 6. In such case, the optical adapter may comprise the image sensor, and the image sensor may be integrated within the adapter.

In some embodiments, the optical adapter of the present disclosure may allow a user (e.g., a medical practitioner) to visualize in both (i) an image or video of a target tissue site (e.g., captured by a camera of an existing scope) and (ii) perfusion of a fluid of interest (e.g., blood perfusion) underneath or within the target tissue site. In some cases, the optical adapter may allow the user to visualize (i) the image or video of the target tissue site and (ii) blood perfusion substantially in real time. In some cases, changes in blood perfusion at the target tissue site ma be indicative of one or more surgical complications (e.g., accidentally damaging a blood vessel) or an onset of potential surgical complications (e.g., stroke, seizure, allergic reactions of the subject, etc.). Thus, the optical adapter of the present disclosure may allow a user (e.g., a surgeon in an operating room) to (1) detect one or more procedural or patient-related issues early as compared to an existing scope apparatus alone, and (2) make an informed decision whether to proceed with or abort the remaining surgical procedure.

Figure 7A:
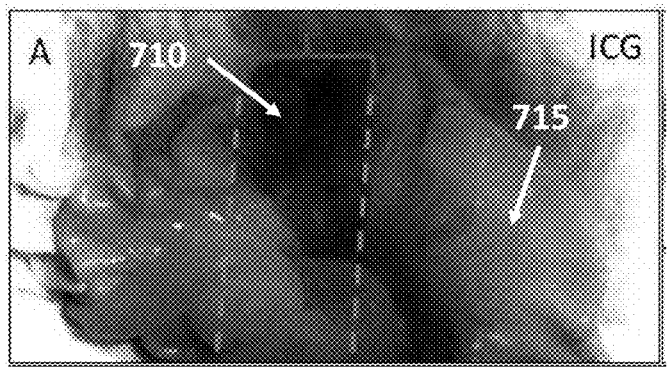
FIGS. 7A, 7B, 7C, and 7D illustrate comparative images of a tissue site obtained by a subject system for medical imaging and an existing dye-based angiography apparatus, in accordance with some embodiments.
Figure 7B:
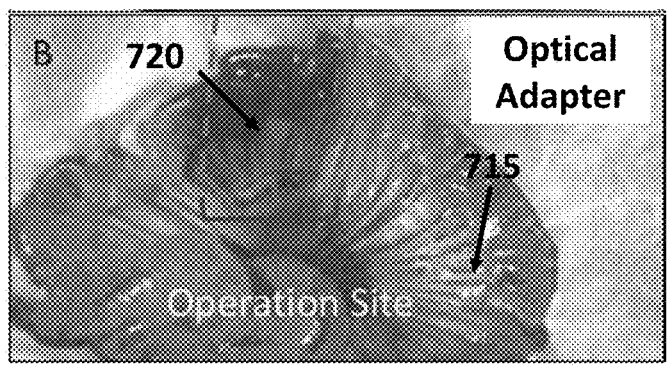

FIGS. 7A-7D illustrates comparative images of a tissue site (e.g., porcine small intestine) of a subject obtained by the optical adapter of the present disclosure or an existing ICG-based angiography. Referring to FIGS. 7A and 7B, some of the vessels in the mesentery were devascularized using electrocautery, and the tissue site was imaged in real-time by the ICG angiography (FIG. 7A) or the optical adapter that is operatively coupled to an endoscope (FIG. 7B). In FIG. 7A, dark regions 710 indicate no blood perfusion, while light regions 715 indicate presence of blood perfusion (e.g., full perfusion). In FIG. 7B, red regions 720 indicate no blood perfusion, while blue regions 725 indicate presence of blood perfusion. Both ICG angiography and the optical adapter can comparatively and accurately distinguish the ablation region (710 and 720, respectively) in the tissue site.

Figure 7C:
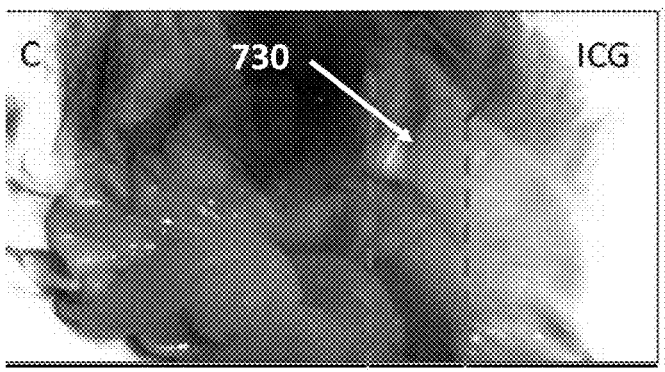
Figure 7D:
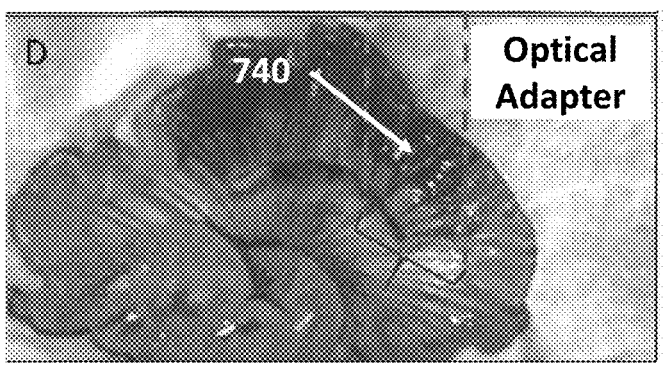

Referring to FIGS. 7C and 7D, devascularization was further extended at the tissue site shown in FIGS. 7A and 7B, and the tissue site was imaged in real-time by the ICG angiography (FIG. 7C) or the optical adapter that is operatively coupled to an endoscope (FIG. 7D). As shown in FIG. 7C, no significant change in the color of the extended ablation site 730 is apparent by the ICG angiography. Rather, the extended ablation site 730 appears to have blood perfusion (i.e., false positive) due to ICG dyes previously injected and still present in the tissue site. In contrast, as shown in FIG. 7D, the extended ablation site 740 clearly captured as a red region, confirming no blood perfusion at such site. Thus, the optical adapter can more accurately depict blood perfusion data than the ICG angiography.

Figure 8A:
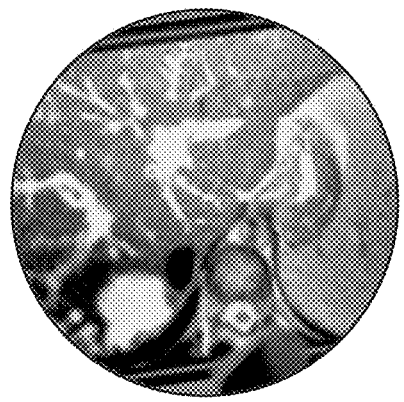
FIGS. 8A, 8B, 8C, and 8D illustrate comparative methods based on existing surgical procedures and a subject system for medical imaging, in accordance with some embodiments.
Figure 8B:
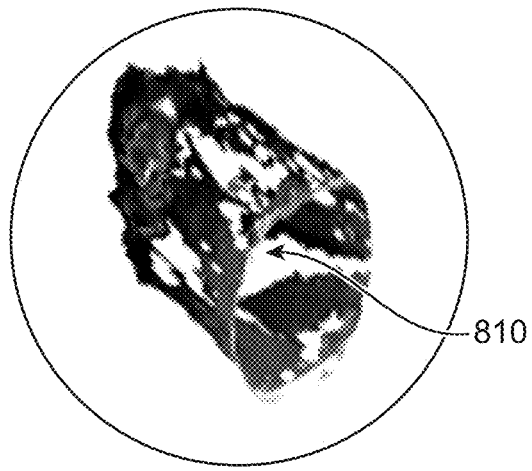
Figure 8C:
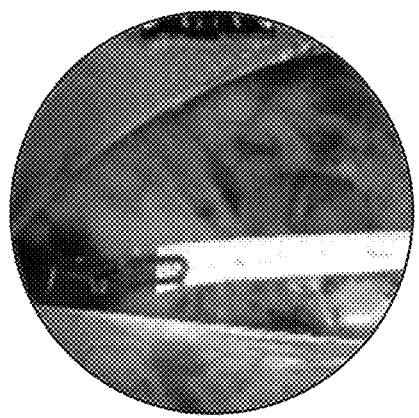
Figure 8D:
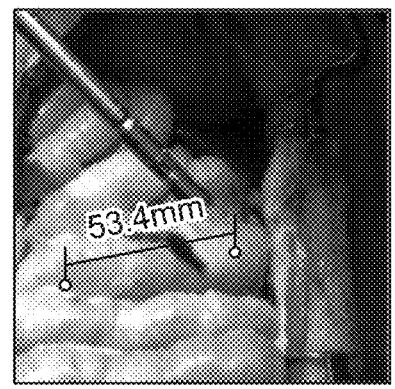

FIGS. 8A-8D illustrates advantages of the optical adapter of the present disclosure in comparison to existing systems and methods for medical imaging. As shown in FIG. 8A, it may be necessary to obtain a survey (e.g., a pre-operation two-dimensional (2D) computerized tomography (CT) scan) of the tissue site prior to the surgery (e.g., 2 to 6 weeks prior to the surgery). In contrast, as shown in FIG. 8B, the optical adapter of the present disclosure, when operatively coupled to any existing endoscope system, may allow real-time visualization one or more features 810 of the tissue site that would not be captured or distinguished by the existing endoscope system alone. In addition, as shown in FIG. 8C, surgeons may often rely on a physical ruler to measure one or more dimensions (e.g., length, area, etc.) of the tissue site or features thereof. In contrast, as shown in FIG. 8D, the optical adapter of the present disclosure may enable accurate measurements of such dimension(s) in real-time without the need for the physical ruler.

The optical adapter of the present disclosure may provide one or more advantages in comparison to existing ICG dye based systems for medical imaging. The ICG dye based systems has been traditionally used for blood perfusion data. In some cases, the ICG dye based systems may require different hardware equipment for different applications. Additionally, one ICG dye based system may not be compatible with all endoscopes. Thus, the ICG dye based systems may not be hardware agnostic. In some cases, instant update of hardware or software of the ICG dye based systems may not be possible. In some cases, because the ICG dye based systems rely on injection of dyes into the subject (e.g., the patient), the ICG dye is for a single-use only and may not be re-used even for the same subject. Additionally, the ICG dye (or any other dyes for dye angiography) may elicit allergic reaction to some subjects, thus may not be applicable with every patient. In some cases, the ICG dye may require time (e.g., several minutes to hours) to reach the target site. In addition, upon reaching the target site, the dye may not stay at the target site for long. Alternatively, the dye may stay at the target site for too long and provide false positive or false negative imaging data. Thus, the ICG dye based systems may not be a reliable method for real-time imaging of the tissue site. In contrast, the optical adapter of the present disclosure (i) may be hardware agnostic, (ii) may receive instant software updates, (iii) may be reused for the same subject or multiple subjects if needed, (iv) may not elicit allergic reactions, (v) may be used with every patient, (vi) may provide 100% real-time data, (vii) and may provide blood perfusion data that is invisible to traditional endoscope systems without any dye-based angiography.

The optical adapter of the present disclosure may provide additional advantages in comparison to existing dye based systems for medical imaging. The optical adapter may exhibit more of the following features than any of the existing dye based systems for medical imaging: (i) minimally invasive imaging capability, (ii) visualization of perfusion at the tissue site, (iii) optimized mucosal view, (iv) tissue identification, (v) quantified multi-dimensional (e.g., three-dimensional) reconstruction and sensing, (vi) dye-free imaging, and (vii) data-rich overlay of images obtained by the optical adapter to images obtained by a traditional endoscope camera.

Figure 9:
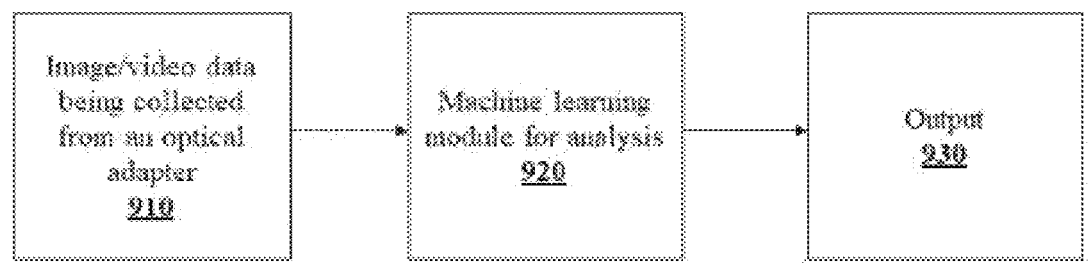
FIGS. 9 and 10 schematically illustrate a machine learning algorithm that is operatively coupled to the subject system for medical imaging, in accordance with some embodiments.
Figure 10:
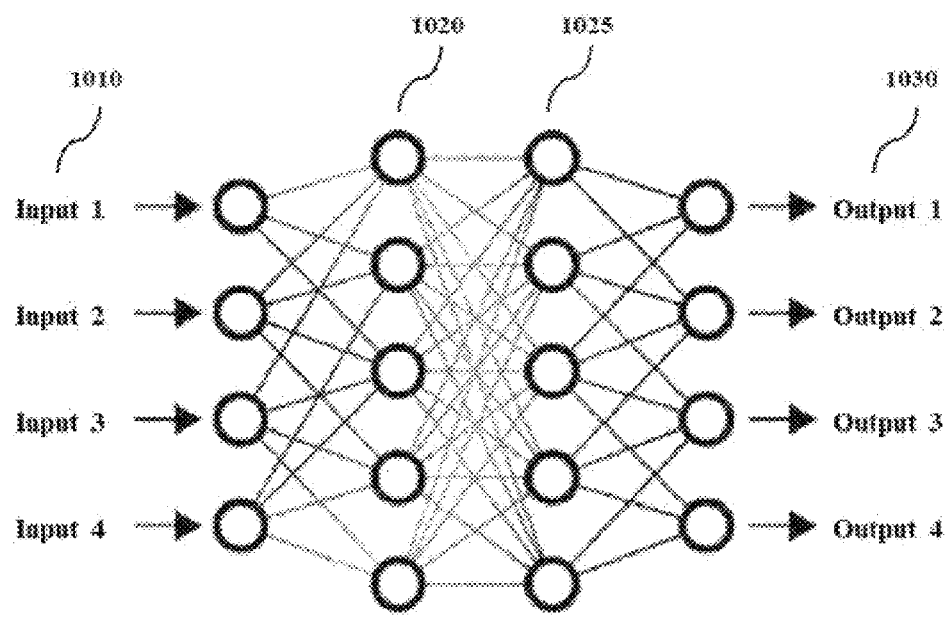

In some embodiments, the optical adapter of the present disclosure may be operatively coupled to a processor (e.g., a computer) configured to analyze a light signal data set (e.g., light spectra, images, or videos) captured by the optical adapter and identify tissue type of the tissue site or one or more features thereof. In an example, the optical adapter may use hyperspectral imaging to identify the tissue type. The processor may be capable of employing one or more machine learning algorithms to analyze a database comprising a plurality of known or previously collected data sets (e.g., light spectra, images, or videos) related to a plurality of tissue sites or features thereof. The one or more machine learning algorithms may be capable of analyzing the light signal data set from the image sensor of the optical adapter or an additional light signal data set from an endoscope camera. The one or more machine learning algorithms may comprise an artificial neural network. The artificial neural network may involve a network of simple processing elements (i.e., artificial neurons) which can exhibit complex global behavior, determined by the connections between the processing elements and element parameters. With or without a training set (e.g., database of previously identified tissue sites and features thereof, along with respective light signal data sets), the artificial neural network may enhance the analysis capability of the machine learning algorithms. As shown in FIG. 9, the one or more machine learning algorithms of the present disclosure may comprise: (i) an input 910 comprising image/video data that is collected from at least the optical adapter of the present disclosure, (ii) a machine learning module 920 for analysis of the input 910, and (iii) an output 930. As shown in FIG. 10, the artificial neural network of the one or more machine learning algorithms may comprise an input layer 1010, one or more hidden layers (e.g., at least two hidden layers 1020 and 1025), and an output layer 1030. The one or more hidden layers may take in input signals (e.g., the light signal data), analyze them, and convert them into an output (e.g., an identified tissue type). In some cases, the light signal data input may comprise at least wavelength (e.g., more than 3 wavelengths, up to 1000 wavelengths, etc.). In some cases, the output layer 1030 may comprise one or more members of the following: (i) tissue identification utilizing spectral fingerprint and/or perfusion data, (ii) spatial location (e.g., X, Y, Z Cartesian coordinates) of the tissue site or features thereof, (iii) quantified perfusion (e.g., blood flow), (iv) surgical decision support (e.g., proceed vs. abort), and (v) geofencing of critical structures within the tissue site of interest.

In some cases, the optical adapter of the present disclosure may collect surgical data that is multiple orders of magnitude denser or more detailed compared to data collected from an existing imaging system (e.g., endoscope or dye-based imaging systems). In an example, a stereoscopic measurement may not be capable of generating a three-dimensional (3D) reconstruction of the tissue site, while the optical adapter of the present disclosure may be capable of generating a quantitative depth map of the tissue site (e.g., with 0.5 millimeter or less depth error).

Any one of the subject optical adapters of the present disclosure can be used to visualize anatomy, morphology, one or more physiological features, and/or one or more pathological features of a target site within a subject's body. Examples of the physiological and/or pathological feature(s) can include, but are not limited to oxygenation, deoxygenation, artery-vein (A-V) classification, flow rate and/or flow volume of a body fluid (e.g., blood, lymph, tissue fluid, milk, saliva, semen, bile, etc.) such as blood perfusion or infarction, angiogenesis, cell density, inflammation, tissue swelling (e.g., brain swelling), tissue death, tissue dimension (e.g., diameter, area, volume), viral infection, bacterial infection, tumor dimension (e.g., diameter, area, volume), tumor margin after a tumor dissection, metastatic growth, etc.

Examples of the target site within the subject's body can include, but are not limited to, thyroid gland, adrenal gland, mammary gland, prostate gland, testicle, trachea, superior vena cava, interior vena cava, lung, liver, gallbladder, kidney, ureter, appendix, bladder, urethra, heart, esophagus, diaphragm, aorta, spleen, stomach, pancreas, small intestine, large intestine, rectum, vagina, ovary, bone, thymus, skin, adipose, eye, brain, fetus, arteries, veins, nerves, ureter, bile duct, healthy tissue, and diseased tissue.

In some cases, a diseased tissue may be affected by a tumor or cancer selected from the group consisting of. Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, *Glomus* tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Vemer Morrison syndrome, Verrucous carcinoma, Visual Pathway Glioma, Vulvar Cancer, Waldenstrom's macroglobulinemia, Warthin's tumor, Wilms' tumor, and combinations thereof.

Computer Systems

Figure 11:
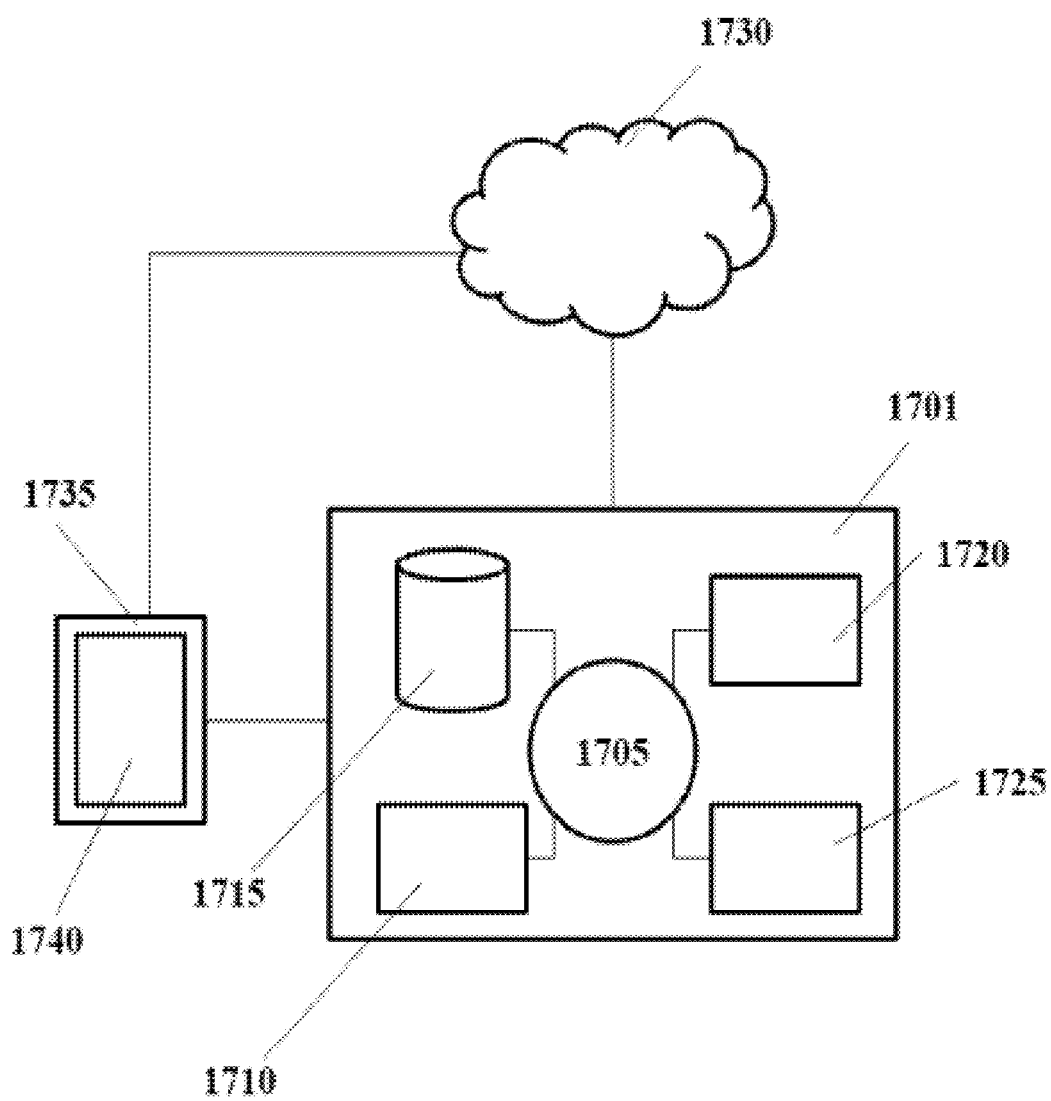
FIG. 11 schematically illustrates a computer system that is programmed or otherwise configured to implement methods provided herein.

In an aspect, the present disclosure provides computer systems that are programmed or otherwise configured to implement methods of the disclosure, e.g., any of the subject methods for medical imaging. FIG. 11 shows a computer system 1701 that is programmed or otherwise configured to implement a method for medical imaging. The computer system 1701 may be configured to, for example, (i) direct an illumination source to combine white light with coherent laser light to generate a combined light beam, (ii) direct the illumination source to provide the combined light beam to a scope of a scope assembly, and (iii) direct an image sensor of an optical adapter to receive at least a portion of a light signal that is reflected or emitted by a target site of a subject upon illumination by the combined light beam. The computer system 1701 can be an electronic device of a user or a computer system that is remotely located with respect to the electronic device. The computer system 1701 may be configured to (a) generate one or more light beams using an illumination source, (b) direct one or more light beams to a movable plate, (c) generate one or more light pulses from the one or more light beams, (d) direct the one or more light pulses to a light aggregation module, (e) combine the one or more light pulses into a combined light signal, (f) provide the combined light signal to a scope, and (g) direct the combined light beam onto a target region in the subject's body. The computer system 1701 can be an electronic device of a user or a computer system that is remotely located with respect to the electronic device. The electronic device can be a mobile electronic device. The electronic device can be a mobile electronic device.

The computer system 1701 may include a central processing unit (CPU, also "processor" and "computer processor" herein) 1705, which can be a single core or multi core processor, or a plurality of processors for parallel processing. The computer system 1701 also includes memory or memory location 1710 (e.g., random-access memory, read-only memory, flash memory), electronic storage unit 1715 (e.g., hard disk), communication interface 1720 (e.g., network adapter) for communicating with one or more other systems, and peripheral devices 1725, such as cache, other memory, data storage and/or electronic display adapters. The memory 1710, storage unit 1715, interface 1720 and peripheral devices 1725 are in communication with the CPU 1705 through a communication bus (solid lines), such as a motherboard. The storage unit 1715 can be a data storage unit (or data repository) for storing data. The computer system 1701 can be operatively coupled to a computer network ("network") 1730 with the aid of the communication interface 1720. The network 1730 can be the Internet, an internet and/or extranet, or an intranet and/or extranet that is in communication with the Internet. The network 1730 in some cases is a telecommunication and/or data network. The network 1730 can include one or more computer servers, which can enable distributed computing, such as cloud computing. The network 1730, in some cases with the aid of the computer system 1701, can implement a peer-to-peer network, which may enable devices coupled to the computer system 1701 to behave as a client or a server.

The CPU 1705 can execute a sequence of machine-readable instructions, which can be embodied in a program or software. The instructions may be stored in a memory location, such as the memory 1710. The instructions can be directed to the CPU 1705, which can subsequently program or otherwise configure the CPU 1705 to implement methods of the present disclosure. Examples of operations performed by the CPU 1705 can include fetch, decode, execute, and writeback.

The CPU 1705 can be part of a circuit, such as an integrated circuit. One or more other components of the system 1701 can be included in the circuit. In some cases, the circuit is an application specific integrated circuit (ASIC).

The storage unit 1715 can store files, such as drivers, libraries and saved programs. The storage unit 1715 can store user data, e.g., user preferences and user programs. The computer system 1701 in some cases can include one or more additional data storage units that are located external to the computer system 1701 (e.g., on a remote server that is in communication with the computer system 1701 through an intranet or the Internet).

The computer system 1701 can communicate with one or more remote computer systems through the network 1730. For instance, the computer system 1701 can communicate with a remote computer system of a user (e.g., a subject, an end user, a consumer, a healthcare provider, an imaging technician, etc.). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1701 via the network 1730.

Methods as described herein can be implemented by way of machine (e.g., computer processor) executable code stored on an electronic storage location of the computer system 1701, such as, for example, on the memory 1710 or electronic storage unit 1715. The machine executable or machine readable code can be provided in the form of software. During use, the code can be executed by the processor 1705. In some cases, the code can be retrieved from the storage unit 1715 and stored on the memory 1710 for ready access by the processor 1705. In some situations, the electronic storage unit 1715 can be precluded, and machine-executable instructions are stored on memory 1710.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media including, for example, optical or magnetic disks, or any storage devices in any computer(s) or the like, may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1701 can include or be in communication with an electronic display 1735 that comprises a user interface (UI) 1740 for providing, for example, a portal for a healthcare provider or an imaging technician to monitor or track one or more features of the optical adapter (e.g., coupling to the scope, coupling to the camera, the image sensor, the optics assembly, etc.). The portal may be provided through an application programming interface (API). A user or entity can also interact with various elements in the portal via the UI. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1705. The algorithm may be configured to (a) generate one or more light beams using an illumination source, (b) direct one or more light beams to a movable plate, (c) generate one or more light pulses from the one or more light beams, (d) direct the one or more light pulses to a light aggregation module, (e) combine the one or more light pulses into a combined light signal, (f) provide the combined light signal to a scope, and (g) direct the combined light beam onto a target region in the subject's body.

In another aspect, the present disclosure provides medical imaging methods and systems usable with an endoscopic device for overlaying a laser speckle contrast image on a standard RGB image of a surgical site. Endoscopic devices may be coupled to RGB video cameras to provide surgeons with high-quality images of anatomical structures or physiological features in a surgical site within a patient's body. Laser speckle contrast imaging may also be used to instantly visualize microcirculatory tissue blood perfusion in a patient's body.

The present disclosure provides methods and systems that can be used with commercially available endoscopic devices for displaying a laser speckle contrast image in addition to a standard image of a surgical site. The images may be displayed individually or together. For instance, the laser speckle contrast image may be overlaid on the standard image of the surgical site.

Figure 12:
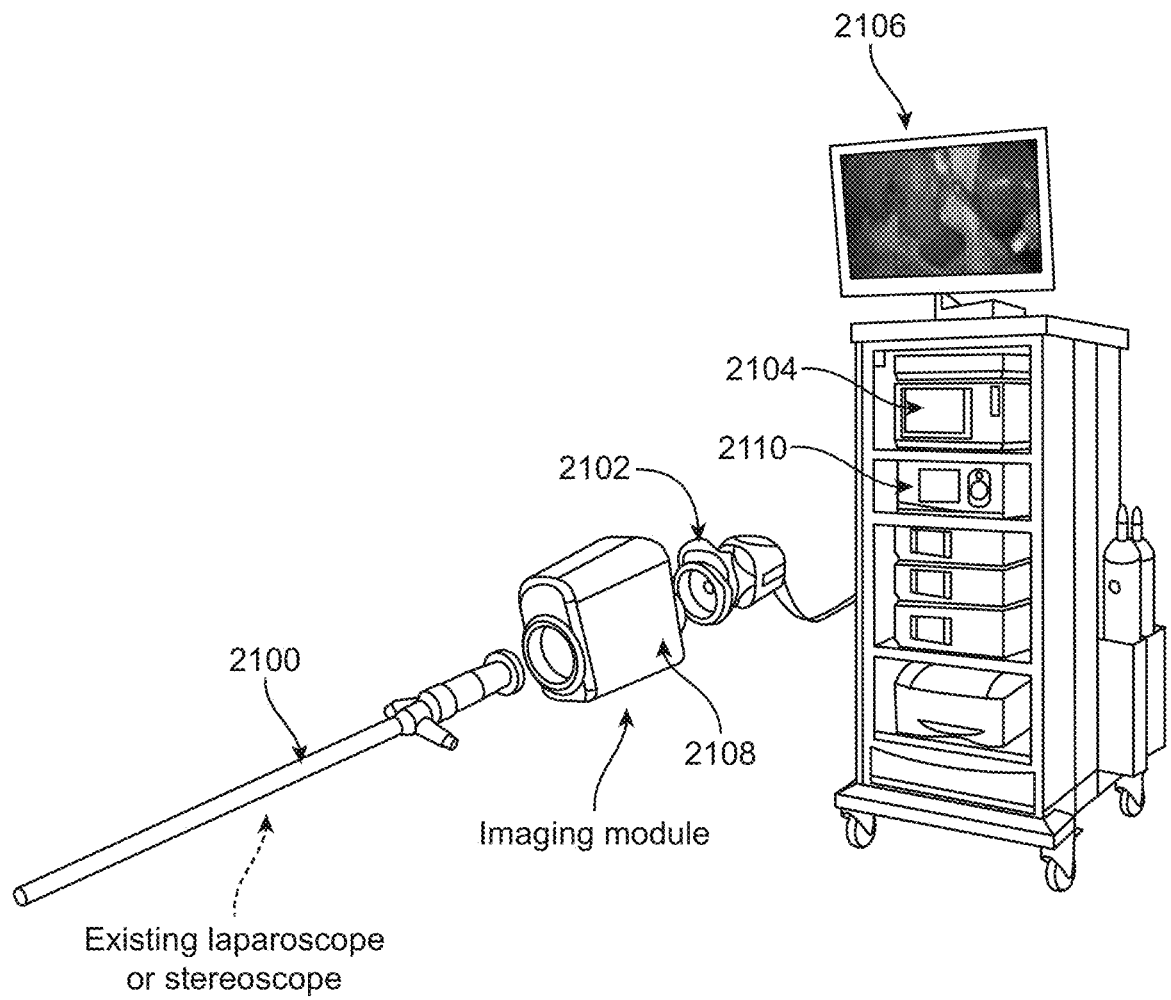
FIG. 12 illustrates an exemplary imaging system in accordance with one or more embodiments.

FIG. 12 illustrates an exemplary imaging system in accordance with one or more embodiments that can be used with any conventional endoscopic imaging system for displaying laser speckle contrast images in addition to standard images of surgical sites. The conventional endoscopic imaging system may comprise an endoscope 2100 (e.g., a laparoscope or stereoscope), which may be directly coupled to an RGB video camera 2102. An image processing system 2104 coupled to the camera 2102 may display standard RGB surgical images on a display 2106.

In some cases, the imaging system may comprise an adapter device 2108, which may be fitted between the endoscope 2100 and the video camera 2102. The imaging system may further comprise a light source and an image processing system 2110.

Figure 13:
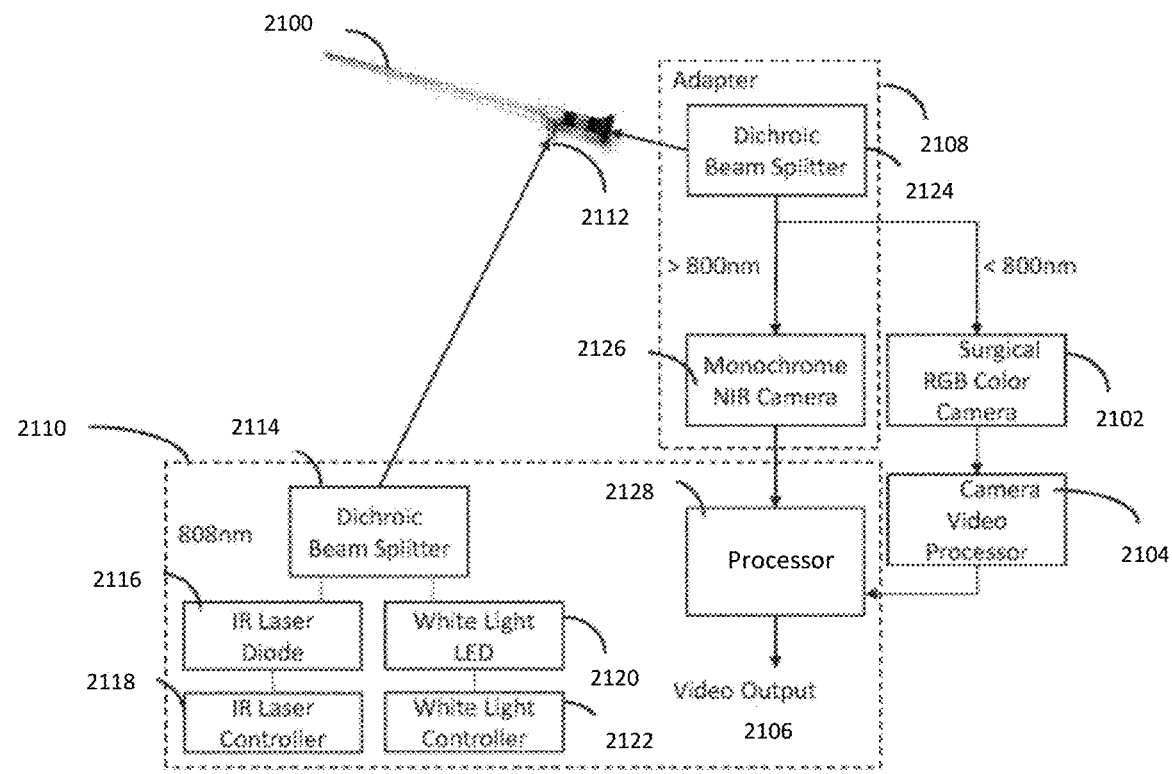
FIG. 13 illustrates a simplified block diagram of the imaging system of FIG. 12, in accordance with some embodiments.

FIG. 13 is a simplified block diagram of an exemplary imaging system in accordance with one or more embodiments. The light source and image processing system 2110 may be configured to combine laser light and white light provided to a light input port 2112 of the endoscope 2100. A dichroic beam splitter 2114 may be configured to combine a laser light from an IR laser diode 2116 controlled by an IR laser controller 2118 with a white light from a white light LED 2120 controlled by a white light controller 2122.

Light from the light sources may be directed through the distal end of the endoscope 2100 and may be incident on the surgical site. Light returned or reflected from the surgical site may be transmitted through the endoscope to the adapter device 2108. A dichroic beam splitter 2124 in the adapter device 2108 may pass light having a wavelength greater than 800 nanometers (nm) to a monochrome near infrared (NIR) camera 2126. Light having a wavelength less than 800 nm may pass to the RGB color camera 2102. The NIR camera 2126 may generate sensor signals that are processed by an image processing system 2128. The RGB color camera 2102 may generate sensor signals that are processed by the camera video processor 2104, which may use the processed sensor signals to generate a standard RGB video stream. The RGB video stream may be provided to the image processing system 2128.

The image processing system 2128 may be configured to perform laser speckle contrast imaging from the sensor signals received from the NIR camera 2126. The image processing system 2128 may be configured to combine the laser speckle contrast imaging with the standard RGB video stream output by the video processor 2104 to produce a video output that can be displayed on the display 2106.

Figure 14A:
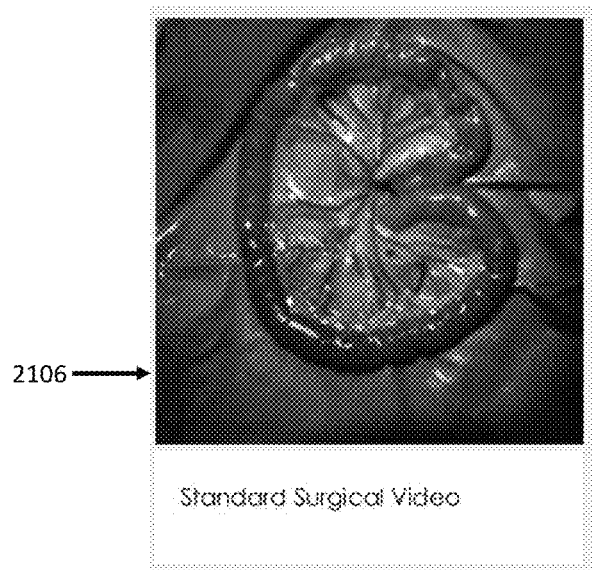
FIGS. 14A, 14B, and 14C illustrate screenshots of an exemplary standard RGB surgical image, laser speckle contrast image, and laser speckle contrast image overlaid on the standard image, in accordance with some embodiments.
Figure 14B:
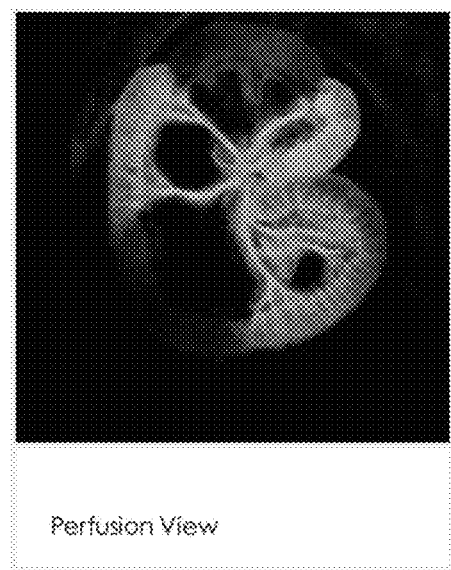
Figure 14C:
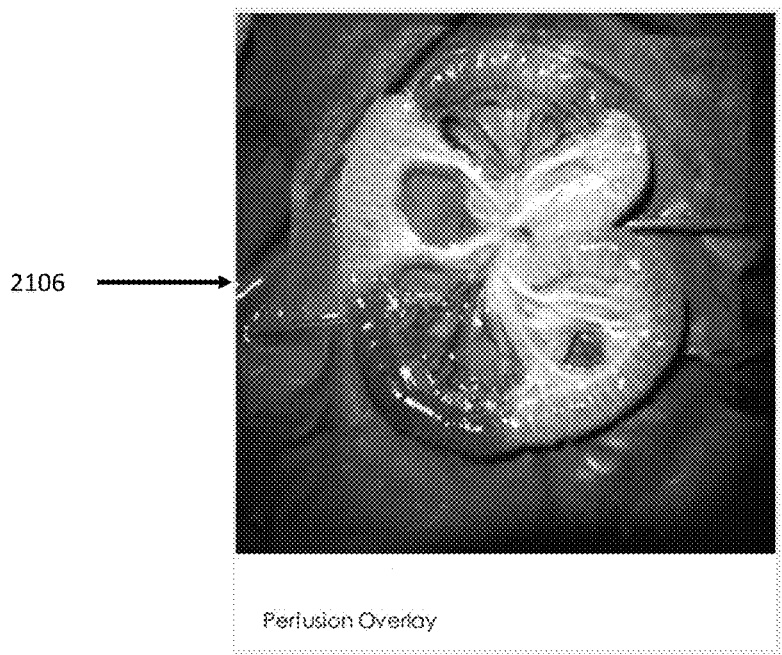

The laser speckle contrast images and the standard RGB images of the surgical site may be displayed individually or together. For instance, the laser speckle contrast image may be overlaid on the standard image of the surgical site. FIG. 14A is an exemplary screenshot from a standard RGB surgical video shown on the display 2106. FIG. 14B shows the corresponding laser speckle contrast image shown on the display 2106. In this example, the highlighted portions in FIG. 14B may indicate one or more areas in the scene where there is blood flow. FIG. 14C shows the laser speckle contrast image of FIG. 14B overlaid on the standard image of FIG. 14A. A user may switch between each of the types of images displayed, as desired.

Figure 15:
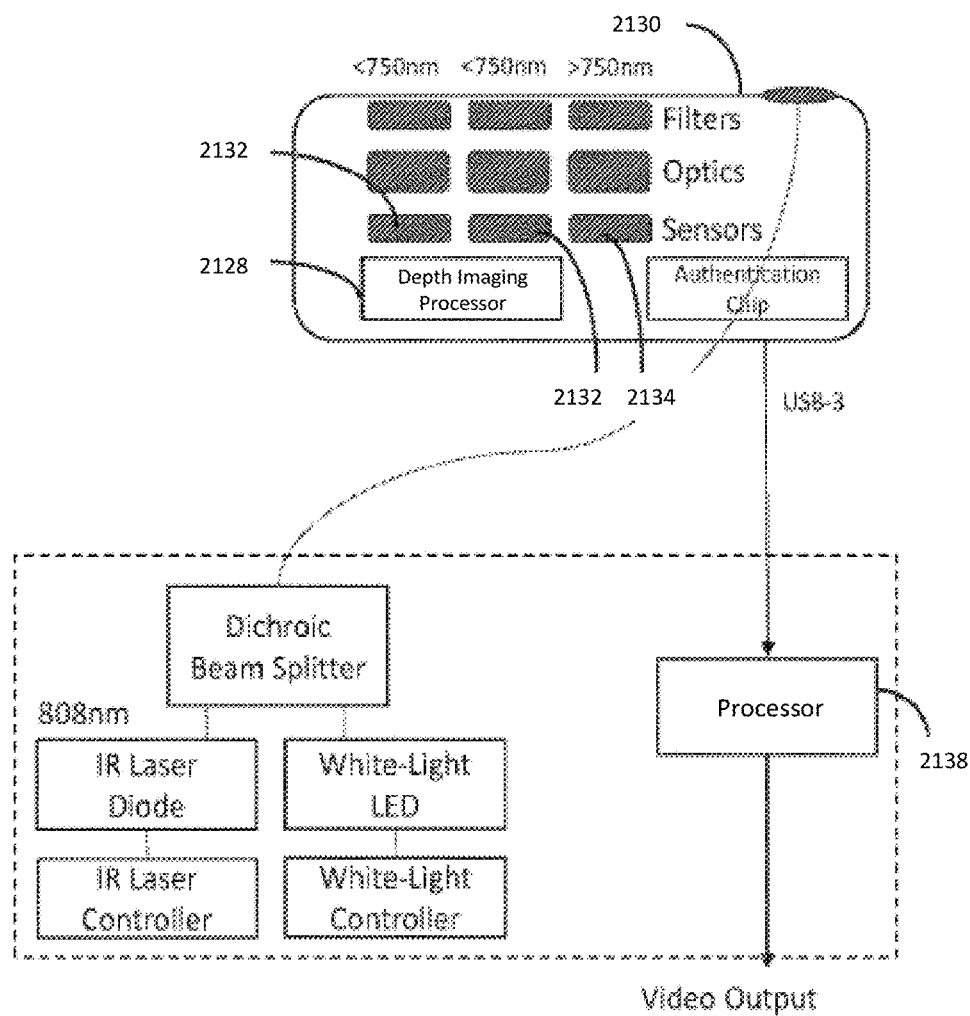
FIG. 15 illustrates a simplified block diagram of an exemplary camera for depth and laser speckle imaging, in accordance with some embodiments.

FIG. 15 is a simplified block diagram illustrating a camera 2130 for performing both depth and laser speckle imaging in accordance with one or more embodiments. The camera 2130 may utilize a depth imaging processor 2128 to generate stereo depth data from two or more sensors 2132. Laser speckle contrast imaging may be performed using data from a third sensor 2134. The image processor 2138 may be configured to process the data from one or more sensors for video output.

Figure 16:
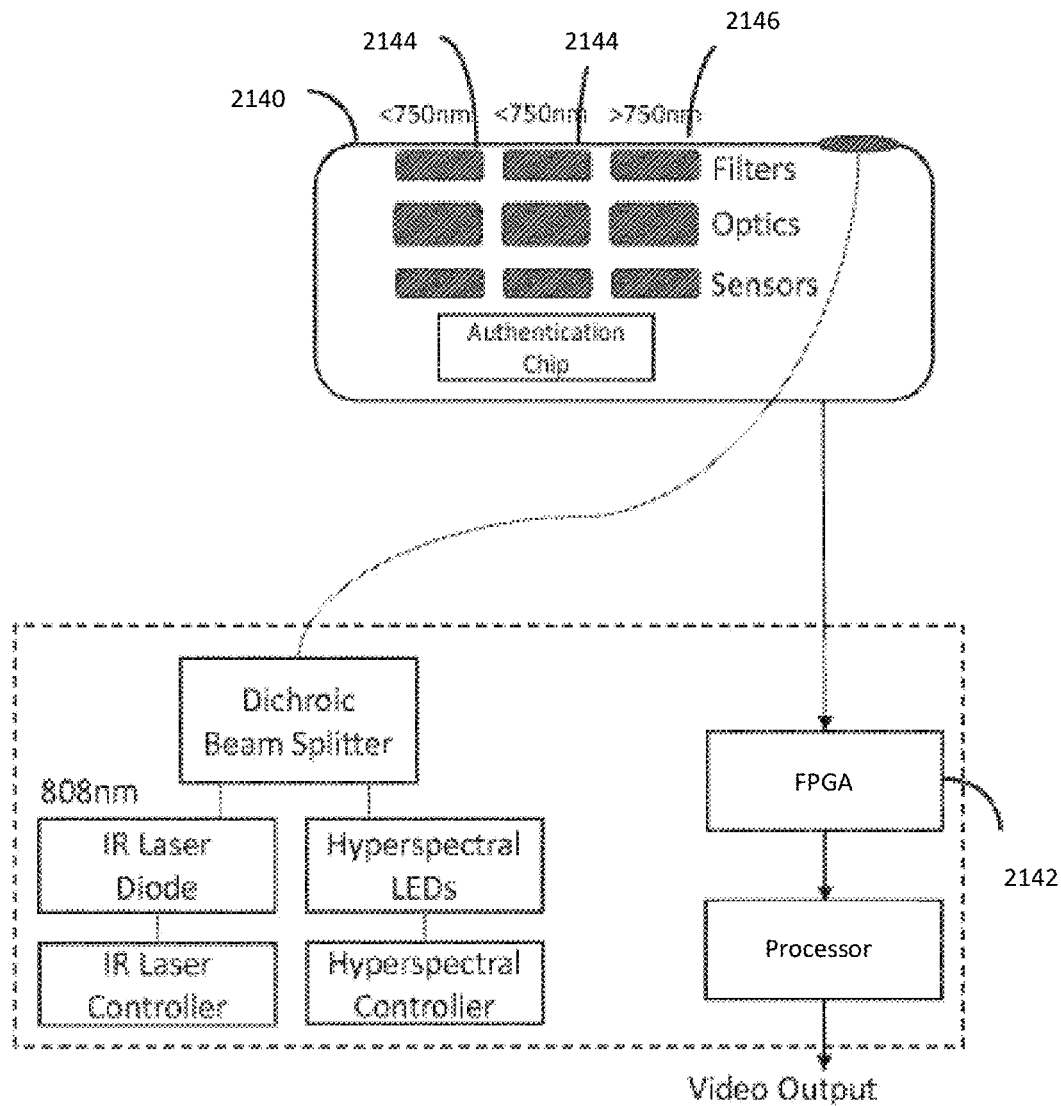
FIG. 16 illustrates a simplified block diagram of an exemplary camera for hyperspectral, depth, and laser speckle imaging, in accordance with some embodiments.

FIG. 16. illustrates a simplified block diagram of an alternate camera 2140 for performing hyperspectral, depth, and laser speckle imaging. Stereo depth imaging may be processed using a field programmable gate array (FPGA) 2142. The stereo depth imaging may be frame synced before being processed by the FPGA. In one or more embodiments, the device may acquire alternating white light and hyperspectral light at one or more sensors 2144 for every other frame (for effective 30 frames per second (FPS) video). 60 frames per second (FPS) video may be used when hyperspectral mode is not enabled. Laser-speckle data may be acquired simultaneously with a third sensor 2146.

Figure 17:
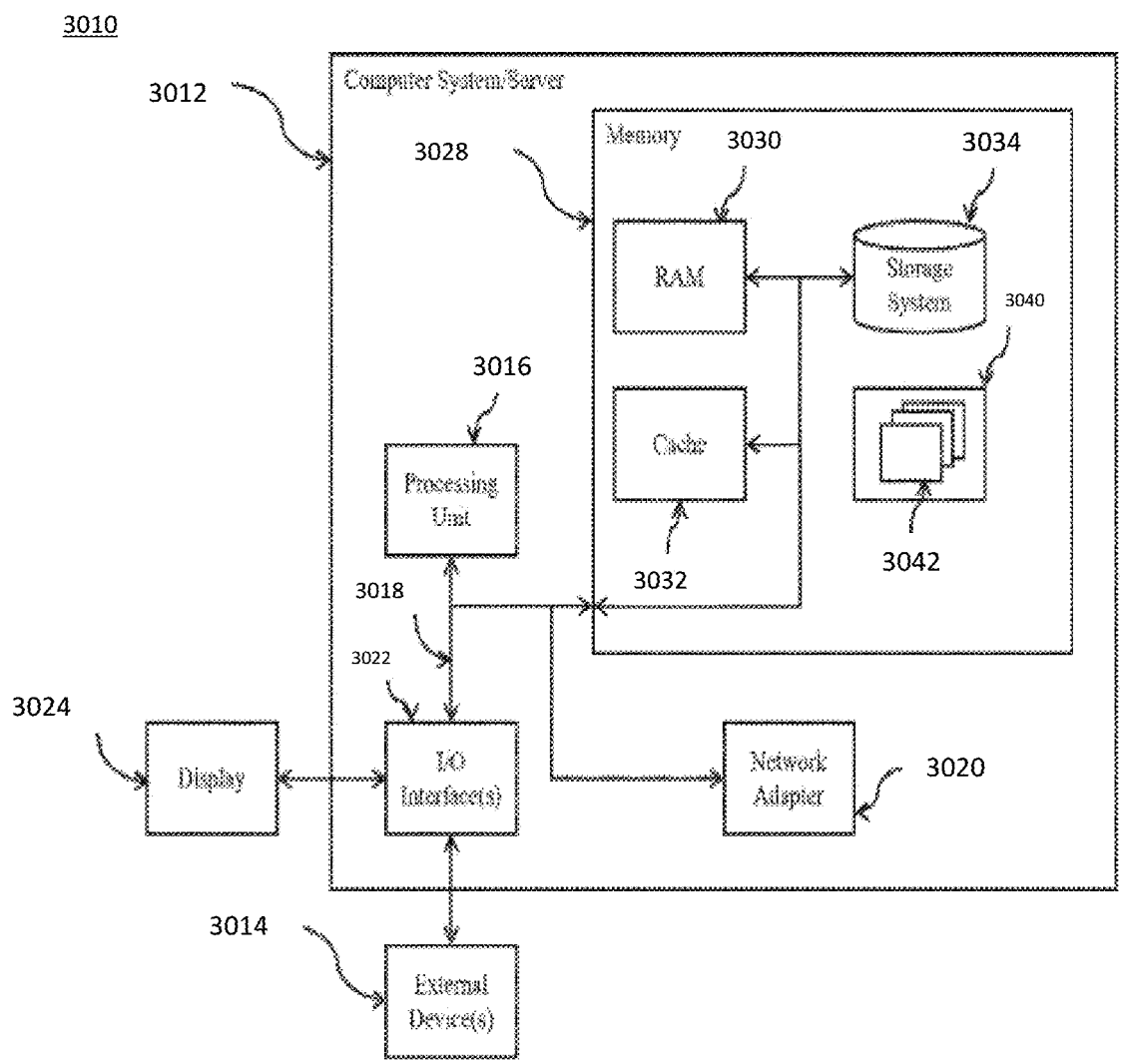
FIG. 17 illustrates a simplified block diagram of an exemplary computer node that can be used in connection with the medical imaging systems disclosed herein.

Referring now to FIG. 17, a schematic of an exemplary computing node is shown that may be used with the medical imaging systems described herein. Computing node 3010 is only one example of a suitable computing node and is not intended to suggest any limitation as to the scope of use or functionality of embodiments described herein. Regardless, computing node 3010 may be capable of being implemented and/or performing any of the functionality set forth hereinabove.

In computing node 3010 there may be a computer system/server 3012, which is operational with numerous other general purpose or special purpose computing system environments or configurations. Examples of well-known computing systems, environments, and/or configurations that may be suitable for use with computer system/server 3012 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 3012 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 3012 may be practiced in distributed cloud computing environments where tasks are performed by remote processing devices that are linked through a communications network. In a distributed cloud computing environment, program modules may be located in both local and remote computer system storage media including memory storage devices.

As illustrated in FIG. 17, computer system/server 3012 in computing node 3010 is shown in the form of a general-purpose computing device. The components of computer system/server 3012 may include, but are not limited to, one or more processors or processing units 3016, a system memory 3028, and a bus 3018 coupling various system components including system memory 3028 to processor 3016.

Bus 3018 may comprise one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 3012 may include a variety of computer system readable media. Such media may be any available media that is accessible by computer system/server 3012, and may include both volatile and non-volatile media, removable and non-removable media.

System memory 3028 can include computer system readable media in the form of volatile memory, such as random access memory (RAM) 3030 and/or cache memory 3032. Computer system/server 3012 may further include other removable/non-removable, volatile/non-volatile computer system storage media. By way of example only, storage system 3034 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 3018 by one or more data media interfaces. As will be further depicted and described below, memory 3028 may include at least one program product having a set (e.g., at least one) of program modules that are configured to carry out the functions of embodiments of the disclosure.

Program/utility 3040, having a set (at least one) of program modules 3042, may be stored in memory 3028 by way of example, and not limitation, as well as an operating system, one or more application programs, other program modules, and program data. Each of the operating system, one or more application programs, other program modules, and program data or some combination thereof, may include an implementation of a networking environment. Program modules 3042 generally carry out the functions and/or methodologies of embodiments described herein.

Computer system/server 3012 may also communicate with one or more external devices 3014 such as a keyboard, a pointing device, a display 3024, etc.; one or more devices that enable a user to interact with computer system/server 3012; and/or any devices (e.g., network card, modem, etc.) that enable computer system/server 3012 to communicate with one or more other computing devices. Such communication can occur via Input/Output (I/O) interfaces 3022. Still yet, computer system/server 3012 can communicate with one or more networks such as a local area network (LAN), a general wide area network (WAN), and/or a public network (e.g., the Internet) via network adapter 3020. As depicted, network adapter 3020 communicates with the other components of computer system/server 3012 via bus 3018. It should be understood that although not shown, other hardware and/or software components could be used in conjunction with computer system/server 3012. Examples, include, but are not limited to: microcode, device drivers, redundant processing units, external disk drive arrays, RAID systems, tape drives, and data archival storage systems, etc.

The present disclosure provides a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a wave-guide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In various embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In various alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The present disclosure provides systems and methods for enhancing medical imaging technology. Conventional medical imaging systems available today may use one or more dyes to help visualize internal processes such as blood flow, but such systems may limit the time frame during which an operator may visualize changes in a patient's blood flow. The systems and methods disclosed herein may be used to enhance medical imaging by selectively controlling the exposure of multiple illumination sources through one or more cut-outs on a movable plate and combining pulses of light from different multi-spectral illumination sources. As such, the system and methods disclosed herein may be implemented to visualize and digitally map anatomical structures within a patient in three-dimensional (3D) perspective, in real-time and without the use of dyes, thereby providing medical operators with additional visual information (e.g., a real-time visual depiction of a patient's blood perfusion) that can inform or guide them during a surgical procedure.

In an aspect, the present disclosure provides a system for illuminating a target region in a subject's body. The system may comprise a plurality of illumination sources comprising (i) a white light source configured to generate a white light beam and (ii) one or more laser light sources configured to generate one or more laser light beams; and a movable plate comprising one or more cut-outs, wherein the movable plate is (i) optically aligned with one or more of the plurality of illumination sources and (ii) configured to move so as to (a) control an exposure of the one or more illumination sources through the one or more cut-outs, relative to a pre-determined frame capture rate, and (b) generate one or more light pulses based on the controlled exposure of the one or more illumination sources.

As used throughout this specification, controlling an exposure of multiple illumination sources may refer to controlling a pulsing of the multiple illumination sources using a movable plate comprising one or more cut-outs. As such, controlling the exposure of multiple illumination sources may be referred to interchangeably as controlling the pulsing of multiple illumination sources. Controlling the pulsing of multiple illumination sources may comprise adjusting one or more time intervals during which each of a plurality of illumination sources is optically aligned with one or more cut-outs of the movable plate.

The target region may be a region within a subject (e.g., a human, a child, an adult, a medical patient, a surgical patient, etc.) that may be illuminated by one or more illumination sources. The target region may be a region within the subject's body. In some cases, the target region may correspond to an organ of the subject, a vasculature of the subject, or any anatomical structure of the subject. In some cases, the target region may correspond to a portion of an organ, a vasculature, or an anatomical structure of the subject.

In some cases, the target region may be a region on a portion of the subject's body. The region may comprise a portion of an epidermis, a dermis, and/or a hypodermis of the subject. In other cases, the target region may correspond to a wound located on the subject's body. The wound may be a burn wound. Alternatively, the target region may correspond to an amputation site of the subject. In any of the embodiments described herein, the target region may correspond to a portion of a subject's body that receives blood flow. The target region may be an organ inside a subject's body or an anatomical feature of a subject's body.

The systems and methods of the present disclosure may allow visualization of structures or features (e.g., blood flow) that are in a target region, near a target region, and/or beneath a surface of a target region, which structures or features would ordinarily be invisible to the human eye or other scope assemblies. The systems and methods of the present disclosure may allow visualization of one or more anatomical structures and/or physiological features or functions. The systems and methods of the present disclosure may be used for physiologic, pathologic, morphologic, and/or anatomic visualizations of various structures, features, and/or functions within a subject's body. The systems and methods of the present disclosure may be used to visualize one or more invisible features in a target region. The systems and methods of the present disclosure may enable a plurality of different imaging modalities. For example, the systems and methods of the present disclosure may enable laser speckle imaging capabilities as well as dye-based imaging and/or white-light based imaging (i.e., RGB photographic images and/or videos). In some cases, the systems and methods of the present disclosure may allow users to switch between different visualization modes, e.g., (i) white-light based video only, (ii) laser speckle imaging only, (iii) dye-based imaging, (iv) both white-light based imaging and laser speckle imaging, or (v) any combination thereof.

The plurality of illumination sources may comprise a white light source. The white light source may comprise a lamp (e.g., an incandescent lamp, a fluorescent lamp, a compact fluorescent lamp, a halogen lamp, a metal halide lamp, a fluorescent tube, a neon lamp, a high intensity discharge lamp, or a low pressure sodium lamp), a light bulb (e.g., an incandescent light bulb, a fluorescent light bulb, a compact fluorescent light bulb, or a halogen light bulb), and/or a light emitting diode (LED). The white light source may be configured to generate a white light beam. The white light beam may be a polychromatic emission of light comprising one or more wavelengths of light. The one or more wavelengths of light may correspond to a visible spectrum of light. The one or more wavelengths of light may have a wavelength between about 400 nanometers (nm) and about 700 nanometers (nm). In some cases, the white light beam may be used to generate an RGB image of a target region of a subject.

The plurality of illumination sources may comprise one or more laser light sources. In some cases, the one or more laser light sources may comprise an infrared (IR) laser, a near-infrared laser, a short-wavelength infrared laser, a mid-wavelength infrared laser, a long-wavelength infrared laser, and/or a far-infrared laser.

As described elsewhere herein, the one or more laser light sources may be configured to generate one or more laser light beams. In such cases, the one or more laser light sources may be configured to operate as a continuous wave laser. A continuous wave (CW) laser may be a laser that is configured to produce a continuous, uninterrupted beam of light with a stable output power. Continuous-wave (CW) operation of a laser means that the laser is continuously pumped and may continuously emits pulses of light and/or energy. The emission can occur in a single resonator mode (i.e., a single-frequency operation) or on multiple resonator modes. In some cases, the laser may be configured to operate as a quasi-continuous-wave laser, in which case the laser may only be switched on for limited time intervals.

The one or more light emitting diodes (LEDs) or laser light sources may be configured to generate one or more laser light beams with a wavelength between about 700 nanometers (nm) and about 1 millimeter (mm). In some cases, the one or more laser light beams may be generated using one or more visible light laser diodes and/or one or more infrared laser diodes. In such cases, the one or more laser light beams may have a wavelength between about 350 nanometers and about 2.5 micrometers ($\mu$m). For example, the one or more laser light beams may have a wavelength of at least about 350 nm, 400 nm, 450 nm, 500 nm, 550 nm, 600 nm, 650 nm, 700 nm, 750 nm, 800 nm, 850 nm, 900 nm, 950 nm, 1000 nm, 1.1 $\mu$m, 1.2 $\mu$m, 1.3 $\mu$m, 1.4 $\mu$m, 1.5 $\mu$m, 1.6 $\mu$m, 1.7 $\mu$m, 1.8 $\mu$m, 1.9 $\mu$m, 2 $\mu$m, 2.1 $\mu$m, 2.2 $\mu$m, 2.3 $\mu$m, 2.4 $\mu$m, 2.5 $\mu$m, or more.

In some cases, the one or more laser light sources may comprise two or more laser light sources that are configured to generate two or more laser light beams having different wavelengths. The two or more laser light beams may have a wavelength between about 700 nanometers (nm) and about 1 millimeter (mm).

As described above, the plurality of illumination sources may comprise one or more laser light sources. In some cases, the one or more laser light sources may comprise a solid-state laser, a gas laser, a liquid laser, and/or a semiconductor laser.

In some cases, the one or more laser light sources may comprise a solid-state laser. A solid-state laser may be a laser that uses a solid material (e.g., glass or a crystalline material) as a laser medium. The solid-state laser may be a ruby laser, a Nd:YAG laser, a NdCrYAG laser, an Er:YAG laser, a neodymium YLF (Nd:YLF) solid-state laser, a neodymium doped Yttrium orthovanadate (Nd:YVO4) laser, a neodymium doped yttrium calcium oxoborate Nd:YCa4O(BO3)3 (Nd:YCOB) laser, a neodymium glass (Nd:Glass) laser, a titanium sapphire (Ti:sapphire) laser, a thulium YAG (Tm:YAG) laser, a ytterbium YAG (Yb:YAG) laser, a ytterbium:2O3 (glass or ceramics) laser, a ytterbium doped glass laser (rod, plate/chip, and fiber), a holmium YAG (Ho:YAG) laser, a chromium ZnSe (Cr:ZnSe) laser, a cerium doped lithium strontium (or calcium) aluminum fluoride (Ce:LiSAF, Ce:LiCAF) laser, a promethium 147 doped phosphate glass solid-state laser, a chromium doped chrysoberyl (alexandrite) laser, an erbium doped laser, an erbium-ytterbiumcodoped glass lasers, a trivalent uranium doped calcium fluoride (U:CaF2) solid-state laser, a divalent samarium doped calcium fluoride (Sm:CaF2) laser, and/or an F-Center laser.

In some cases, the one or more laser light sources may comprise a gas laser. A gas laser may be a laser in which an electric current is discharged through a gas inside a laser medium to produce laser light. The gas laser may be an argon laser, a carbon dioxide laser, a carbon monoxide laser, an excimer laser, a helium laser, a helium-neon laser, a krypton laser, a nitrogen laser, or a xenon laser.

In some cases, the one or more laser light sources may comprise a liquid laser. A liquid laser may be a laser that uses a liquid as a laser medium.

In some cases, the one or more laser light sources may comprise a dye laser. A dye laser may use different organic dyes to produce emissions from the ultraviolet to near infrared spectrum. A dye laser may be operated in the visible with tunable emissions of red, yellow, green, or blue laser emission at almost any wavelength. The dye laser may use Rhodamine-6G in solution.

In some cases, the one or more laser light sources may comprise a semiconductor laser. A semiconductor laser may be a laser that uses a p-n junction of a semiconductor diode as the laser medium. The semiconductor laser may be a semiconductor laser diode, a GaN laser, an InGaN laser, an AlGaInP, an AlGaAs, an InGaAsP, a lead salt laser, a vertical cavity surface emitting laser (VCSEL), a quantum cascade laser, and/or a hybrid silicon laser.

In some cases, the one or more laser light sources may comprise a chemical laser. A chemical laser may include a hydrogen fluoride laser, a deuterium flouride laser, a chemical oxygen-iodine laser, or an all gas-phase iodine laser. In other cases, the laser may be a metal-vapor laser. The metal-vapor laser may be a helium-cadmium (HeCd) metal-vapor laser, a helium-mercury (HeHg) metal-vapor laser, a helium-selenium (HeSe) metal-vapor laser, a helium-silver (HeAg) metal-vapor laser, a strontium Vapor laser, a neon-copper (NeCu) metal-vapor laser, a copper vapor laser, a gold vapor laser, and/or a manganese (Mn/MnCl2) vapor laser. Alternatively, the laser may be a free electron laser, a gas dynamic laser, a Samarium laser, a Raman laser, and/or a nuclear pumped laser.

In some cases, the one or more laser light sources may comprise an excimer laser. An excimer laser may use reactive gases such as chlorine and fluorine mixed with inert gases such as argon, krypton, or xenon. When electrically stimulated, the reactive gases may produce a pseudomolecule or dimer. When exposed to the laser, the dimer may produce light in the ultraviolet range of the electromagnetic spectrum.

In some cases, one or more laser light sources may be used to illuminate a target region located inside a subject's body. Optionally, in other cases, one or more laser light sources may be used to perform one or more surgical procedures (e.g., heating of tissue, removal of tissue, and/or ablation of tissue). The one or more laser light sources used to illuminate a target region in a subject's body may or may not be different than the one or more laser light sources used to perform one or more surgical procedures on the subject or patient. In some cases, the one or more laser light sources may be configured to operate in a first state or a second state. The first state may configure the laser light source to illuminate a target region. The second state may configure the laser light source to perform one or more surgical procedures.

In some cases, each of the plurality of illumination sources may be arranged in a side-by-side or lateral configuration. In such cases, each of the plurality of illumination sources may be separated by a separation distance. The separation distance may be at least about 1 millimeter (mm), 2 mm, 3 mm, 4 mm, 5 mm, 6 mm, 7 mm, 8 mm, 9 mm, 10 mm, or more. In some cases, each of the plurality of illumination sources may be separated by one or more distinct separation distances.

In some cases, each of the plurality of illumination sources may be oriented such that the plurality of illumination sources generates one or more parallel light beams. The one or more parallel light beams may comprise a white light beam generated by the white light source or one or more laser light beams generated by the one or more laser light sources. The one or more parallel light beams may be directed along a path that is perpendicular to a plane corresponding to a position and/or an orientation of a movable plate. In some cases, the one or more parallel light beams may be directed along a path that intersects the plane corresponding to the position and/or orientation of the movable plate at an angle between 0 degrees and 180 degrees.

In some cases, each of the plurality of illumination sources may be oriented such that the plurality of illumination sources generates one or more non-parallel light beams. In such cases, the non-parallel light beams may intersect the plane corresponding to the position and/or orientation of the movable plate at one or more distinct angles. The one or more distinct angles may range from 0 degrees to 180 degrees.

In other cases, each of the plurality of illumination sources may be arranged in a circular configuration or a ring configuration. In such cases, each of the plurality of illumination sources may be positioned around a center point at one or more radial distances. The plurality of illumination sources may be distributed around the center point at one or more angular intervals. The one or more angular intervals may or may not be the same.

In any of the embodiments described herein, the plurality of illumination sources may be arranged such that each of the plurality of illumination sources is disposed at the same distance from the movable plate. In some cases, the plurality of illumination sources may be arranged such that each of the plurality of illumination sources is disposed at one or more distinct distances from a surface or edge of the movable plate.

In any of the embodiments described herein, the plurality of illumination sources may be positioned and/or oriented such that one or more light beams generated by the plurality of illumination sources are directed towards the movable plate along one or more directional vectors. The one or more directional vectors may intersect a surface or an edge of the movable plate at one or more angles. The one or more angles may or may not be distinct. The one or more angles may range from 0 degrees to 360 degrees.

In any of the embodiments described herein, the plurality of illumination sources may be mounted onto a structural component of an illumination module comprising the plurality of illumination sources. The structural component may comprise a wall, a plate, a beam, a rod, or any edge or surface that is internal or external to the illumination module. In some cases, the structural component may be configured to rotate relative to the movable plate.

In some cases, the white light source may be located remote to one or more illumination sources of the plurality of illumination sources (e.g., one or more laser light sources or an ICG excitation light source as described elsewhere herein). In such cases, the white light source may be a third-party light source. The white light source may be configured to generate a white light beam and direct the white light beam to an illumination module comprising one or more laser light sources. The white light beam may be directed towards the illumination module via one or more fiber bundles. The illumination module may then direct the white light beam towards a light aggregation module. The separation of the white light source from the one or more laser light sources may allow the systems disclosed herein to operate with one or more third-party white light sources. Such a configuration may also reduce an amount of heat generated by the plurality of illumination sources and decrease temperature fluctuations while the one or more light sources are operating in an on state (i.e., when the one or more light sources are on and generating one or more light beams). As such, the one or more light beams generated by the plurality of illumination sources may be permitted to stabilize, thereby reducing fluctuations in wavelength and coherence. Further, the separation of the white light source from the one or more laser light sources may minimize a footprint of the illumination module.

In some cases, the illumination module may comprise one or more thermoelectric coolers. The thermoelectric coolers may be configured to cool one or more light sources during operation so that temperature fluctuations may be reduced. As described above, reducing temperature fluctuations may also reduce fluctuations in the wavelength and/or the coherence of the one or more light beams generated by the illumination sources.

In some cases, the plurality of illumination sources may comprise an indocyanine green (ICG) excitation light source. The ICG excitation light source may be configured to generate an ICG excitation light beam. The ICG excitation light beam may cause a fluorescent dye (e.g., indocyanine green) to fluoresce (i.e., emit light). The ICG excitation light beam may have a wavelength of between about 600 nanometers (nm) and about 900 nanometers (nm). The ICG excitation light beam may be emitted onto a target region in a subject's body. The target region may comprise one or more fluorescent dyes configured to absorb the ICG excitation light beam and re-emit fluorescent light with a wavelength between about 750 nanometers (nm) and 950 nanometers (nm). In some cases, the one or more fluorescent dyes may be configured to absorb the ICG excitation light beam and re-emit fluorescent light with a wavelength between about 700 nanometers and 2.5 micrometers ($\mu m$). In some cases, the ICG excitation light source may be disposed relative to the movable plate such that the ICG excitation beam does not pass through the movable plate. In other cases, the ICG excitation light source may be disposed relative to the movable plate such that the ICG excitation beam passes through the movable plate.

Figure 18A:
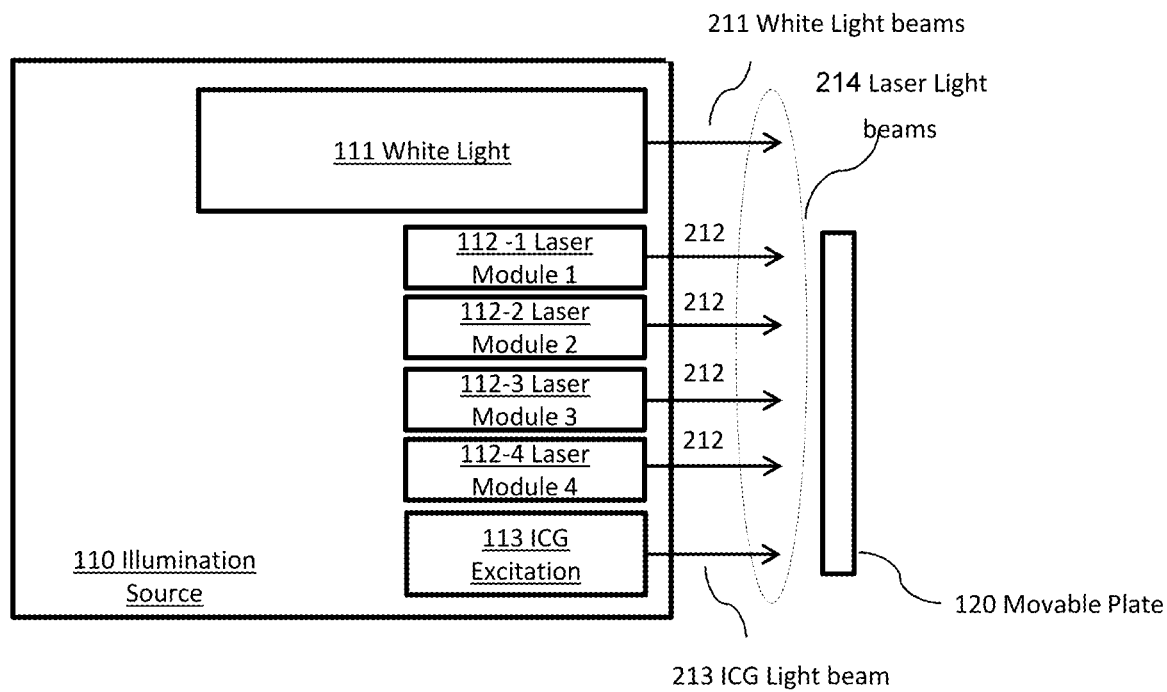
FIGS. 18A and 18B schematically illustrate a plurality of illumination sources, in accordance with some embodiments.
Figure 18B:
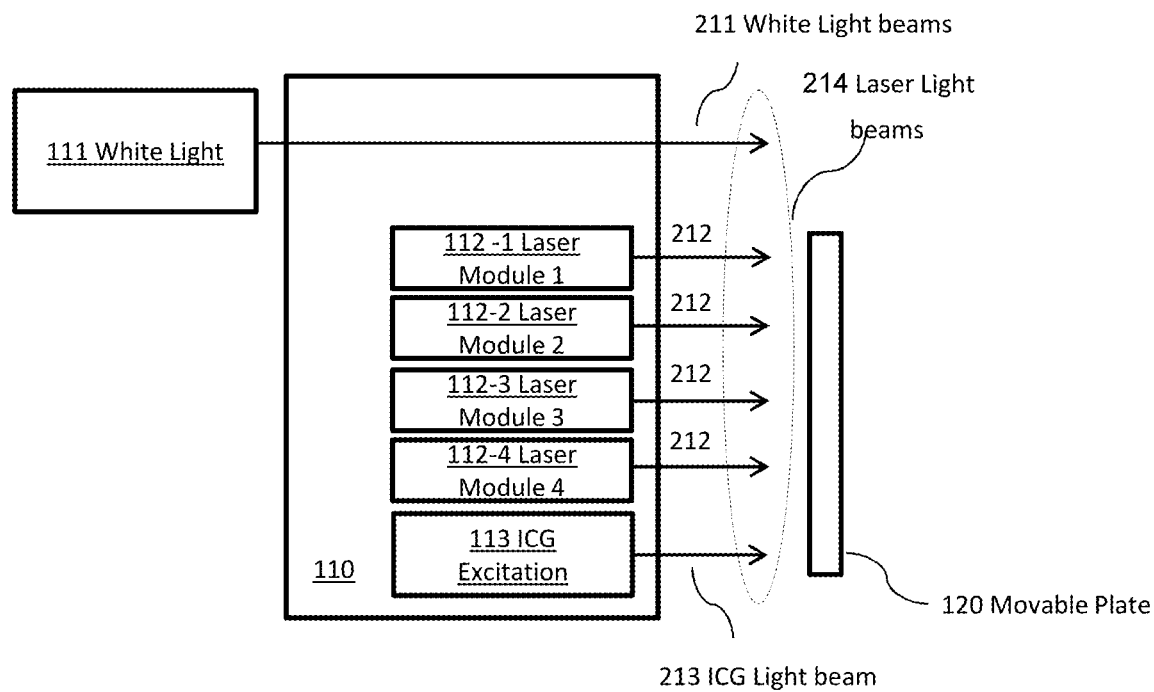

FIGS. 18A-18B illustrate a plurality of illumination sources 110 that may be used to illuminate a target region. The plurality of illumination sources may comprise a white light source 111, one or more laser light sources 112-1, 112-2, 112-3, 112-4, and/or an indocyanine green (ICG) excitation light source 113. The plurality of illumination sources 110 may be configured to generate one or more light beams 212. The one or more light beams 212 may comprise a white light beam 211, one or more laser light beams 214, and/or an ICG excitation light beam 213. The one or more light beams 212 may be directed towards a movable plate 120. As shown in FIG. 18B, in some cases, the white light source 111 may be located remote from an illumination module comprising one or more laser light sources 112-1, 112-2, 112-3, 112-4.

In some cases, the one or more light emitting diodes (LEDs) or laser light sources may comprise two or more LEDs or laser light sources that are configured to generate two or more laser light beams having different wavelengths. In some cases, the two or more laser light sources may be configured to generate two or more laser light beams with a wavelength between about 700 nanometers (nm) and about 1 millimeter (mm). In other cases, the two or more laser light sources may comprise two or more visible light diodes. In such cases, the two or more visible light diodes may be configured to generate two or more laser light beams with a wavelength between about 350 nanometers and about 750 nanometers. In some cases, the two or more laser light beams may have a wavelength between about 400 nanometers and about 700 nanometers.

In some cases, the one or more illumination sources may be configured to generate one or more light pulses. The one or more illumination sources may be configured to generate one or more light pulses using pulse width modulation or pulse duration modulation. A light pulse may be a burst or an emission of light, energy, and/or electrical current. The light pulse may be in the form of an electromagnetic wave. The one or more light pulses may be spaced apart by a predetermined time interval. The one or more light pulses may have a pulse duration. The pulse duration may range between about 1 microsecond to about 100 milliseconds.

In other cases, each of the plurality of illumination sources may be configured to generate one or more continuous light beams. The one or more continuous light beams may be a continuous wave (i.e., a continuous, uninterrupted beam of light with a stable output power). In such cases, a movable plate may be configured to control an exposure of each of the plurality of illumination sources, thereby generating one or more light pulses based on the controlled exposure of the one or more illumination sources.

The plurality of illumination sources may be configured to generate one or more light beams which may be directed towards a movable plate. A movable plate as described herein may be referred to interchangeably as an optical chopper. The movable plate may be a solid object comprising a low transmittance material that is configured to prevent transmission of light through one or more solid portions of the movable plate. The low transmittance material may comprise a dark coating that is configured to prevent transmission of light through one or more solid portions of the movable plate. In some cases, the dark coating may be configured to reduce a radiant power and/or a radiant energy of one or more light beams directed towards the movable plate by a pre-determined amount. In some cases, the pre-determined amount may correspond to a reduction in radiant power and/or radiant energy by at least about 50% or more. The low transmittance material may be sprayed, printed, coated, and/or physically applied onto a surface or an edge of the movable plate. The movable plate may be in the shape of a circle, a square, a rectangle, a triangle, a pentagon, a hexagon, a heptagon, an octagon, a nonagon, a decagon, or any polygon with at least three or more sides. The movable plate may have a horizontal cross-section. The horizontal cross-section may be in the shape of a circle, a square, a rectangle, a triangle, a pentagon, a hexagon, a heptagon, an octagon, a nonagon, a decagon, or any combination of shapes thereof. The movable plate may have a vertical cross-section. The vertical cross-section may be in the shape of a circle, a square, a rectangle, a triangle, a pentagon, a hexagon, a heptagon, an octagon, a nonagon, a decagon, or any combination of shapes thereof.

The movable plate may have one or more dimensions (e.g., height, length, width, and thickness). The one or more dimensions may be at least about 1 millimeter (mm), 2 mm, 3 mm, 4 mm, 5 mm, 6 mm, 7 mm, 8 mm, 9 mm, 10 mm, 10 centimeters (cm), 20 cm, 30 cm, 40 cm, 50 cm, or more.

The movable plate may comprise one or more cut-outs. The one or more cut-outs may correspond to one or more open regions disposed on the movable plate. The one or more open regions may be configured to allow a transmission of light through the movable plate when the one or more cut-outs are optically aligned with at least one of the plurality of illumination sources. In some cases, the one or more open regions may comprise one or more distinct open regions configured to provide one or more distinct exposure times for at least one of the plurality of illumination sources while the movable plate moves (e.g., rotates and/or translates) relative to the plurality of illumination sources. The one or more distinct open regions may have one or more distinct shapes or geometries. The one or more distinct open regions may be disposed on different portions of the movable plate.

Figure 19A:
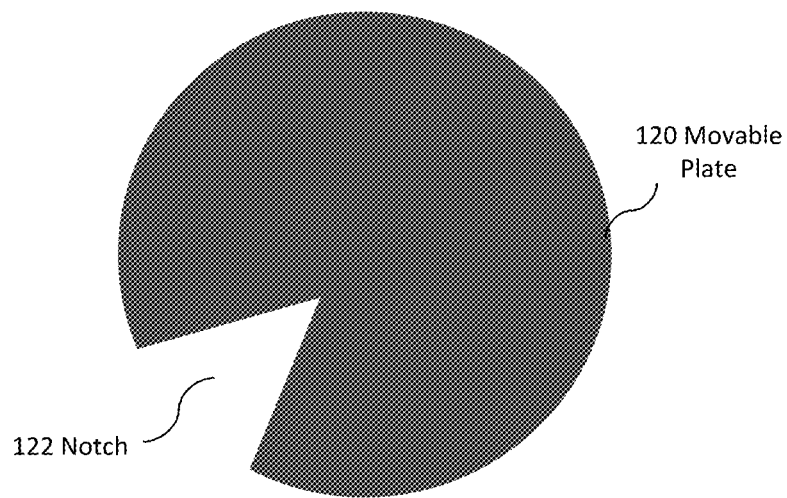
FIGS. 19A and 19B schematically illustrate a movable plate, in accordance with some embodiments.

In some cases, the one or more cut-outs may comprise a notch on the movable plate. FIG. 19A illustrates a movable plate 120 comprising a notch 122. The notch 122 may be an indentation or an incision on an edge or a surface of the movable plate 120. The notch 122 may be in the shape of a triangle, a wedge, or a circular sector (i.e., a portion of a disk enclosed by two radii and an arc). The notch 122 may span a portion of a length, width, height, or circumference of the movable plate. The notch 122 may span an angular range that is greater than 0 degrees and less than 360 degrees. In some cases, the one or more cut-outs of the movable plate 120 may comprise a plurality of notches 122 arranged on different portions or sections of the movable plate 120.

Figure 19B:
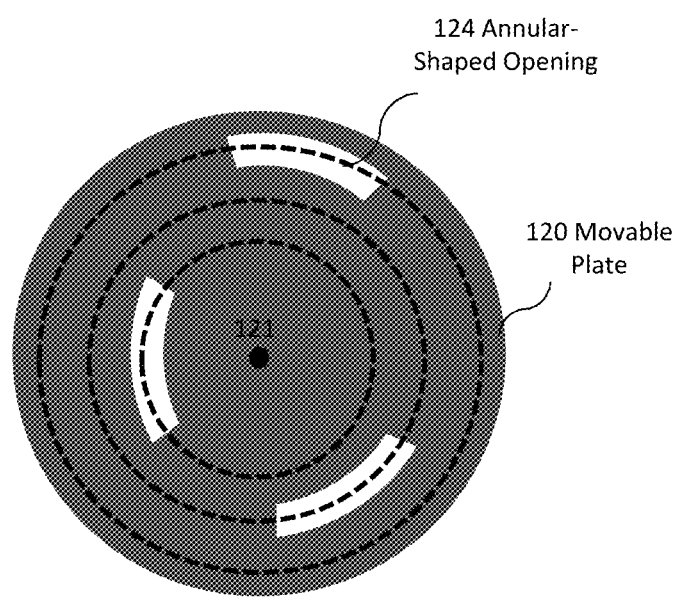

In some cases, the one or more cut-outs may comprise one or more annular-shaped openings on the movable plate. FIG. 19B illustrates a movable plate 120 with one or more annular-shaped openings 124. The one or more annular-shaped openings 124 may be disposed at different radial distances from a center 121 of the movable plate 120. The one or more annular-shaped openings may have an annular shape corresponding to a ring or a portion of a ring. The annular shape may be a shape bounded by two concentric circles. The two concentric circles may or may not have a center that corresponds with a center of the movable plate. Alternatively, the annular shape may be a shape bounded by two concentric arcs and two edges. The two edges may or may not coincide with a radial line extending from a center point associated with the two concentric arcs.

In some cases, the one or more open regions disposed on the movable plate may comprise one or more annular-shaped openings disposed at one or more radial distances from a center of the movable plate. The one or more radial distances may be distinct. In such cases, each of the one or more radial distances may correspond respectively to at least one of the plurality of illumination sources. The one or more annular-shaped openings may be disposed at one or more distinct angular positions relative to each other. In some cases, the one or more annular-shaped openings may be disposed at the same radial distance from the center of the movable plate.

In some cases, the one or more open regions may comprise a first annular-shaped opening and a second annular-shaped opening. In such cases, the first annular-shaped opening may have a first circumferential length that is different than a second circumferential length of the second annular-shaped opening. In other cases, the one or more open regions may comprise three or more annular-shaped openings with different circumferential lengths. The circumferential length may be configured to provide a pre-determined exposure time for each of said plurality of illumination sources. The pre-determined exposure time may be determined based on the circumferential length and/or a rate of rotation (i.e., a rotational rate) of the movable plate.

In some cases, the one or more open regions may comprise one or more wedge-shaped openings. The one or more wedge-shaped openings may be disposed at one or more distinct angular positions relative to each other. In some cases, the one or more open regions may comprise a first wedge-shaped opening and a second wedge-shaped opening. The first wedge-shaped opening may have a first circumferential width that is different than a second circumferential width of a second wedge-shaped opening. In some cases, the one or more open regions may comprise three or more wedge-shaped openings with different circumferential widths.

As described above, the one or more wedge-shaped openings may have a circumferential width. The circumferential width may correspond to a portion of a length of an edge of the movable plate. The circumferential width may be configured to provide a pre-determined exposure time for each of said plurality of illumination sources. The pre-determined exposure time may be determined based on the circumferential width and/or a rotational rate of the movable plate.

In some cases, the one or more distinct open regions may comprise (i) a first open region configured to expose at least one of the plurality of illumination sources for a first pre-determined time interval, and (ii) a second open region configured to expose at least one of the plurality of illumination sources for a second pre-determined time interval. The first open region may have a different geometry and/or shape than the second open region. The first pre-determined time interval may be different than the second pre-determined time interval. In some cases, the one or more distinct open regions may comprise three or more open regions configured to expose each of the plurality of illumination sources for one or more distinct pre-determined time intervals.

The movable plate and/or the one or more cut-outs of the movable plate may be optically aligned with one or more of the plurality of illumination sources. The movable plate and/or the one or more cut-outs of the movable plate may be optically aligned with an illumination source when the illumination source (e.g., a white light source, laser light source, or indocyanine (ICG) excitation light source) is positioned and/or oriented relative to the movable plate such that one or more light beams generated by the illumination source are emitted and/or transmitted along a light path or vector that intersects and/or coincides with (a) the movable plate or (b) an area corresponding to a cut-out portion of the movable plate.

The movable plate may be configured to move (e.g., rotate or translate) relative to the one or more illumination sources to successively (a) allow a transmission of light through one or more cut-outs, and (b) inhibit a transmission of light by physically blocking such transmission of light with one or more solid portions of the movable plate. The one or more solid portions may comprise a low transmittance material, as described elsewhere herein.

The movable plate may be configured to rotate in a clockwise direction and/or a counter-clockwise direction. The movable plate may be configured to rotate at a pre-determined rotational rate. The pre-determined rotational rate may be at least about 100 rotations per minute (RPM), 200 RPM, 300 RPM, 400 RPM, 500 RPM, 600 RPM, 700 RPM, 800 RPM, 900 RPM, 1000 RPM, 1100 RPM, 1200 RPM, 1300 RPM, 1400 RPM, 1500 RPM, 1600 RPM, 1700 RPM, 1800 RPM, 1900 RPM, 2000 RPM, or more.

The movable plate may be configured to control an exposure of the one or more illumination sources by selectively allowing one or more light beams generated by the one or more illumination sources to pass through the one or more cut-outs of the moveable plate, during one or more pre-determined time intervals. The one or more pre-determined time intervals may be determined based on (i) a rotational rate of the movable plate and/or (ii) a shape or geometry associated with the one or more cut-outs. During the one or more pre-determined time intervals, at least one of the plurality of illumination sources may be optically aligned with at least one of the one or more cut-outs.

The movable plate may be configured to control the exposure of the one or more illumination sources relative to a pre-determined frame capture rate. In some cases, the movable plate may be configured to rotate at a pre-determined rate of rotation such that at least a subset of the plurality of illumination sources is exposed for one or more time intervals corresponding to an imaging period. The imaging period may correspond to one or more time intervals during which an imaging device with the pre-determined frame capture rate is configured to acquire one or more image frames. The imaging device may comprise an image sensor or a camera.

The movable plate may be configured to generate one or more light pulses based on the controlled exposure of the one or more illumination sources. The one or more light pulses may be obtained from one or more light beams (e.g., a white light beam, a laser light beam, and/or an indocyanine green (ICG) excitation light beam) generated by the plurality of illumination sources. A light pulse may be generated when the movable plate translates or rotates between a first position that optically aligns one or more illumination sources with one or more cut-outs, and a second position that optically aligns the one or more illumination sources with a solid portion of the movable plate. The pulse duration associated with a light pulse may correspond to a time period during which the movable plate translates or rotates between the first position and the second position. The pulse duration may be a function of the shape or geometry of the movable plate and/or the shape or geometry of the one or more cut-outs. For example, a first cut-out with a first dimension may produce a first light pulse with a first pulse duration that is longer than a second pulse duration associated with a second light pulse produced by a second cut-out with a second dimension that is less than the first dimension. The pulse duration may be a function of a rate of rotation of the movable plate. For example, the pulse duration may be longer when the movable plate rotates at a lower rate of rotation since a lower rate of rotation may allow for an illumination source to be optically aligned with one or more cut-outs for a longer period of time.

The use of the movable plate to generate one or more light pulses may permit the systems disclosed herein to operate with the plurality of illumination sources continuously on during medical imaging, and without electronically pulsing the illumination sources. This may allow the plurality of illumination sources to generate and maintain one or more coherent light beams. As an additional advantage, the one or more light beams (e.g., white light beam, laser light beam, and/or ICG excitation light beam) may be permitted to stabilize such that the coherence of the one or more light beams is improved relative to a system where the illumination sources are pulsed electronically, or where the illumination sources are alternated between an on state and an off state.

The exposure of each of the plurality of illumination sources may be synchronized to an image frame capture rate associated with an imaging device (e.g., an image sensor and/or a camera). As such, the generation and/or transmission of one or more light pulses may be synchronized to the acquisition of one or more image frames captured by an imaging device. The one or more image frames may be acquired at an image frame capture rate associated with the imaging device. The one or more image frames captured by the imaging device may comprise spectral data generated in part based on the interaction (i.e., a reflection and/or a deflection) of a subset of the one or more light pulses with a target region in a subject's body. In some cases, each of the one or more image frames may correspond to a different illumination source of the plurality of illumination sources, or a different subset of the plurality of illumination sources.

In some cases, the exposure of each of the plurality of illumination sources may be synchronized to an image frame capture rate of an imaging device using a timing signal. The timing signal may be generated using one or more photointerrupters. A photointerrupter may comprise a sensor configured to detect if one or more light beams are incident on the sensor. In some cases, one or more photointerrupters may be positioned adjacent to each of the plurality of illumination sources. The one or more photointerrupters may be configured to generate a timing signal, which may be provided to a microcontroller configured to (i) adjust the image frame capture rate of the imaging device and/or (ii) adjust a time at which the camera captures one or more image frames. Adjusting the image frame capture rate may involve synchronizing the image frame capture rate to a rate at which one or more illumination sources are exposed through a notch of the movable plate. Alternatively, adjusting the image frame capture rate may involve synchronizing the image frame capture rate to a time at which one or more illumination sources are exposed through a notch of the movable plate. In some cases, the microcontroller may be configured to compensate for any delays associated with transmission of the timing signal by modifying the timing signal.

In some cases, the timing signal generated by the one or more photointerrupters may be provided to a microcontroller, a field-programmable gate array (FPGA), or one or more electronic gates. The microcontroller, the field-programmable gate array (FPGA), and/or the one or more electronic gates may be configured to generate a trigger signal based on the timing signal obtained from the one or more photointerrupters. The trigger signal may be used by the camera or the imaging device to trigger an exposure of one or more image frames.

In some embodiments, the medical imaging system may comprise a movable plate with a cut-out, three laser diodes, and three photointerrupters located adjacent to the three laser diodes. The movable plate may be configured to rotate relative to the three laser diodes at a rotational rate of 2400 rotations per minute (RPM). In such cases, the three photointerrupters may be configured to pulse at 40 hertz (Hz). The medical imaging system may comprise a microcontroller, a field-programmable gate array (FPGA), and/or one or more electronic gates configured to combine one or more pulses generated by the three photointerrupters into a trigger signal at 120 Hz. The camera or imaging device may be configured to capture one or more image frames upon receiving the trigger signal. The camera or imaging device may be configured to acquire one or more image frames at 120 frames per second. In such embodiments, a commanded speed of a motor that is configured to control a movement of the movable plate may dictate an image frame capture rate of the camera or imaging device.

In some cases, the exposure of each of the plurality of illumination sources may be synchronized to an image frame rate of an imaging device using a timing signal generated by the imaging device. In such cases, the imaging device may be configured to generate a timing signal based on a rate at which the camera captures one or more image frames and/or a time at which the camera captures one or more image frames. The timing signal may be provided to a microcontroller, which may be configured to adjust a rate and/or a time at which one or more illumination sources are pulsed or exposed through a notch of the movable plate. In some cases, adjusting the rate of exposure of the one or more illumination sources may involve adjusting a speed at which the movable plate rotates or translates relative to the one or more illumination sources. In other cases, adjusting the rate of exposure of the one or more illumination sources may involve adjusting a time at which one or more notches of the movable plate are optically aligned with the one or more illumination sources.

In any of the embodiments disclosed herein, the system may further comprise an additional movable plate configured to rotate relative to the plurality of illumination sources and the movable plate. The additional movable plate may be configured to rotate at a second rate that is different than a first rate at which the movable plate is configured to rotate. The additional movable plate may be configured to rotate in a second direction that is different than a first direction in which the movable plate is configured to rotate. The movable plate may comprise a first set of cut-outs with a different geometry or arrangement than a second set of cut-outs on the additional movable plate. The movable plate may have a first shape or geometry that is a different than a second shape or geometry of the additional movable plate. The movable plate and the additional movable plate may have different shapes, geometries, and/or dimensions.

Figure 19C:
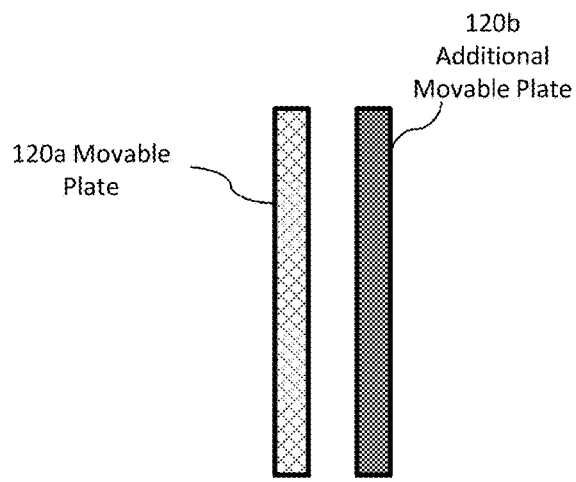
FIGS. 19C, 19D, and 19E schematically illustrate a movable plate and an additional movable plate, in accordance with some embodiments.

FIG. 19C illustrates a movable plate 120a and an additional movable plate 120b. The movable plate 120a and the additional movable plate 120b may be configured to control an exposure of each of the plurality of illumination sources. As described above, the movable plate 120a may be configured to rotate in a different direction and/or at a different rate of rotation than the additional movable plate 120b.

Figure 19D:
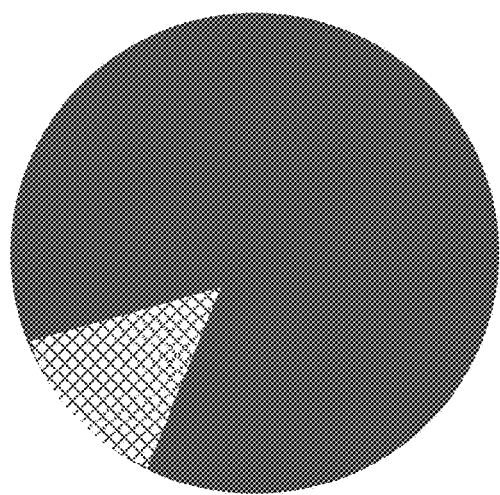
Figure 19E:
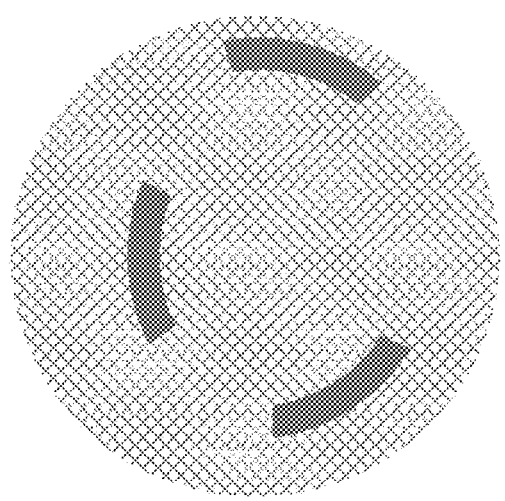

FIG. 19D and FIG. 19E illustrate a top view and a bottom view of the movable plate 120a and the additional movable plate 120b when the respective centers of the movable plate 120a and the additional movable plate 120b are aligned (i.e., lie on a similar axis). As shown in FIG. 19D and FIG. 19E, the movable plate 120a may comprise a first set of cut-outs with a different geometry or arrangement than a second set of cut-outs on the additional movable plate 120b. In such cases, the movable plate 120a and the additional movable plate 120b may be used simultaneously to modulate the length and/or timing of the exposure of the illumination sources in a different manner than if only one movable plate (e.g., either the movable plate 120a or the additional movable plate 120b) were used to modulate the exposure of the illumination sources.

In some embodiments, the medical imaging systems of the present disclosure may comprise one or more optical isolators. An optical isolator may comprise an optical device or component that only allows unidirectional transmission of an optical signal (e.g., one or more light beams or light pulses generated using one or more illumination sources as described herein). The optical isolator may be used to create a more stable coherent light source for imaging. The optical isolator may also be used to avoid unwanted optical reflections and to minimize external optical feedback (e.g., back reflections) that can damage the one or more illumination sources and/or cause instability. The optical isolator may comprise a polarization dependent isolator. Alternatively, the optical isolator may comprise a polarization independent isolator.

In some cases, the optical isolator may be integrated with the one or more illumination sources described elsewhere herein. In such cases, the optical isolator may be disposed on a portion or a structural component of the one or more illumination sources, and may be positioned along a beam path of the one or more illumination sources. In other cases, the optical isolator may be integrated with the movable plate (i.e., the optical chopper) described elsewhere herein. Alternatively, the optical isolator may be disposed between the one or more illumination sources and the movable plate, along a beam path of the one or more illumination sources.

In some embodiments, the medical imaging systems of the present disclosure may comprise one or more bandpass filters. The one or more bandpass filters may be used in combination with any of the illumination sources described herein (e.g., the white light source, the laser light source, the ICG excitation light source, etc.). In some embodiments, the one or more bandpass filters may be used on the ICG excitation lasers to create a narrower laser source around an 808 nanometer (nm) excitation wavelength so that the 808 nm excitation wavelength can be effectively blocked with a notch filter, thereby allowing visualization of only the features in a target region that fluoresce in response to the excitation wavelength.

Figure 20A:
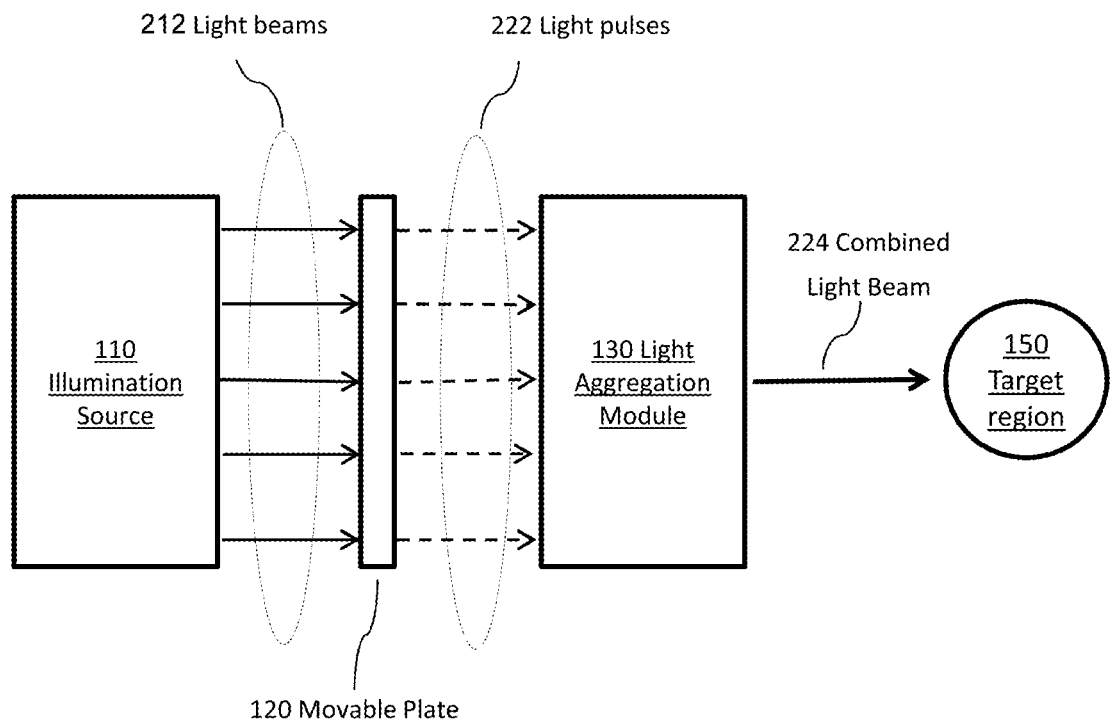
FIG. 20A schematically illustrates a system for illuminating a target region in a subject's body, in accordance with some embodiments.

FIG. 20A illustrates a system for illuminating a target region in a subject's body. The system may comprise a plurality of illumination sources 110. The plurality of illumination sources 110 may be configured to generate one or more light beams 212. The one or more light beams 212 may be directed towards a movable plate 120. In some cases, a subset of the one or more light beams 212 may be directed towards the movable plate 120. The movable plate 120 may be configured to generate one or more light pulses 222 by selectively controlling the exposure of the one or more illumination sources 110 such that one or more light beams 212 are permitted to pass through a cut-out of the movable plate 120 during one or more discrete time intervals. During the one or more discrete time intervals, a subset of the plurality of illumination sources 110 may be optically aligned with a cut-out of the movable plate 120.

The one or more light pulses 222 generated by the movable plate 120 may be aggregated by a light aggregation module 130. The light aggregation module 130 may be configured to receive the one or more light pulses 222. The one or more light pulses 222 may be provided to the light aggregation module 130 via one or more optical fiber bundles. The one or more optical fiber bundles may be configured to receive multiple signals (e.g., light beams 212 or light pulses 222) from multiple illumination sources 110 via multiple separate fibers.

Figure 20B:
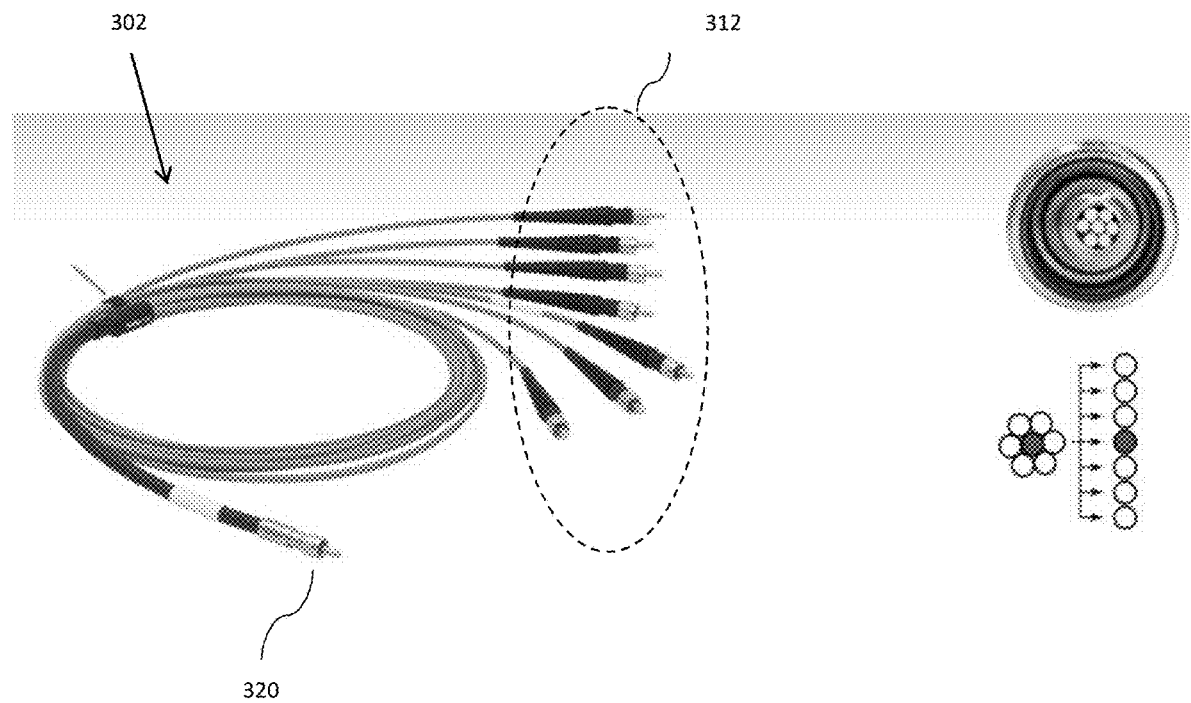
FIG. 20B schematically illustrates a fiber bundle for aggregating light pulses, in accordance with some embodiments.

The aggregation of one or more light pulses may be performed using a bifurcated fiber bundle. FIG. 20B illustrates an example of a bifurcated fiber bundle 302. The bifurcated fiber bundle 302 may comprise a plurality of separate fiber bundles 312 at a first end of the bifurcated fiber bundle 302. Each of the separate fiber bundles 312 at the first end of the bifurcated fiber bundle 302 may be configured to receive one or more light pulses generated using the movable plate and the plurality of illumination sources. The light pulses generated by pulsing each of the plurality of illumination sources may be collimated into one or more fiber bundles of the separate fiber bundles 312. In some cases, one or more light pulses generated using a white light source may also be coupled into a fiber bundle of the separate fiber bundles 312. The separate fiber bundles 312 may be combined and packed into a single fiber bundle 320 located at a second end of the bifurcated fiber bundle 302. The separate fiber bundles 312 may be configured to direct one or more light pulses from a first end of the bifurcated fiber bundle 302 to the single fiber bundle 320 located at the second end of the bifurcated fiber bundle 302. The single fiber bundle 320 may be configured to aggregate and direct the one or more light pulses generated using the movable plate and the plurality of illumination sources to a scope. The single fiber bundle 320 may be directly or indirectly coupled to the scope. The bifurcated fiber bundle 302 may be an N to 1 bifurcated fiber bundle, wherein N is an integer that corresponds to a number of illumination sources within the plurality of illumination sources. N may be at least about 2, 3, 4, 5, 6, 7, 8, 9, 10, or more. In some cases, the bifurcated fiber bundle 302 may be a 5 to 1 bifurcated fiber bundle.

Figure 21:
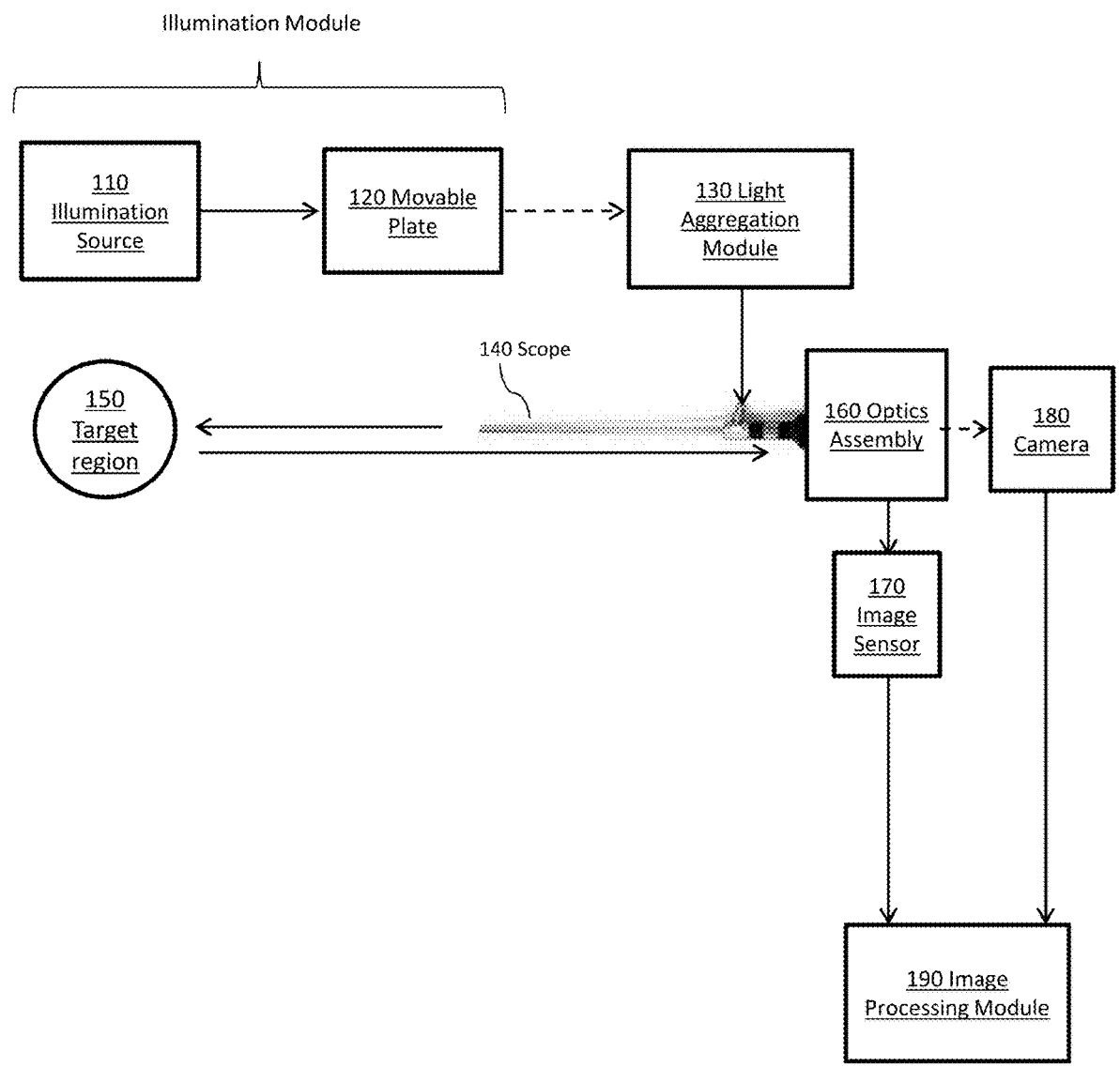
FIG. 21 schematically illustrates a medical imaging system configured to generate an image of a target region illuminated by the plurality of illumination sources, in accordance with some embodiments.

As shown in FIG. 20A and FIG. 21, the light aggregation module 130 may be configured to generate a combined beam 224 based on (a) one or more light beams 212 generated by the plurality of illumination sources and/or (b) one or more light pulses 222 generated by movable plate 120. The combined light beam 224 may be provided to a scope 140. The scope 140 may comprise a laparoscope, an endoscope, a borescope, a videoscope, or a fiberscope. The scope 140 may be insertable into the subject's body and configured to direct the combined light beam 224 onto the target region 150. The scope may be configured to receive, at a distal end of the scope, a reflected light signal that is generated when the combined light signal 224 is emitted onto and reflected from the target region 150. The reflected light signal may comprise a first portion of the reflected light signal and a second portion of the reflected light signal. The first portion of the reflected light signal may comprise deflected light (e.g., backscattered light) that is generated when the target site is illuminated with a first illumination source (e.g., a white light source, a laser light source, or an indocyanine green (ICG) excitation light source). The second portion of the reflected light signal may comprise reflected light that is generated when the target site is illuminated with a second illumination source that is different than the first illumination source.

As shown in FIG. 21, the scope may be configured to direct the reflected light signal from a distal end of the scope 140 to a proximal end of the scope 140 and into an optics assembly 160 located adjacent to the proximal end of the scope. The optics assembly 160 may comprise a beam splitter. The reflected light signal may pass through the beam splitter (e.g., a dichroic mirror). In doing so, the reflected light signal may be separated into the first portion of the reflected light signal and the second portion of the reflected light signal. The first portion may be provided to an image sensor 170 to generate a first image. The second portion may be provided to a camera 180 to generate a second image. The image sensor 170 may be configured to provide the first image to an image processing module 190. The camera 180 may be configured to provide the second image to the image processing module 190. The image processing module 190 may be configured to generate a combined image based on the first image and the second image. The combined image may be an overlaid or superimposed image comprising one or more features from the first image and one or more features from the second image.

Figure 22A:
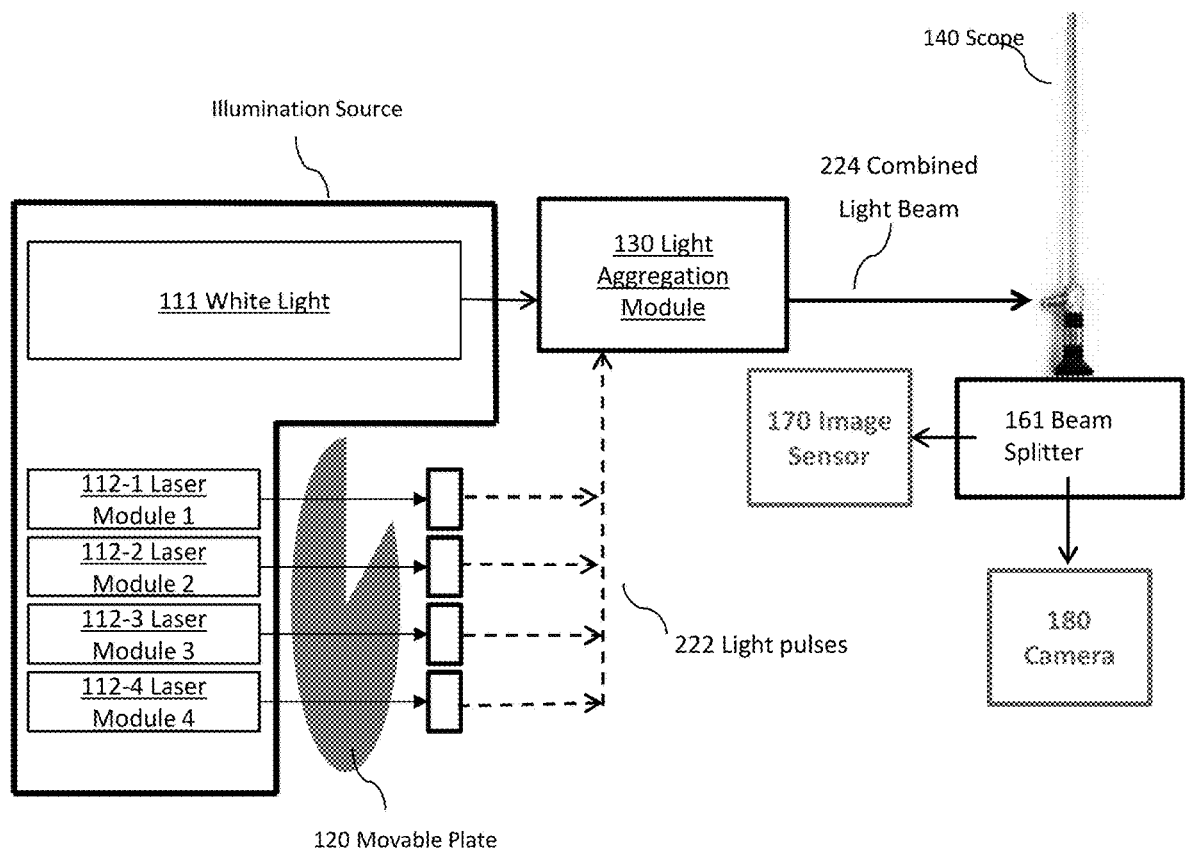
FIGS. 22A and 22B schematically illustrate a movable plate configured to control an exposure of one or more laser light sources, in accordance with some embodiments.
Figure 22B:
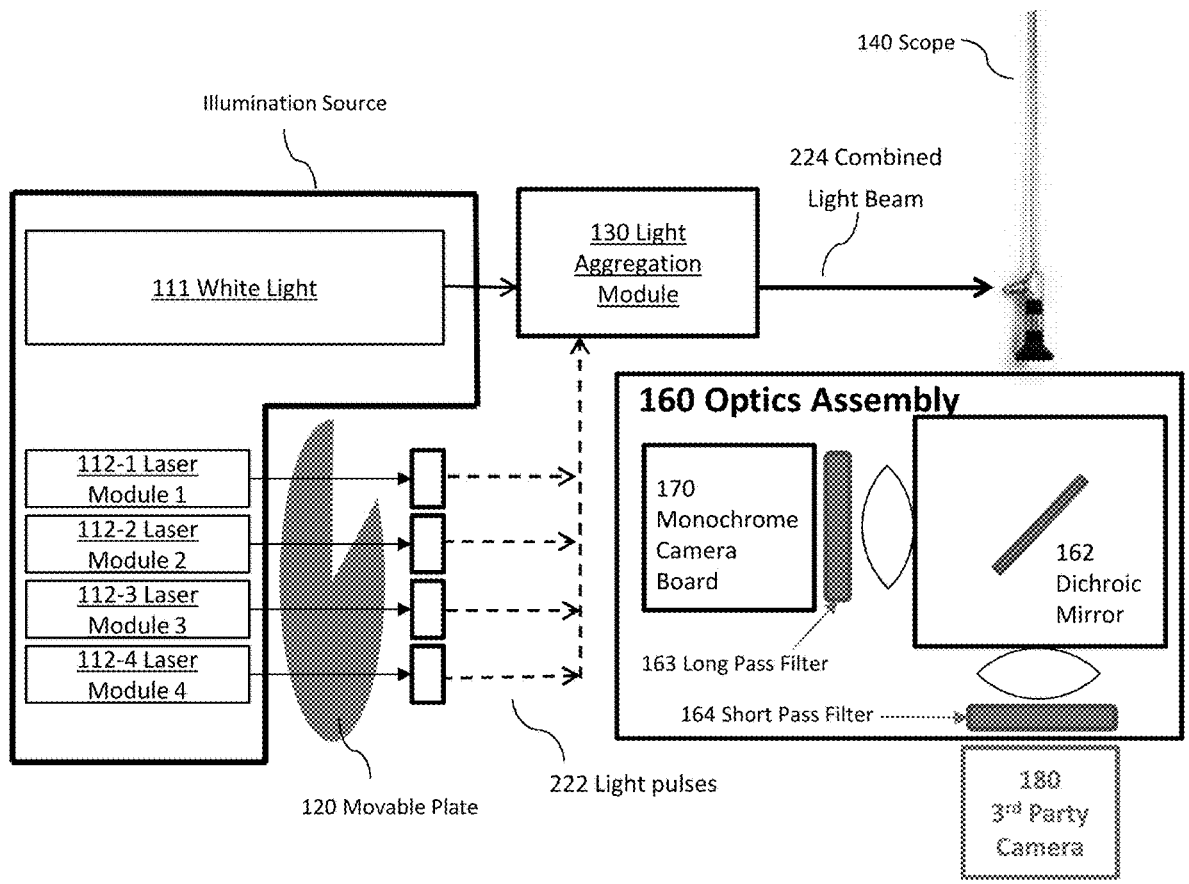

As illustrated in FIGS. 22A and 22B, in some cases, the movable plate 120 may be optically aligned with one or more laser light sources 112-1, 112-2, 112-3, and 112-4. The plurality of illumination sources may comprise the white light source 111 and the one or more laser light sources 112-1, 112-2, 112-3, and 112-4. In such cases, the movable plate 120 and the white light source 111 may not share a common optical axis (i.e., the white light source may be positioned and/or oriented such that a white light beam generated by the white light source does not intersect or coincide with either the movable plate or a cut-out portion of the movable plate). The white light source may be disposed relative to the movable plate such that the white light beam does not pass through the movable plate. The white light beam from the white light source may be transmitted continuously without being affected or separated into pulses by the movable plate. The one or more light pulses generated by the movable plate may be obtained from the one or more laser light beams.

In such cases, the light aggregation module 130 may be configured to (i) combine (a) the one or more light pulses 222 obtained from the one or more laser light beams with (b) the white light beam to generate (c) a combined light beam 224, and (ii) provide the combined light beam 224 to a scope 140, which scope may be insertable into the subject's body and configured to direct the combined light beam 224 onto a target region inside a subject's body.

In any of the embodiments described herein, the light aggregation module may be configured to aggregate two or more light signals. The two or more light signals may comprise light pulses and/or light beams. Aggregating the two or more light signals may involve (i) combining two or more light pulses, (ii) combining two or more light beams, and/or (iii) combining one or more light pulses with one or more light beams. Aggregating the two or more light signals may involve one or more aspects of spectral beam combining. Spectral beam combining may involve combining two or more incoherent signals with non-overlapping optical spectra using a wavelength-sensitive beam combiner (e.g., a prism, a diffraction grating, a dichroic mirror, and/or a volume Bragg grating) that can deflect incident signals (i.e., pulses or beam) according to their respective wavelengths, so that these signals all propagate in the same direction. In some cases, spectral beam combining may be performed using a series of dichroic mirrors configured to reflect a plurality of light beams and/or light pulses along one or more beam paths that may coincide with each other. In such cases, the light beams and/or light pulses may propagate in the same direction.

In some cases, the light aggregation module may be configured to combine a first set of light pulses with a second set of light pulses. In such cases, combining the first set of light pulses and the second set of light pulses may involve sequentially aligning one or more light pulses from either the first set or the second set of light pulses, in a temporal manner. Alternatively, combining the first set of light pulses and the second set of light pulses may involve one or more aspects of coherent beam combining and/or spectral beam combining.

In other cases, the light aggregation module may be configured to combine a first set of light beams with a second set of light beams. In such cases, combining a first set of light beams with a second set of light beams may involve one or more aspects of coherent beam combining and/or spectral beam combining.

As described elsewhere herein, a reflected light signal may be generated when the combined light signal 224 is emitted onto and reflected from the target region. The reflected light signal may comprise a first portion of the reflected light signal and a second portion of the reflected light signal. The first portion of the reflected light signal may comprise deflected light (e.g., backscattered light) that is generated when the target site is illuminated with one or more light pulses obtained from one or more coherent laser light beams generated by the one or more laser light sources. The second portion of the reflected light signal may comprise reflected light that is generated when the target site is illuminated with a white light beam generated by the white light source. The scope 140 may be configured to direct the reflected light signal towards a beam splitter 161. The beam splitter may be configured to separate the reflected light signal into the first portion of the reflected light signal and the second portion of the reflected light signal. The first portion may be provided to an image sensor 170 to generate a first image. The second portion may be provided to a camera 180 to generate a second image. The image sensor 170 may be configured to provide the first image to an image processing module. The camera 180 may be configured to provide the second image to the image processing module. The image processing module may be configured to generate a combined image based on the first image and the second image.

FIG. 22B illustrates an optics assembly 160 that may be configured to receive the reflected light signal. The optics assembly 160 may comprise a dichroic mirror 162. In some cases, the dichroic mirror may be interchanged with a beam splitter, a half mirror, a dichroic beam splitter, or a multi-band beam splitter. The dichroic mirror 162 may be configured to receive the reflected light signal from the target site and (i) reflect the first portion of the light signals that is in a first electromagnetic spectral range toward an image sensor 170, and (ii) permit the second portion of the light signals in a second electromagnetic spectral range to pass through towards a camera 180. The camera 180 may or may not be integrated with the optics assembly 160. The optics assembly 160 may comprise a long pass filter 163. The long pass filter 163 may be positioned adjacent to and/or in front of the image sensor 170. The image sensor may be a monochrome camera board. The optics assembly 160 may comprise a short pass filter 164. The short pass filter 164 may be positioned adjacent to and/or in front of the camera 180.

Figure 23A:
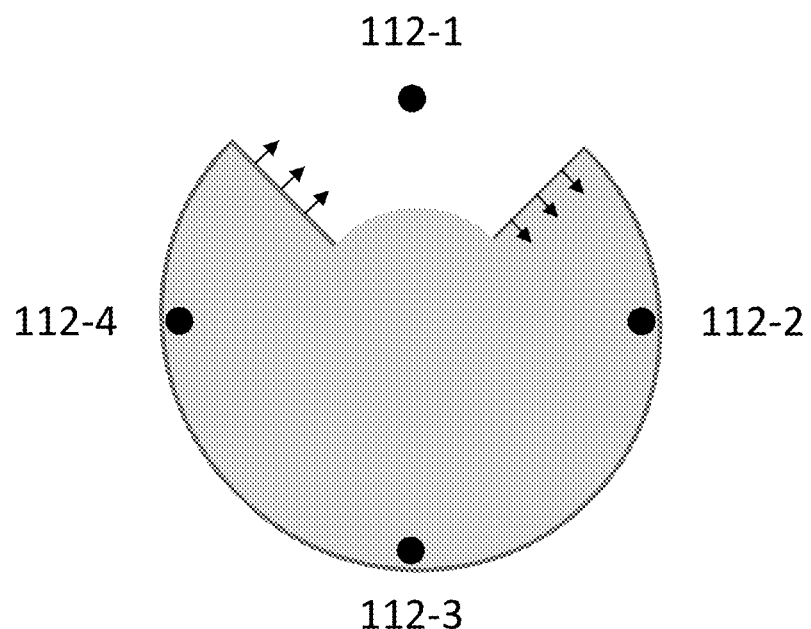
FIGS. 23A and 23B schematically illustrate an exposure of one or more laser light sources that are optically aligned with the movable plate, in accordance with some embodiments.

FIG. 23A illustrates a synchronization of (i) the exposure of one or more laser light sources 112-1, 112-2, 112-3, and 112-4 through the movable plate 120 with (ii) one or more camera frames captured by the image sensor or the camera. The movable plate 120 may comprise a single notch. The camera frames may be acquired at 120 frames per second (FPS). Each laser light source 112-1, 112-2, 112-3, and 112-4 may be exposed at a frequency of 30 hertz (Hz). In such cases, the movable plate 120 may rotate at about 1800 rotations per minutes (RPM).

Figure 23B:
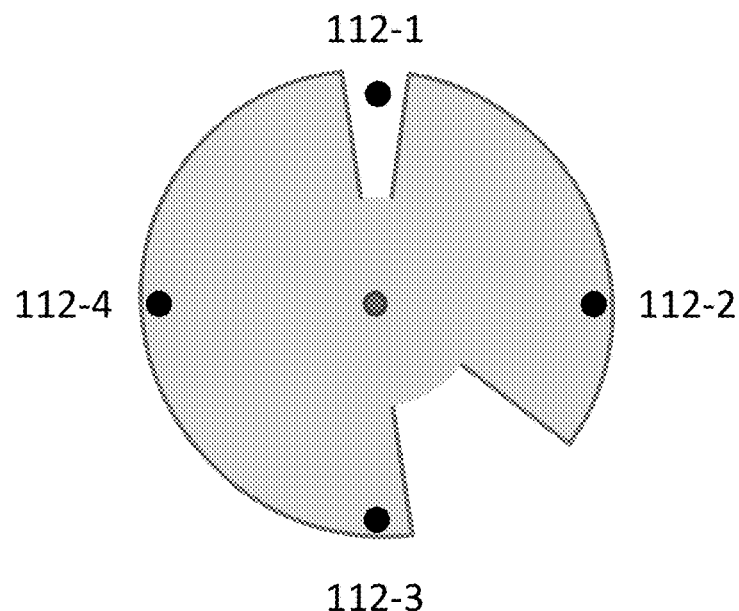

FIG. 23B illustrates a synchronization of (i) the exposure of one or more laser light sources 112-1, 112-2, 112-3, and 112-4 through the movable plate 120 with (ii) one or more camera frames captured by the image sensor or the camera. The movable plate 120 may comprise two distinct notches with different shapes and/or geometries. Each of the two distinct notches may provide different exposure times for each of the laser light sources 112-1, 112-2, 112-3, and 112-4. The camera frames may be acquired at 120 frames per second (FPS). For each revolution of the movable plate, each laser light source 112-1, 112-2, 112-3, and 112-4 may be (i) exposed through a first notch of the movable plate for a first exposure time and (ii) a second notch of the movable plate for a second exposure time. The movable plate 120 may be configured to rotate at about 900 rotations per minutes (RPM).

In some cases, the movable plate may be optically aligned with both (i) the white light source and (ii) the one or more laser light sources. The plurality of illumination sources may comprise the white light source and the one or more laser light sources. In such cases, the one or more light pulses generated by the movable plate may be obtained from (i) the white light beam and (ii) the one or more laser light beams.

In such cases, the light aggregation module may be configured to (i) combine (a) the one or more light pulses obtained from the white light beam with (b) the one or more light pulses obtained from the one or more laser light beams, to generate (c) a combined light beam, and (ii) provide the combined light beam to a scope. The scope may be insertable into the subject's body and configured to direct the combined light beam onto the target region.

Figure 24A:
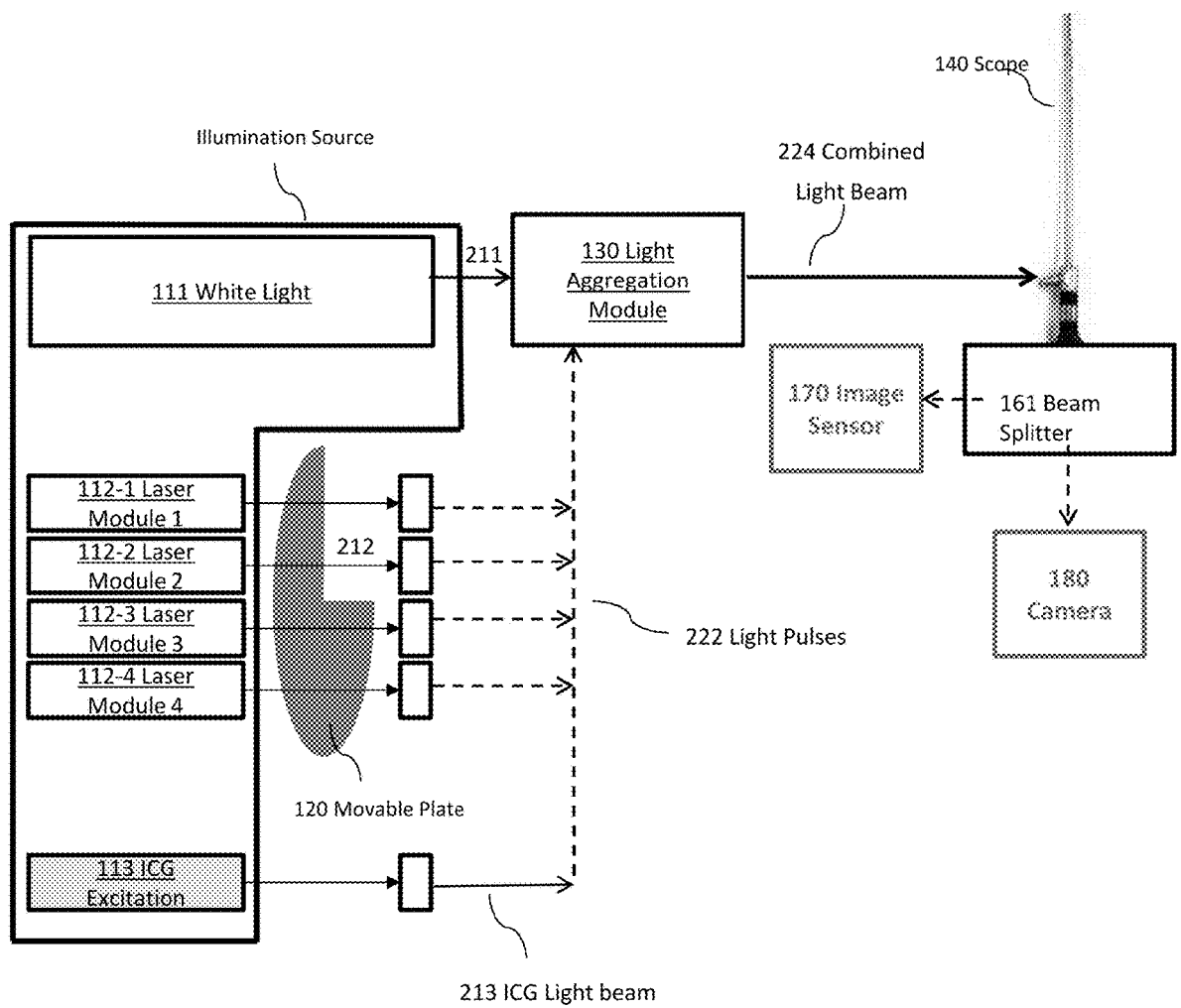
FIGS. 24A and 24B schematically illustrate an indocyanine green (ICG) excitation light source that is not optically aligned with a movable plate, in accordance with some embodiments.
Figure 24B:
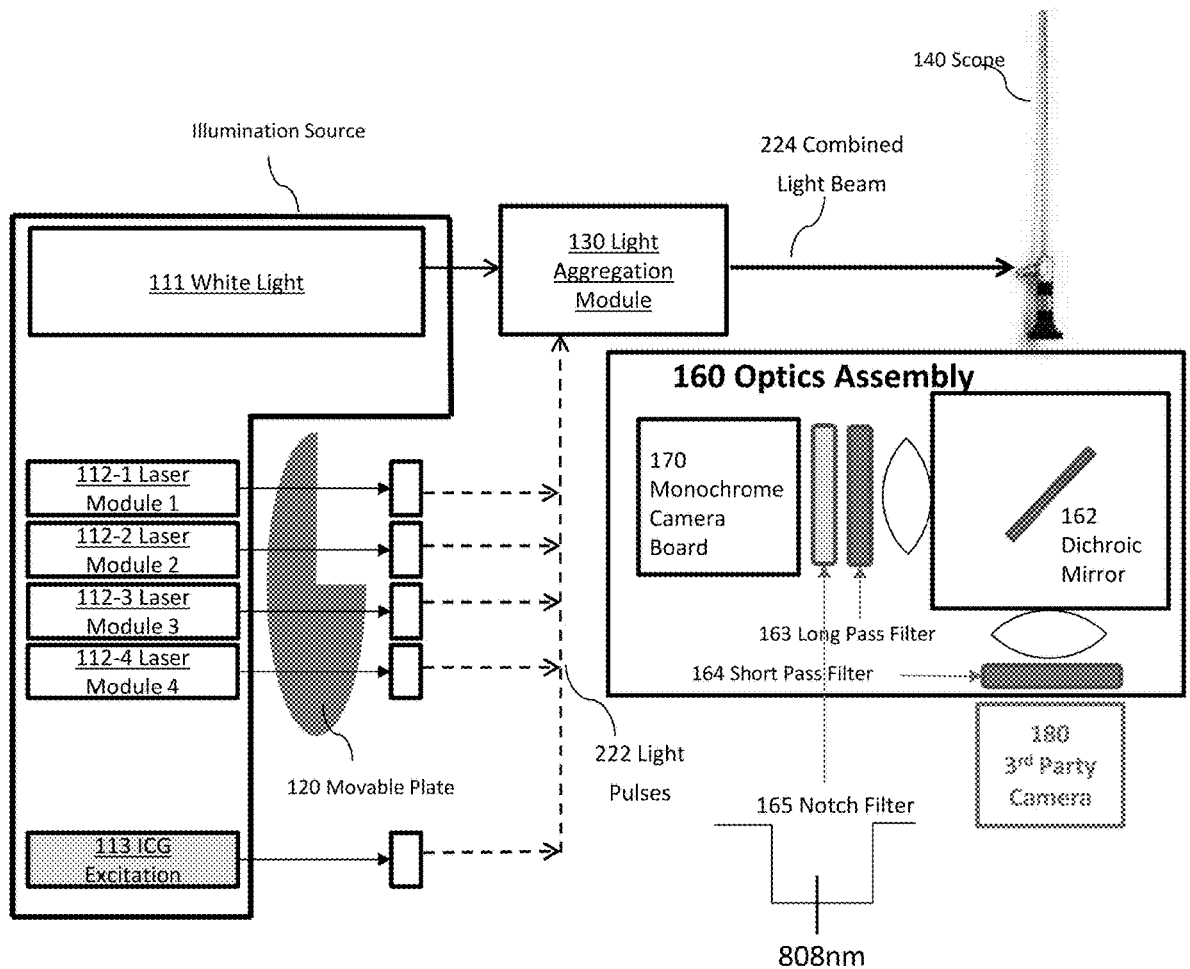

As illustrated in FIGS. 24A-24B, in some cases, the movable plate 120 may be optically aligned with (i) the one or more laser light sources 112-1, 112-2, 112-3, and 112-4. The plurality of illumination sources may comprise the white light source 111, the one or more laser light sources 112-1, 112-2, 112-3, and 112-4, and the ICG excitation light source 113. In such cases, the movable plate 120 and the white light source 111 may not share a common optical axis. The white light beam from the white light source may be transmitted continuously without being affected or separated into pulses by the movable plate. Further, the movable plate 120 and the ICG excitation light source 113 may not share a common optical axis. The ICG excitation light beam 213 from the ICG excitation light source 113 may be transmitted continuously without being affected or separated into pulses by the movable plate 120. The one or more light pulses 222 generated by the movable plate 120 may be obtained from (i) the one or more laser light beams 212.

In such cases, the light aggregation module 130 may be configured to (i) combine (a) the one or more light pulses 222 obtained from the one or more laser light beams 212 with (b) at least one of the white light beam 211 or the ICG excitation light beam 213 to generate (c) a combined light beam 224, and (ii) provide the combined light beam 224 to a scope 140. The scope may be insertable into the subject's body and configured to direct the combined light beam onto a target region within the subject's body.

As described above, a reflected light signal may be generated when the combined light signal 224 is emitted onto and reflected from the target region. The reflected light signal may comprise a first portion of the reflected light signal and a second portion of the reflected light signal. The first portion of the reflected light signal may comprise deflected light that is generated when the target site is illuminated with one or more light pulses obtained from the one or more laser light beams 212. The second portion of the reflected light signal may comprise reflected light that is generated when the target site is illuminated with a different light (e.g., a white light beam 211 or an ICG excitation light beam 213). The scope 140 may be configured to direct the reflected light signal towards a beam splitter 161. The beam splitter may be configured to separate the reflected light signal into the first portion of the reflected light signal and the second portion of the reflected light signal. The first portion may be provided to an image sensor 170 to generate a first image. The second portion may be provided to a camera 180 to generate a second image. The image sensor 170 may be configured to provide the first image to an image processing module. The camera 180 may be configured to provide the second image to the image processing module. The image processing module may be configured to generate a combined image based in part on the first image and/or the second image.

FIG. 24B illustrates an optics assembly 160 that may be configured to receive the reflected light signal. The optics assembly 160 may comprise a dichroic mirror 162. In some cases, the dichroic mirror may be interchanged with a beam splitter, a half mirror, a dichroic beam splitter, or a multi-band beam splitter. The dichroic mirror 162 may be configured to receive the reflected light signal from the target site and (i) reflect the first portion of the light signals that is in a first electromagnetic spectral range toward an image sensor 170, and (ii) permit the second portion of the light signals in a second electromagnetic spectral range to pass through toward a camera 180. The camera 180 may or may not be integrated with the optics assembly 160. The optics assembly 160 may comprise a long pass filter 163. The long pass filter 163 may be positioned adjacent to and/or in front of the image sensor 170. The image sensor may be a monochrome camera board. The optics assembly 160 may comprise a short pass filter 164. The short pass filter 164 may be positioned adjacent to and/or in front of the camera 180. The optics assembly may comprise a notch filter 165. The notch filter 165 may have a notch width of approximately 808 nanometers (nm). The notch filter may be positioned between the long pass filter 163 and the image sensor 170.

Figure 25:
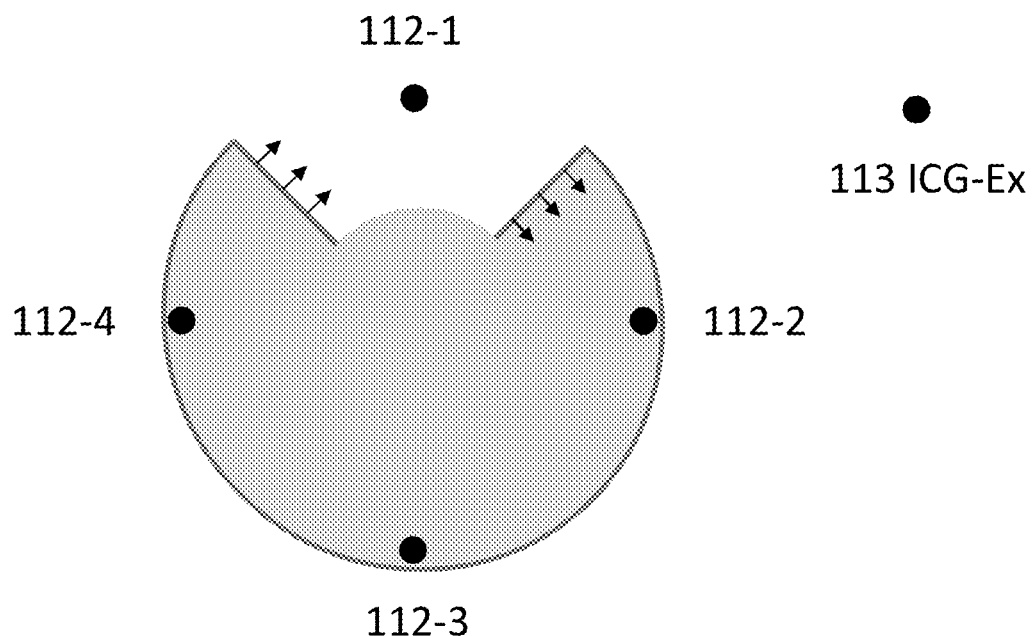
FIG. 25 schematically illustrates an exposure of one or more laser light sources and an ICG excitation light source that is not optically aligned with the movable plate, in accordance with some embodiments.

FIG. 25 illustrates a synchronization of (i) the exposure of one or more laser light sources 112-1, 112-2, 112-3, and 112-4 through the movable plate 120 with (ii) one or more camera frames captured by the image sensor or the camera. The plurality of illumination sources may include an indocyanine green (ICG) excitation light source 113 that is not optically aligned with the movable plate. The movable plate 120 may comprise a single notch. The imaging device may be configured to capture a first set of camera frames based on the exposure of the one or more laser light sources. Afterwards, the one or more laser light sources may be turned off, and the ICG excitation light source may be turned on. The imaging device may be configured to capture a second set of camera frames based on one or more ICG excitation light beams generated by the ICG excitation light source. The first set of camera frames and the second set of camera frames may be acquired at 120 frames per second (FPS). ICG emission characteristics (e.g., fluorescence caused by the interaction of one or more dyes with the ICG excitation light beam) may be imaged in any camera frames where the ICG excitation light source is turned on and/or enabled.

Figure 26A:
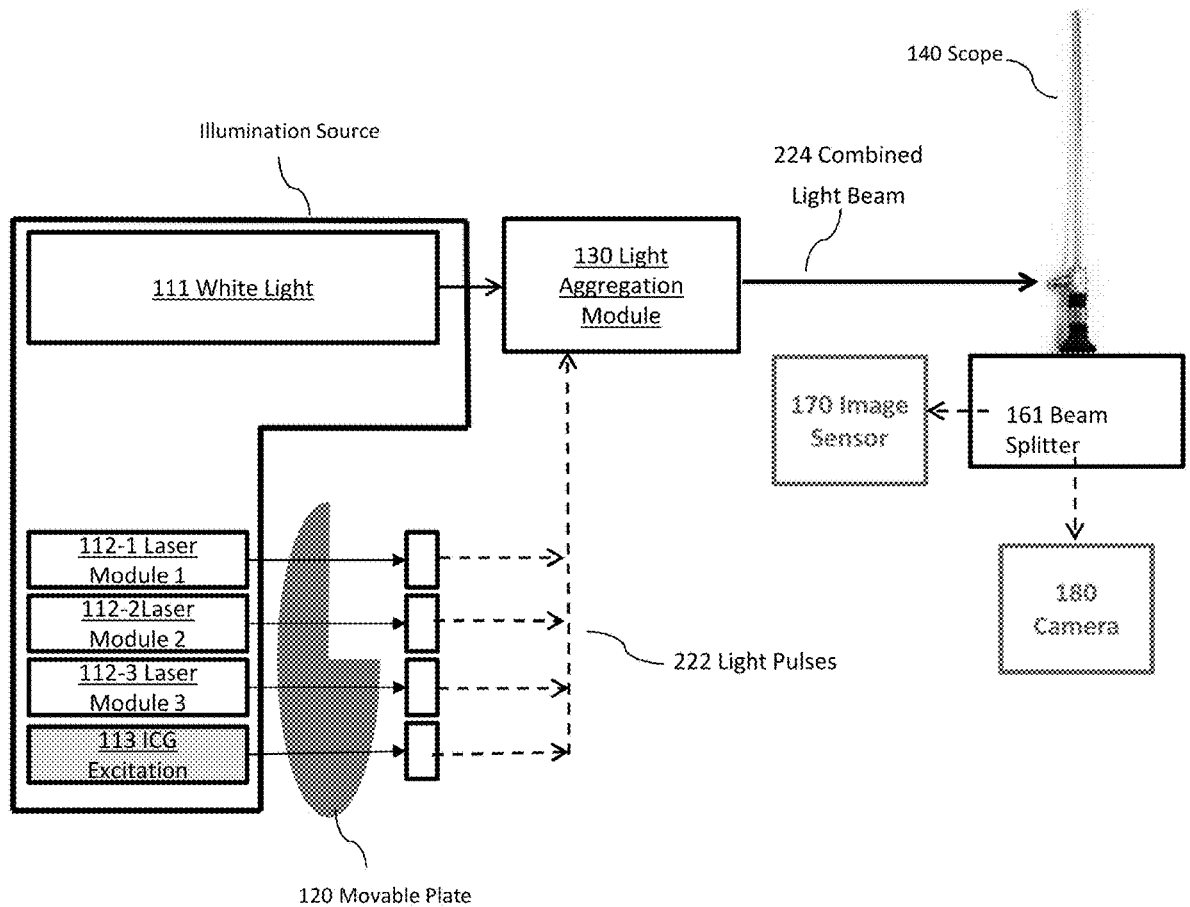
FIGS. 26A and 26B schematically illustrate a movable plate configured to control an exposure of an ICG excitation light source and one or more laser light sources, in accordance with some embodiments.
Figure 26B:
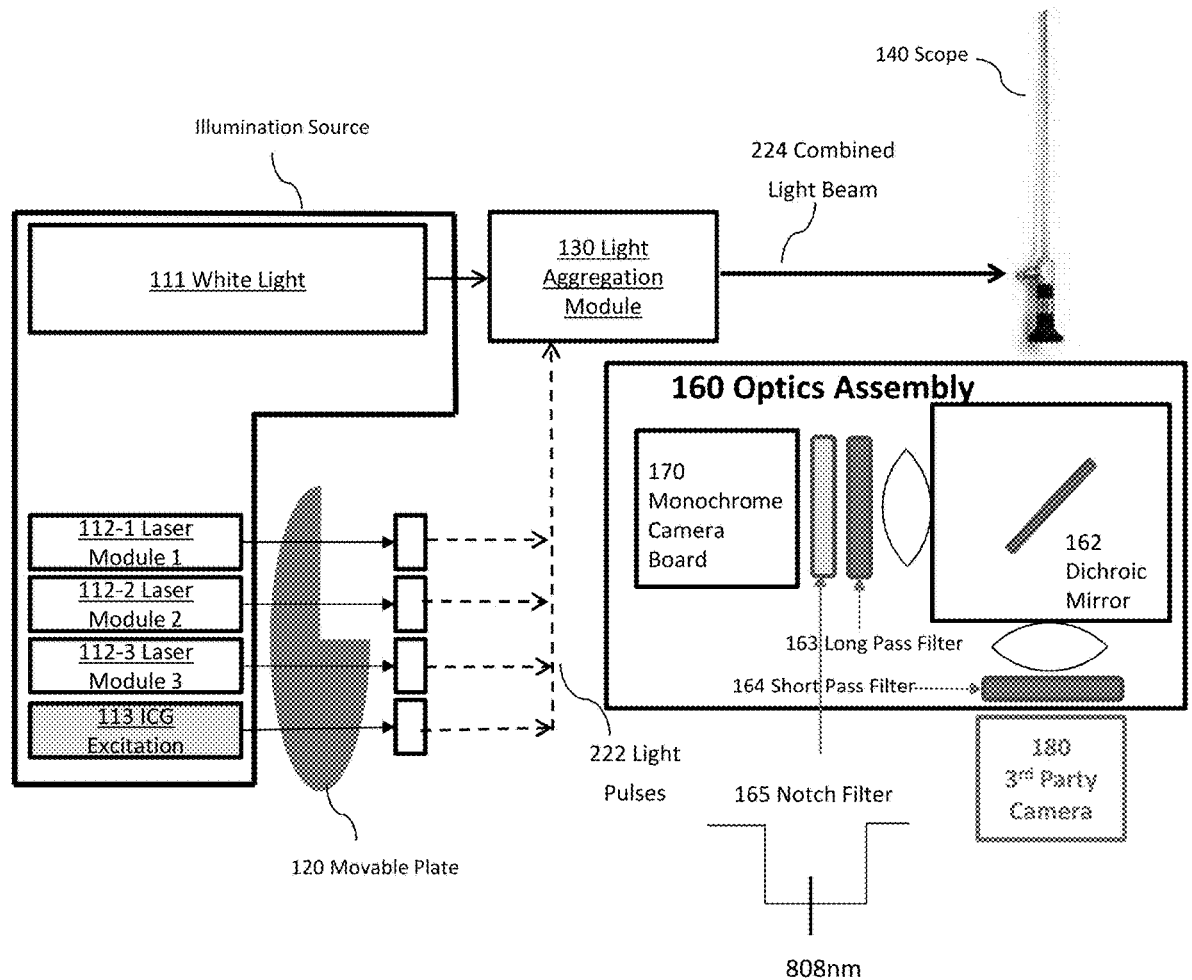

As illustrated in FIGS. 26A-26B, in some cases, the movable plate 120 may be optically aligned with (i) the one or more laser light sources 112-1, 112-2, and 112-3 and (ii) the ICG excitation light source 113. The plurality of illumination sources may comprise the white light source 111, the one or more laser light sources 112-1, 112-2, and 112-3, and the ICG excitation light source 113. In such cases, the movable plate and the white light source may not share a common optical axis. The white light beam from the white light source may be transmitted continuously without being affected or separated into pulses by the movable plate. The one or more light pulses 222 generated by the movable plate 120 may be obtained from (i) the one or more laser light beams and (ii) the ICG excitation light beam.

In such cases, the light aggregation module 130 may be configured to (i) combine (a) the one or more light pulses 222 obtained from the one or more laser light beams and the ICG excitation light beam with (b) the white light beam to generate (c) a combined light beam 224, and (ii) provide the combined light beam 224 to a scope 140. The scope may be insertable into the subject's body and configured to direct the combined light beam onto the target region.

As described above, a reflected light signal may be generated when the combined light signal 224 is emitted onto and reflected from the target region. The reflected light signal may comprise a first portion of the reflected light signal and a second portion of the reflected light signal. The first portion of the reflected light signal may comprise deflected light (e.g., backscattered light) that is generated when the target site is illuminated with one or more light pulses 222 obtained from one or more light beams generated by the laser light sources 112-1, 112-2, 112-3 and/or the ICG excitation light source 113. The second portion of the reflected light signal may comprise reflected light that is generated when the target site is illuminated with a different light (e.g., the white light beam). The scope 140 may be configured to direct the reflected light signal towards a beam splitter 161. The beam splitter may be configured to separate the reflected light signal into the first portion of the reflected light signal and the second portion of the reflected light signal. The first portion may be provided to an image sensor 170 to generate a first image. The second portion may be provided to a camera 180 to generate a second image. The image sensor 170 may be configured to provide the first image to an image processing module. The camera 180 may be configured to provide the second image to the image processing module. The image processing module may be configured to generate a combined image based on the first image and the second image.

FIG. 26B illustrates an optics assembly 160 that may be configured to receive the reflected light signal. The optics assembly 160 may comprise a dichroic mirror 162. In some cases, the dichroic mirror may be interchanged with a beam splitter, a half mirror, a dichroic beam splitter, or a multi-band beam splitter. The dichroic mirror 162 may be configured to receive the reflected light signal from the target site and (i) reflect the first portion of the light signals that is in a first electromagnetic spectral range toward an image sensor 170, and (ii) permit the second portion of the light signals in a second electromagnetic spectral range to pass through toward a camera 180. The camera 180 may or may not be integrated with the optics assembly 160. The optics assembly 160 may comprise a long pass filter 163. The long pass filter 163 may be positioned adjacent to and/or in front of the image sensor 170. The image sensor may be a monochrome camera board. The optics assembly 160 may comprise a short pass filter 164. The short pass filter 164 may be positioned adjacent to and/or in front of the camera 180. The optics assembly may comprise a notch filter 165. The notch filter 165 may have a notch width of approximately 808 nanometers (nm). The notch filter may be positioned between the long pass filter 163 and the image sensor 170.

Figure 27:
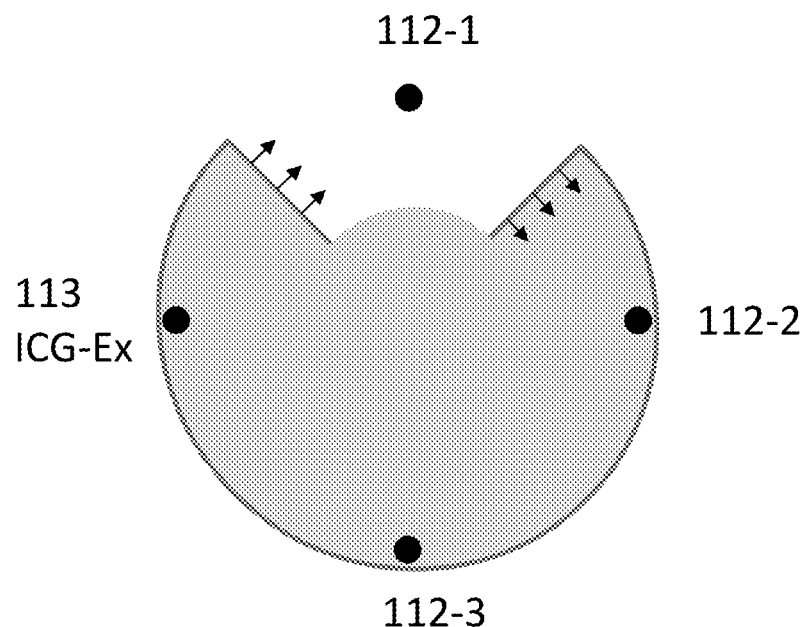
FIG. 27 schematically illustrates an exposure of one or more laser light sources and an ICG excitation light source that is optically aligned with the movable plate, in accordance with some embodiments.

FIG. 27 illustrates a synchronization of (i) the exposure of (a) one or more laser light sources 112-1, 112-2, 112-3 and (b) an ICG excitation light source 113 with (ii) the acquisition of one or more camera frames captured by the image sensor or the camera. The one or more laser light sources and the ICG excitation light source may be optically aligned with the movable plate. The movable plate 120 may comprise a single notch. The imaging device may be configured to capture a first set of camera frames based on the exposure of the one or more laser light sources. The imaging device may be configured to capture a second set of camera frames based on the controlled exposure of the ICG excitation light source. The first set of camera frames may be acquired at 120 frames per second (FPS). The second set of camera frames may be acquired at 30 frames per second (FPS). The second set of camera frames may capture one or more ICG emission characteristics (e.g., fluorescence caused by the interaction of one or more dyes with the ICG excitation light beam). The second set of camera frames may be imaged in 1/N frames, wherein N may correspond to the number of laser light sources optically aligned with the movable plate 120.

In some cases, the movable plate may be optically aligned with (i) the one or more laser light sources and (ii) the white light source. The plurality of illumination sources may comprise the white light source, the one or more laser light sources, and the ICG excitation light source. In such cases, the movable plate and the ICG excitation light source may not share a common optical axis. The ICG excitation light beam from the ICG excitation light source may be transmitted continuously without being affected or separated into pulses by the movable plate. The one or more light pulses generated by the movable plate may be obtained from (i) the one or more laser light beams and (ii) the white light beam.

In such cases, the light aggregation module may be configured to (i) combine (a) the one or more light pulses obtained from the one or more laser light beams and the white light beam with (b) the ICG excitation light beam to generate (c) a combined light beam, and (ii) provide the combined light beam to a scope. The scope may be insertable into the subject's body and configured to direct the combined light beam onto the target region.

In some cases, the movable plate may be optically aligned with (i) the one or more laser light sources, (ii) the white light source, and (iii) the ICG excitation light source. In such cases, the one or more light pulses generated by the movable plate may be obtained from (i) the one or more laser light beams, (ii) the white light beam, and (iii) the ICG excitation light beam. Further, the light aggregation module may be configured to (i) combine (a) the one or more light pulses obtained from the one or more laser light beams with (b) the one or more light pulses obtained from the white light beam and the ICG excitation light beam to generate (c) a combined light beam, and (ii) provide the combined light beam to a scope. The scope may be insertable into the subject's body and configured to direct the combined light beam onto the target region.

Figure 28A:
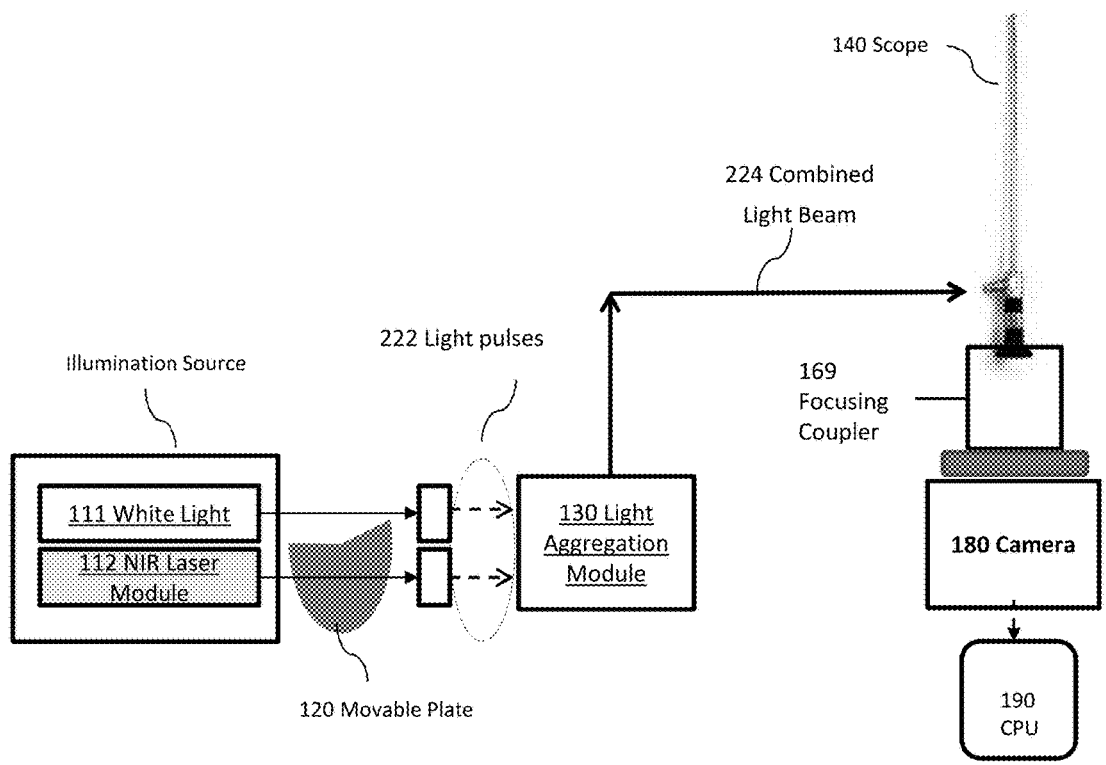
FIGS. 28A and 28B schematically illustrate a movable plate configured to control an exposure of a white light source and one or more laser light sources, in accordance with some embodiments.
Figure 28B:
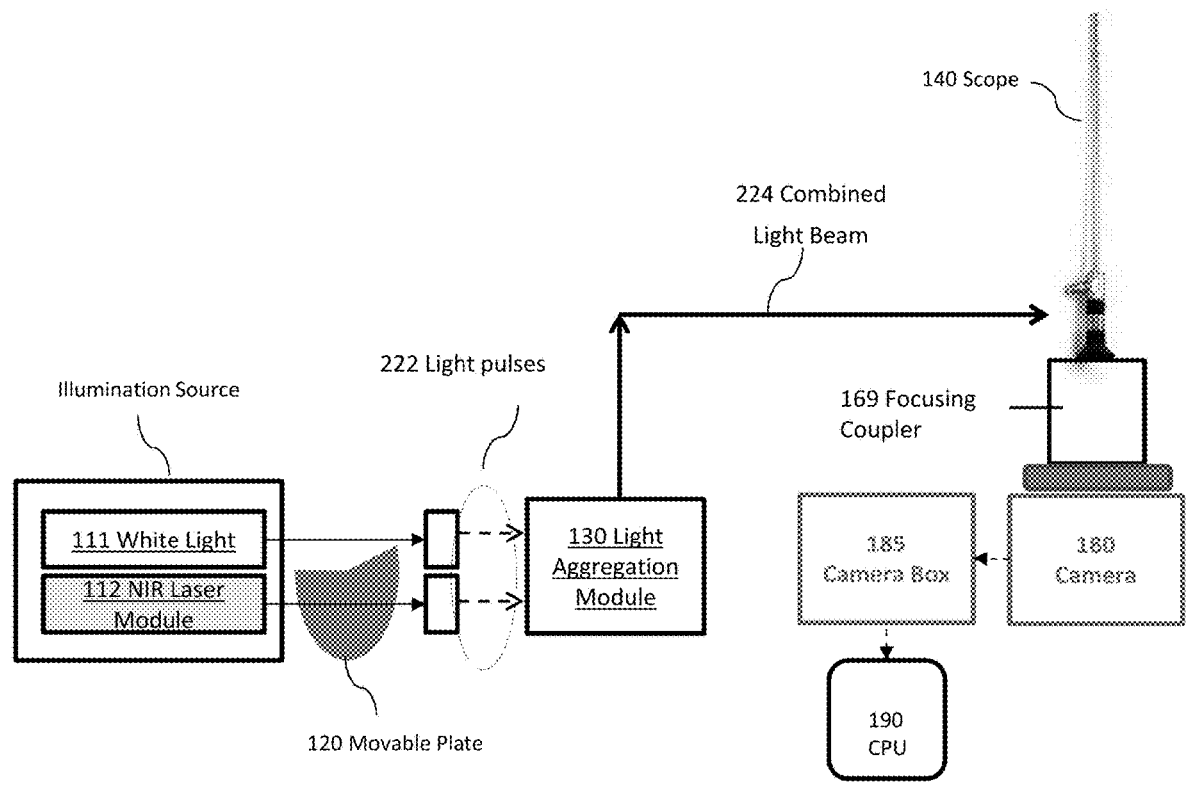

FIGS. 28A and 28B illustrate a white light source 111 and a laser light source 112 optically aligned with a movable plate 120. The white light source 111 and a laser light source 112 may be operated simultaneously and continuously. The white light source may be used to recover a standard color image and/or video of the target region. The laser light source may be used for laser speckle contrast imaging of the target region. The movable plate 120 may be configured to generate one or more light pulses 222 by controlling the exposure of the white light source 111 and the laser light source 112. The light aggregation module 130 may be configured to combine one or more sets of light pulses associated with the white light source 111 with one or more sets of light pulses associated with the laser light source 112 to generate a combined light beam 224. The combined light beam 224 may be provided to a scope 140, which scope may be configured to direct the combined light beam 224 to a target region in a subject's body.

A reflected light signal may be generated when the combined light signal 224 is emitted onto and reflected from the target region. The reflected light signal may comprise a first portion of the reflected light signal and a second portion of the reflected light signal. The first portion of the reflected light signal may comprise deflected light (e.g., backscattered light) that is generated when the target site is illuminated with one or more light pulses 222 obtained from one or more laser light beams generated by the laser light source 112. The second portion of the reflected light signal may comprise reflected light that is generated when the target site is illuminated with one or more light pulses 222 obtained from one or more white light beams generated by the white light source 111. The scope 140 may be configured to direct the reflected light signal towards an optics assembly. The optics assembly may comprise a focusing coupler 169. The focusing coupler may be configured to focus, modulate, and/or direct the first portion of the reflected light signal and/or the second portion of the reflected light signal to a camera 180. The camera may be configured to generate a combined image of the target region based on the first portion of the reflected light signal and the second portion of the reflected light signal. In some cases, the camera may be configured to provide the combined image, the first portion of the reflected light signal, and/or the second portion of the reflected light signal to a camera box 185. The camera box 185 may be configured to pre-process and/or modify the combined image, the first portion of the reflected light signal, and/or the second portion of the reflected light signal. The camera box 185 may be configured to provide the pre-processed image, the first portion of the reflected light signal, and/or the second portion of the reflected light signal to a central processing unit (CPU) 190. The CPU 190 may be configured to generate a modified and/or an overlaid (i.e., superimposed) image of the target region based on the first portion of the reflected light signal and/or the second portion of the reflected light signal.

As illustrated in FIGS. 28A and 28B, the camera 180 may be configured to capture a first set of frames associated with the white light source 111, and a second set of frames associated with the laser light source 112. The frames captured by the camera 180 may alternate between a frame from the first set of frames and a frame from the second set of frames. The exposure of the white light source 111 may be synchronized with the acquisition of one or more even-numbered frames. The exposure of the laser light source 112 may be synchronized with the acquisition of one or more odd-numbered frames. The camera 180 may be configured to capture frames at 120 frames per second. The camera 180 may be configured to capture 60 frames per second for the white light source 111 and another 60 frames per second for the laser light source 112.

In some cases, the camera 180 and/or the camera box 185 may be configured to calibrate for phase delay between the generation of one or more light pulses and the acquisition of one or more frames. In such cases, the camera 180 and/or the camera box 185 may be configured to (i) turn off one or more illumination sources and (ii) tunes, sweep, and/or optimize one or more delay parameters for the movable plate, until even-numbered frames are completely dark and odd-numbered frames are bright.

Figure 29:
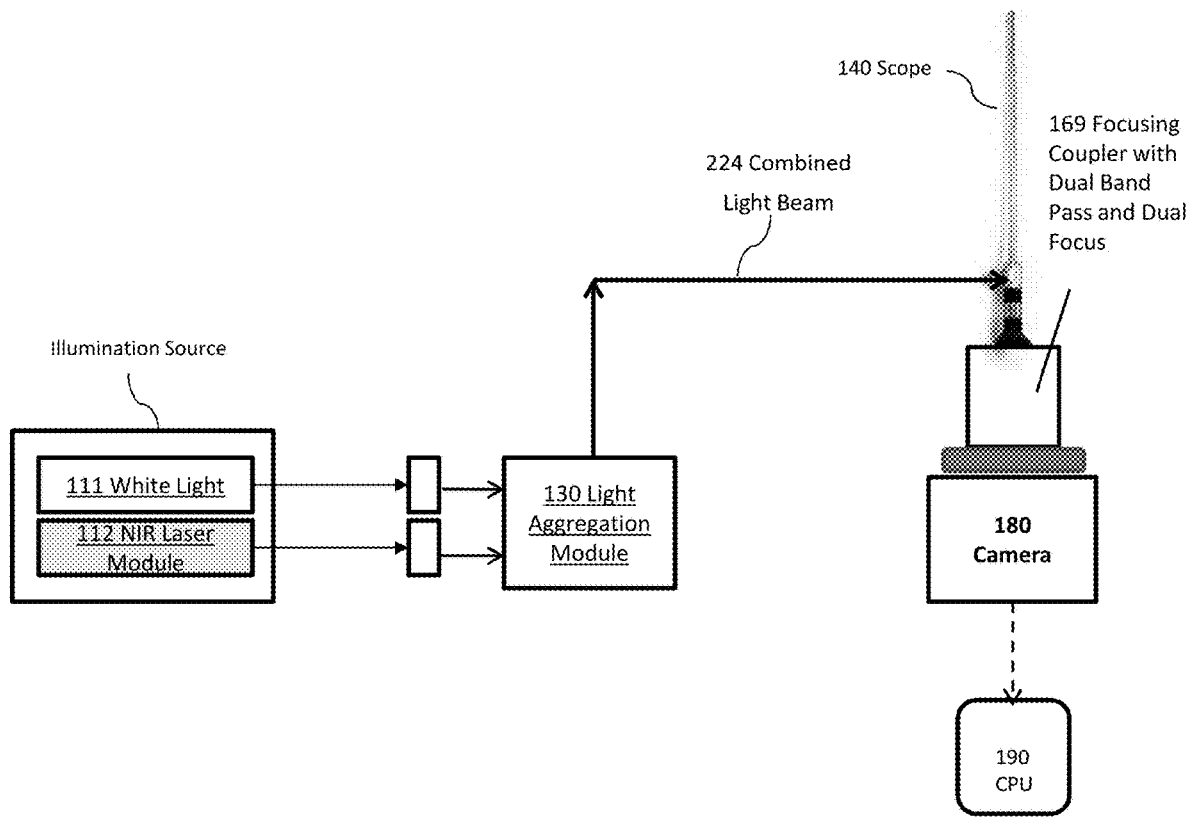
FIG. 29 schematically illustrates a light aggregation module configured to combine one or more light beams generated by a white light source and a laser light source, in accordance with some embodiments.

FIG. 29 illustrates a light aggregation module 130 configured to (a) aggregate a white light beam generated by a white light source 111 and a laser light beam generated by a laser light source 112 to (b) generate a combined light beam 224. The combined light beam 224 may be provided to a scope 140, which scope may be configured to direct the combined light beam 224 to a target region in a subject's body. The laser light beam and the white light beam may be transmitted as continuous beams with stable output power.

A reflected light signal may be generated when the combined light signal 224 is emitted onto and reflected from the target region. The reflected light signal may comprise a first portion of the reflected light signal and a second portion of the reflected light signal. The first portion of the reflected light signal may comprise deflected light (e.g., backscattered light) that is generated when the target site is illuminated with one or more laser light beams generated by the laser light source 112. The second portion of the reflected light signal may comprise reflected light that is generated when the target site is illuminated with one or more white light beams generated by the white light source 111. The scope 140 may be configured to direct the reflected light signal towards an optics assembly. The optics assembly may comprise a focusing coupler 169. The focusing coupler 169 may be configured to focus, modulate, and/or direct the first portion of the reflected light signal and/or the second portion of the reflected light signal to a camera 180. The focusing coupler 169 may comprise dual band pass filters and dual focusing elements. The camera 180 may be configured to generate a combined image of the target region based on the first portion of the reflected light signal and the second portion of the reflected light signal. In some cases, the camera may be configured to provide the combined image, the first portion of the reflected light signal, and/or the second portion of the reflected light signal to a CPU 190. The CPU 190 may be configured to process and/or modify the combined image, the first portion of the reflected light signal, and/or the second portion of the reflected light signal. The CPU 190 may be configured to generate a modified and/or an overlaid (i.e., superimposed) image of the target region based on the first portion of the reflected light signal and the second portion of the reflected light signal.

In another aspect, the present disclosure provides a system for illuminating a target region of a subject's body. The system may comprise a plurality of illumination sources comprising at least two of (i) a white light source configured to generate a white light beam and (ii) one or more light emitting diodes (LEDs) or laser light sources configured to generate one or more laser light beams; and a movable plate comprising one or more cut-outs. The movable plate may be optically aligned with one or more of the plurality of illumination sources and configured to (i) move relative to the one or more illumination sources and (ii) control a pulsing of the one or more illumination sources in synchronization with a pre-determined frame capture rate. In some cases, the movable plate may be configured to control the pulsing of the one or more illumination sources by adjusting one or more time intervals during which each of the plurality of illumination sources is optically aligned with the one or more cut-outs of the movable plate.

In another aspect, the present disclosure provides methods for illuminating a target region in a subject's body. The method may comprise: providing a plurality of illumination sources comprising (i) a white light source configured to generate a white light beam and (ii) one or more laser light sources configured to generate one or more laser light beams; directing one or more light beams generated by the plurality of illumination sources towards a movable plate comprising one or more cut-outs, wherein the movable plate is (i) optically aligned with one or more of the plurality of illumination sources, and (ii) configured to move so as to (a) control an exposure of the one or more illumination sources through the one or more cut-outs, relative to a pre-determined frame capture rate, and (b) generate one or more light pulses based on the controlled exposure of the one or more illumination sources; and providing the one or more light pulses to a light aggregation module, wherein the light aggregation module is configured to (i) combine the one or more light pulses obtained from each of the one or more light beams generated by the plurality of illumination sources to generate a combined light beam, and (ii) provide the combined light beam to a scope, wherein the scope is insertable into the subject's body and configured to direct the combined light beam onto the target region. In some cases, the plurality of illumination sources may further comprise an indocyanine green (ICG) excitation light source configured to generate an ICG excitation light beam.

Figure 30:
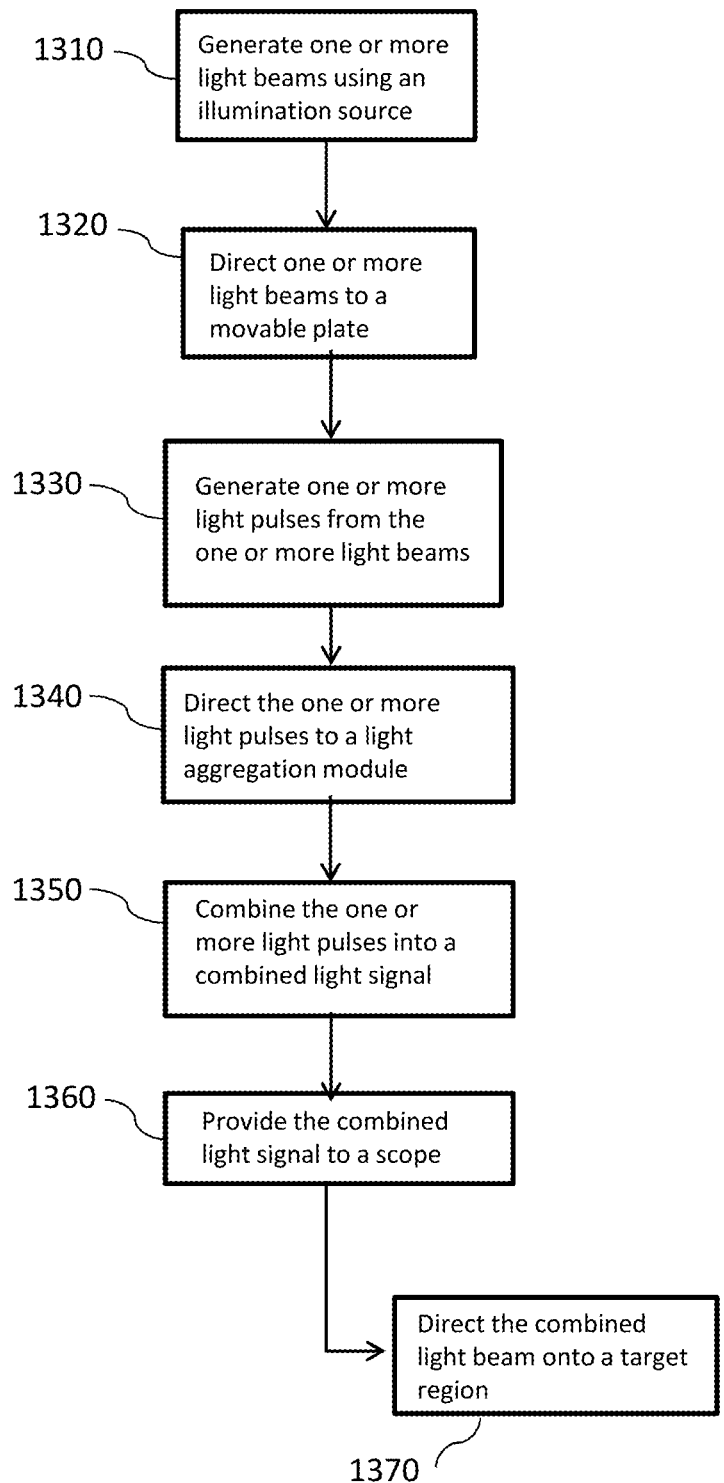
FIG. 30 schematically illustrates a method for illuminating a target region in a subject's body, in accordance with some embodiments.

FIG. 30 illustrates an example of a method for illuminating a target region in a subject's body. The method may comprise: (a) generating one or more light beams using an illumination source (1310), (b) directing one or more light beams to a movable plate (1320), (c) generating one or more light pulses from the one or more light beams (1330), (d) directing the one or more light pulses to a light aggregation module (1340), (e) combining the one or more light pulses into a combined light signal (1350), (f) providing the combined light signal to a scope (1360), and (g) directing the combined light beam onto a target region (1370).

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system for illuminating a target region of a subject's body, comprising:
a plurality of illumination sources comprising: a first illumination source comprising a white light source configured to generate a white light beam and a second illumination source comprising a plurality of light emitting diodes (LEDs), a plurality of laser light sources, or a combination thereof; and
a movable plate comprising a plurality of cut-outs, wherein a first cut-out of the plurality of cut-outs is aligned with the first illumination source of the plurality of illumination sources, wherein a second cut-out of the plurality of cut-outs is aligned with the second illumination source of the plurality of illumination sources,
wherein a first imaging modality is performed with the first illumination source, wherein a second imaging modality is performed with the second illumination source, and
wherein the movable plate is configured to move so as to (a) control an exposure of the first illumination source and the second illumination source through the plurality of cut-outs, and (b) output an optical illumination corresponding to either the first imaging modality, the second imaging modality, or both.

2. The system of claim 1, wherein the white light source and the movable plate do not share a common optical axis.

3. The system of claim 1, wherein the white light beam emitted by the white light source does not pass through the movable plate.

4. The system of claim 1, wherein the white light source is transmitted continuously without being affected or separated into pulses by the movable plate.

5. The system of claim 1, wherein the plurality of cut-outs comprise a notch, an annular-shaped opening, or a combination thereof, on the movable plate.

6. The system of claim 1, wherein the plurality of illumination sources transmitted through the movable plate is aggregated by a bifurcated fiber bundle.

7. The system of claim 1, wherein the movable plate is rotated with a first rotational speed when the first illumination source is aligned with the first cut-out to generate a first exposure period of the first illumination source, and wherein the movable plate is rotated with a second rotational speed when the second illumination source is aligned with the second cut-out to generate a second exposure period of the second illumination source.

8. The system of claim 1, wherein the plurality of laser light sources comprises an infrared laser, a near-infrared laser, a short-wavelength infrared laser, a mid-wavelength infrared laser, a long-wavelength infrared laser, a far-infrared laser, or any combination thereof.

9. The system of claim 1, wherein the plurality of cut-outs is disposed on the movable plate at one or more radial distances from a center of the movable plate.

10. The system of claim 1, wherein the first illumination source transmitted through a cut-out of the plurality of cut-outs is optically coupled to a first portion of a fiber bundle, and wherein the second illumination source transmitted through a cut-out of the plurality of cut-outs is optically coupled to a second portion of the fiber bundle.

11. A method for illuminating a target region of a subject, the method comprising:
providing a plurality of illumination sources comprising: a first illumination source comprising a white light source configured to generate a white light beam and a second illumination source comprising a plurality of light emitting diodes (LEDs), a plurality of laser light sources, or a combination thereof; and
directing the plurality of illumination sources towards a movable plate comprising a plurality of cut-outs, wherein a first cut-out of the plurality of cut-outs is aligned with the first illumination source of the plurality of illumination sources, wherein a second cut-out of the plurality of cut-outs is aligned with the second illumination source of the plurality of illumination sources,
wherein a first imaging modality is performed with the first illumination source, wherein a second imaging modality is performed with the second illumination source, and
wherein the movable plate is configured to move so as to (a) control an exposure of the first illumination source and the second illumination source through the plurality of cut-outs, and (b) output an optical illumination corresponding to either the first imaging modality, the second imaging modality, or both.

12. The method of claim 11, wherein the white light source and the movable plate do not share a common optical axis.

13. The method of claim 11, wherein the white light beam emitted by the white light source does not pass through the movable plate.

14. The method of claim 11, wherein the white light source is transmitted continuously without being affected or separated into pulses by the movable plate.

15. The method of claim 11, wherein the plurality of cut-outs comprises a notch, an annular-shaped opening, or a combination thereof, on the movable plate.

16. The method of claim 11, wherein the plurality of illumination sources transmitted through the movable plate is aggregated by a bifurcated fiber bundle.

17. The method of claim 11, wherein the movable plate is rotated with a first rotational speed when the first illumination source is aligned with the first cut-out to generate a first exposure period of the first illumination source, and wherein the movable plate is rotated with a second rotational speed when the second illumination source is aligned with the second cut-out to generate a second exposure period of the second illumination source.

18. The method of claim 11, wherein the plurality of laser light sources comprise an infrared laser, a near-infrared laser, a short-wavelength infrared laser, a mid-wavelength infrared laser, a long-wavelength infrared laser, a far-infrared laser, or any combination thereof.

19. The method of claim 11, wherein the plurality of cut-outs is disposed on the movable plate at one or more radial distances from a center of the movable plate.

20. The method of claim 11, wherein the first illumination source transmitted through a cut-out of the plurality of cut-outs is optically coupled to a first portion of a fiber bundle, and wherein the second illumination source transmitted through a cut-out of the plurality of cut-outs is optically coupled to a second portion of the fiber bundle.

* * * * *